United States Patent
Chen et al.

(10) Patent No.: US 12,234,507 B2
(45) Date of Patent: Feb. 25, 2025

(54) COMPOSITIONS AND METHODS FOR TARGETED MASKING OF AUTOFLUORESCENCE

(71) Applicant: 10x Genomics, Inc., Pleasanton, CA (US)

(72) Inventors: Hong Chen, Dublin, CA (US); Joshua Delaney, Northcote (AU); Yi Luo, Dublin, CA (US); Meiliana Tjandra, Dublin, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 18/366,621

(22) Filed: Aug. 7, 2023

(65) Prior Publication Data

US 2024/0043914 A1    Feb. 8, 2024

Related U.S. Application Data

(63) Continuation of application No. PCT/US2023/017152, filed on Mar. 31, 2023.

(60) Provisional application No. 63/326,698, filed on Apr. 1, 2022.

(51) Int. Cl.
| | | |
|---|---|---|
| *C12Q 1/6841* | (2018.01) | |
| *C12Q 1/6806* | (2018.01) | |
| *C12Q 1/6876* | (2018.01) | |
| *G01N 1/30* | (2006.01) | |
| *G01N 21/64* | (2006.01) | |

(52) U.S. Cl.
CPC ......... *C12Q 1/6841* (2013.01); *C12Q 1/6806* (2013.01); *C12Q 1/6876* (2013.01); *G01N 1/30* (2013.01); *G01N 21/64* (2013.01); *G01N 2021/6432* (2013.01); *G01N 2021/6439* (2013.01)

(58) Field of Classification Search
CPC .. C12Q 1/6841; C12Q 1/6806; C12Q 1/6876; G01N 1/30; G01N 21/04; G01N 2021/6432; G01N 2021/6439
See application file for complete search history.

(56) References Cited

U.S. PATENT DOCUMENTS

| | | |
|---|---|---|
| 4,318,846 A | 3/1982 | Khanna et al. |
| 4,683,195 A | 7/1987 | Mullis et al. |
| 4,683,202 A | 7/1987 | Mullis |
| 4,757,141 A | 7/1988 | Fung et al. |
| 4,800,159 A | 1/1989 | Mullis et al. |
| 4,965,188 A | 10/1990 | Mullis et al. |
| 5,066,580 A | 11/1991 | Lee |
| 5,091,519 A | 2/1992 | Cruickshank |
| 5,151,507 A | 9/1992 | Hobbs et al. |
| 5,188,934 A | 2/1993 | Menchen |
| 5,366,860 A | 11/1994 | Bergot et al. |
| 5,512,462 A | 4/1996 | Cheng |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,750,341 A | 5/1998 | Macevicz |
| 5,800,996 A | 9/1998 | Lee et al. |
| 5,847,162 A | 12/1998 | Lee et al. |
| 5,990,479 A | 11/1999 | Weiss et al. |
| 6,172,218 B1 | 1/2001 | Brenner |
| 6,207,392 B1 | 3/2001 | Weiss et al. |
| 6,232,092 B1 | 5/2001 | Rogers |
| 6,251,303 B1 | 6/2001 | Bawendi et al. |
| 6,265,552 B1 | 7/2001 | Schatz |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,391,937 B1 | 5/2002 | Beuhler et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,828,109 B2 | 12/2004 | Kaplan et al. |
| 6,969,488 B2 | 11/2005 | Bridgham et al. |

(Continued)

FOREIGN PATENT DOCUMENTS

| | | |
|---|---|---|
| CN | 1715339 | 1/2006 |
| WO | WO 2000/075378 | 6/2000 |

(Continued)

OTHER PUBLICATIONS

Archer et al., "Selective and flexible depletion of problematic sequences from RNA-seq libraries at the cDNA stage," BMC Genomics. (2014) 15(1):401.
Berge et al., "Pharmaceutical salts," J Pharm Sci. (1977) 66(1):1-19.
Bibikova et al., "Quantitative gene expression profiling in formalin-fixed, paraffin-embedded tissues using universal bead arrays," Am J Pathol. Nov. 2004;165(5):1799-807.
Bolognesi et al., "Multiplex Staining by Sequential Immunostaining and Antibody Removal on Routine Tissue Sections," J. Histochem. Cytochem. (2017); 65(8): 431-444.
Capodieci et al., "Gene expression profiling in single cells within tissue," Nat Methods. (2005) 2(9): 663-5.
Chemeris et al., "Real-time hybridization chain reaction," Dokl Biochem Biophys. (2008) 419: 53-55.

(Continued)

*Primary Examiner* — Jezia Riley
(74) *Attorney, Agent, or Firm* — MORRISON & FOERSTER LLP

(57) ABSTRACT

The present disclosure generally relates to methods and compositions for in situ analysis or detection of analytes in a biological sample. More specifically, the present disclosure relates to methods for reducing autofluorescence in tissue samples, methods for analyzing tissue samples, and compounds for use in the same. The methods and compounds of the present disclosure may be especially suitable for analytical methods employing fluorescence in situ hybridization techniques over multiple cycles of imaging.

30 Claims, 18 Drawing Sheets
(2 of 18 Drawing Sheet(s) Filed in Color)

(56) References Cited

U.S. PATENT DOCUMENTS

| | | |
|---|---|---|
| 7,019,129 B1 | 3/2006 | Cook et al. |
| 7,057,026 B2 | 6/2006 | Barnes et al. |
| 7,109,312 B2 | 9/2006 | Cook et al. |
| 7,160,996 B1 | 1/2007 | Cook |
| 7,255,994 B2 | 8/2007 | Lao |
| 7,473,767 B2 | 1/2009 | Dimitrov |
| 7,534,991 B2 | 5/2009 | Miller et al. |
| 7,555,155 B2 | 6/2009 | Levenson et al. |
| 7,582,432 B2 | 9/2009 | Cook et al. |
| 7,632,641 B2 | 12/2009 | Dirks et al. |
| 7,635,598 B2 | 12/2009 | Cook et al. |
| 7,655,898 B2 | 2/2010 | Miller |
| 7,709,198 B2 | 5/2010 | Luo et al. |
| 7,721,721 B1 | 5/2010 | Kronengold et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,410,255 B2 | 4/2013 | Cook et al. |
| 8,415,102 B2 | 4/2013 | Geiss et al. |
| 8,431,691 B2 | 4/2013 | McKernan et al. |
| 8,440,399 B2 | 5/2013 | Cook et al. |
| 8,460,865 B2 | 6/2013 | Chee et al. |
| 8,462,981 B2 | 6/2013 | Determan et al. |
| 8,466,266 B2 | 6/2013 | Cook et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,604,182 B2 | 12/2013 | Luo et al. |
| 8,633,307 B2 | 1/2014 | Cook et al. |
| 8,637,658 B2 | 1/2014 | Ewing et al. |
| 8,658,361 B2 | 2/2014 | Wu et al. |
| 8,674,094 B2 | 3/2014 | Cook et al. |
| 8,771,950 B2 | 7/2014 | Church et al. |
| 8,946,404 B2 | 2/2015 | Cook et al. |
| 8,951,726 B2 | 2/2015 | Luo et al. |
| 8,986,926 B2 | 3/2015 | Ferree et al. |
| 9,018,369 B2 | 4/2015 | Cook et al. |
| 9,139,610 B2 | 9/2015 | Cook et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,803,240 B2 | 10/2017 | Cook et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,301,349 B2 | 5/2019 | Cook et al. |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,450,599 B2 | 10/2019 | Pierce et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0045045 A1 | 4/2002 | Adams et al. |
| 2003/0017264 A1 | 1/2003 | Treadway et al. |
| 2005/0100900 A1 | 5/2005 | Kawashima et al. |
| 2006/0188901 A1 | 8/2006 | Barnes et al. |
| 2006/0234261 A1 | 10/2006 | Pierce et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2010/0055733 A1 | 3/2010 | Lutolf et al. |
| 2011/0223585 A1 | 9/2011 | Gullberg et al. |
| 2011/0256183 A1 | 10/2011 | Frank et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0233878 A1 | 8/2019 | Delaney et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0307390 A1 | 10/2019 | Bawendi et al. |
| 2019/0339203 A1 | 11/2019 | Miller et al. |
| 2019/0367969 A1 | 12/2019 | Belhocine |

(56) References Cited

U.S. PATENT DOCUMENTS

| | | |
|---|---|---|
| 2019/0376956 A1 | 12/2019 | Bobrow et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2020/0399689 A1 | 12/2020 | Luo et al. |
| 2021/0017587 A1 | 1/2021 | Cai et al. |
| 2021/0115504 A1 | 4/2021 | Cai et al. |
| 2021/0164039 A1 | 6/2021 | Wang et al. |
| 2021/0215581 A1 | 7/2021 | Deisseroth et al. |
| 2021/0222234 A1 | 7/2021 | Carlson |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340618 A1 | 11/2021 | Kuhnemund et al. |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0010358 A1 | 1/2022 | Kuhnemund et al. |
| 2022/0026433 A1 | 1/2022 | Guo et al. |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0128565 A1 | 4/2022 | Miller et al. |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0282306 A1* | 9/2022 | Bava .................... C12Q 1/6816 |
| 2023/0039899 A1 | 2/2023 | Larman et al. |
| 2023/0041485 A1* | 2/2023 | Hernandez ........... C12Q 1/6841 |

FOREIGN PATENT DOCUMENTS

| | | |
|---|---|---|
| WO | WO 2001/086001 | 11/2001 |
| WO | WO 2003/019145 | 3/2003 |
| WO | WO 2005/065814 | 7/2005 |
| WO | WO 2006/010038 | 1/2006 |
| WO | WO 2006/064199 | 6/2006 |
| WO | WO 2007/010251 | 1/2007 |
| WO | WO 2009/124150 | 10/2009 |
| WO | WO 2014/025392 | 2/2014 |
| WO | WO 2014/163886 | 10/2014 |
| WO | WO 2017/079406 | 5/2017 |
| WO | WO 2017/143155 | 8/2017 |
| WO | WO 2018/026873 | 2/2018 |
| WO | WO 2019/199579 | 10/2019 |
| WO | WO 2019/236841 | 12/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/102094 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/163397 | 8/2020 |
| WO | WO 2020/240025 | 12/2020 |
| WO | WO 2020/254519 | 12/2020 |
| WO | WO 2021/067475 | 4/2021 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/167526 | 8/2021 |
| WO | WO 2021/168326 | 8/2021 |

OTHER PUBLICATIONS

Chen et al., "Nanoscale imaging of RNA with expansion microscopy," Nat Methods. (2016) 13:679-684.

Chen et al., "RNA imaging. Spatially resolved, highly multiplexed RNA profiling in single cells," Science. (2015) 348(6233): aaa6090. 16 pgs.

Chen et al., "Expansion Microscopy," Science (2015) 347(6221):543-548.

Chevalier et al., "Bioconjugatable azo-based dark-quencher dyes: synthesis and application to protease-activatable far-red fluorescent probes," Chemistry. (2013) 28;19(5):1686-99.

Chevalier et al., "Straightforward synthesis of bioconjugatable azo dyes. Part 2: Black Hole Quencher-2 (BHQ-2) and BlackBerry Quencher 650 (BBQ-650) scaffolds," Tetrahedron Letters. (2014) 55(50); 6764-6768.

Choi et al., "Programmable in situ amplification for multiplexed imaging of mRNA expression," Nat Biotechnol. (2010) 28(11): 1208-1212.

Choi et al., "Third-generation in situ hybridization chain reaction: multiplexed, quantitative, sensitive, versatile, robust," Development. (2018) 6;145(12): dev165753.

Conze et al., "Single molecule analysis of combinatorial splicing," Nucleic Acids Res. (2010) 38(16): e163.

Dirks et al., "Triggered amplification by hybridization chain reaction," Proc Natl Acad Sci USA. (2004) 101(43): 15275-15278.

Du et al., "Qualifying antibodies for image-based immune profiling and multiplexed tissue imaging," Nat Protoc. (2019) 14(10):2900-2930.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Frei et al., "Highly multiplexed simultaneous detection of RNAs and proteins in single cells," Nat Methods. (2016) 13(3): 269-275.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

(56) References Cited

OTHER PUBLICATIONS

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Levene et al. "Zero-mode waveguides for single-molecule analysis at high concentrations." *science* 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lundquist et al. "Parallel confocal detection of single molecules in real time." Optics letters 33.9 (2008): 1026-1028.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Meeker et al., "Photochemical pre-bleaching of formalin-fixed archival prostate tissues significantly reduces autofluorescence to facilitate multiplex immunofluorescence staining," Preprint from bioRxiv, Nov. 11, 2021 DOI: 10.1101/2021.11.09.467916 PPR: PPR418815.

Nagendran et al., "Automated cell-type classification in intact tissues by single-cell molecular profiling," Elife. (2018) 7:e30510.

Niu et al., "Fluorescence detection for DNA using hybridization chain reaction with enzyme-amplification," Chem C+A277ommun (Camb). (2010) 46(18): 3089-91.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Rouhanifard et al. "ClampFISH detects individual nucleic acid molecules using click chemistry-based amplification," Nat Biotechnol. (2018) 17 pages. doi: 10.1038/nbt.4286.

Shendure et al., "Accurate multiplex polony sequencing of an evolved bacterial genome," Science (2005) 309(5741); 1728-1732.

Song et al., "Hybridization chain reaction-based aptameric system for the highly selective and sensitive detection of protein," Analyst. (2012) 137(6):1396-1401.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.

Tripathi et al., "Z Probe, An Efficient Tool for Characterizing Long Non-Coding RNA in FFPE Tissues," Noncoding RNA. (2018) 4(3):20.

Tsuneoka et al., "Modified in situ Hybridization Chain Reaction Using Short Hairpin DNAs," Front Mol Neurosci. (2020) 13:75.

Vandernoot et al., "cDNA normalization by hydroxyapatite chromatography to enrich transcriptome diversity in RNA-seq applications," Biotechniques, (2012) 53(6) 373-80.

Wählby et al., "Sequential immunofluorescence staining and image analysis for detection of large numbers of antigens in individual cell nuclei," Cytometry. (2002) 47(1): 32-41.

Weibrecht et al., "Simultaneous visualization of both signaling cascade activity and end-point gene expression in single cells," PLoS One. (2011) 6(5): e20148.

Wetmur, "DNA Probes: Applications of the Principles of Nucleic Acid Hybridization," Critical Reviews in Biochemistry and Molecular Biology, (1991) 26(91); 227-259.

Wilson et al., "Encoded microcarriers for high-throughput multiplexed detection," Angew Chem Int Ed Engl. (2006) 18;45(37): 6104-17.

Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Xia et al. "Multiplexed detection of RNA using MERFISH and branched DNA amplification." Scientific reports 9.1 (2019): 1-13.

Zhao et al., "Advances of multiplex and high throughput biomolecular detection technologies based on encoding microparticles," Sci China Chem. (2011) 54(8):1185.

\* cited by examiner

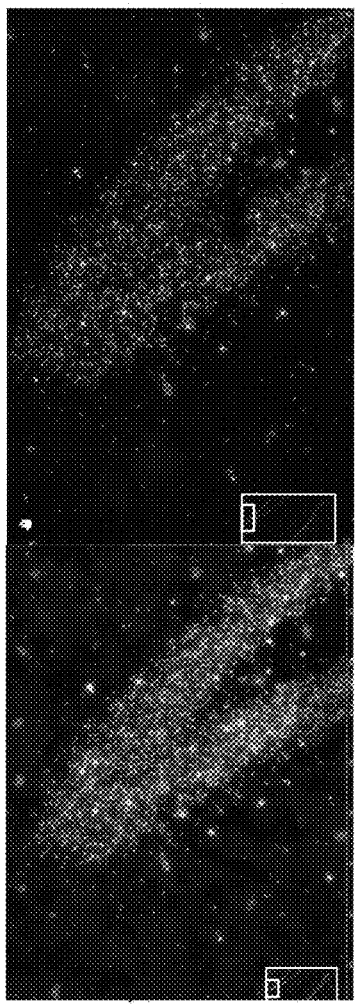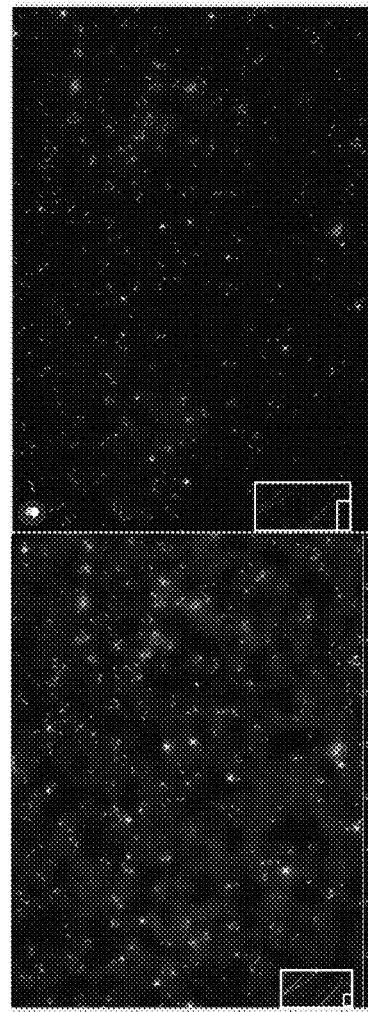
FIG. 3A  FIG. 3B  FIG. 3C  FIG. 3D

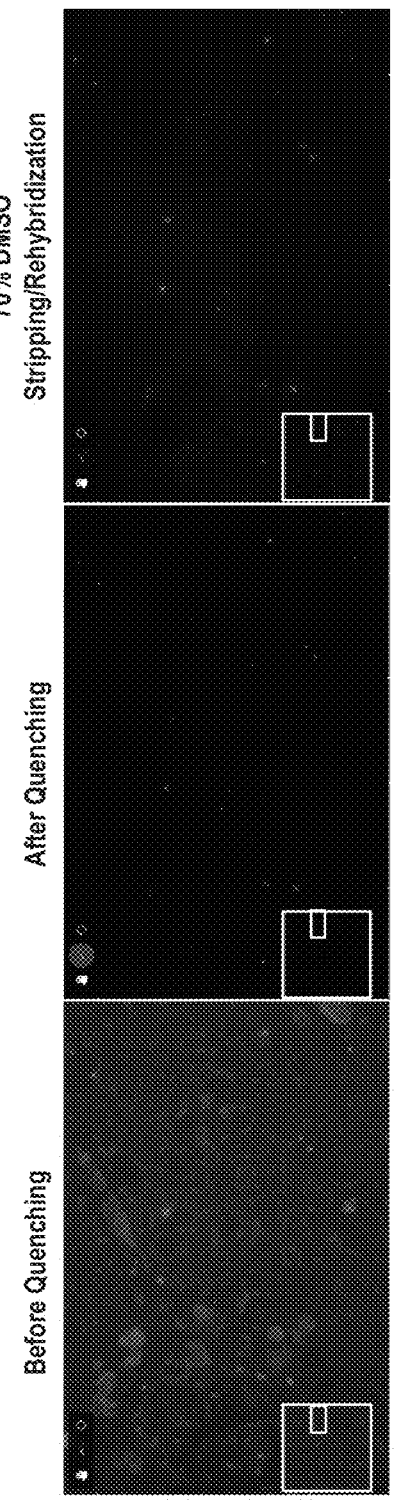

COMPOSITIONS AND METHODS FOR TARGETED MASKING OF AUTOFLUORESCENCE

CROSS-REFERENCE TO RELATED APPLICATION

This application is a continuation of International Application No. PCT/US2023/017152, filed on Mar. 31, 2023, which claims priority to U.S. Provisional Patent Application No. 63/326,698, filed Apr. 1, 2022, entitled "COMPOSITIONS AND METHODS FOR TARGETED MASKING OF AUTOFLUORESCENCE," which is herein incorporated by reference in its entirety for all purposes.

FIELD

The present disclosure generally relates to methods and compositions for analysis or detection of analytes in a biological sample, particularly for in situ analysis of biomolecules in cell or tissue sample.

BACKGROUND

Methods are available for analyzing nucleic acids in a biological sample in situ, such as a cell or a tissue. For instance, advances in single molecule fluorescent hybridization (smFISH) have enabled nanoscale-resolution imaging of RNA in cells and tissues. However, oligonucleotide probe-based assay methods for in situ analysis may suffer from low sensitivity, specificity, and/or detection efficiency, particularly in the presence of background autofluorescence. Autofluorescence is typically generated by biological moieties endogenous to the tissue and cell samples. Autofluorescence can also arise from and/or be exacerbated by standard sample treatments, such as formalin-fixation. Background autofluorescence may have a significant, ongoing impact on the ability to detect and resolve fluorescence signals from analytes of interest over other components also present in the biological samples, especially when analysis is carried out over multiple cycles or rounds of imaging. Improved methods for in situ analysis are needed. The present disclosure addresses these and other needs.

BRIEF SUMMARY

In some aspects, the present disclosure relates to methods for reducing autofluorescence in tissue samples, methods for analyzing biological samples, and compounds for use in the same. In some aspects, the methods and compounds of the present disclosure are suitable for analytical methods employing fluorescence imaging over multiple cycles and using multiple wavelengths.

In one aspect, provided herein is a method for reducing autofluorescence, comprising contacting a tissue sample with a quencher comprising a quenching moiety (e.g., a quencher dye) and a targeting moiety, where the targeting moiety binds and/or reacts with a biological moiety endogenous in the tissue sample, thereby targeting the quencher to the endogenous biological moiety; and detecting a signal associated with a detectable probe directly or indirectly bound to a molecule of interest in the tissue sample, wherein the quencher reduces autofluorescence in the tissue sample. In some embodiments, the quenching moiety (e.g., quencher dye) and the targeting moiety are physically coupled to each other, whereas the quenching moiety and the detectable probe are not physically coupled to each other. For instance, the quenching moiety and the targeting moiety can be covalently by a bond or a linker, whereas the quenching moiety and the detectable probe are physically separate prior to contacting with the tissue sample.

In some embodiments, the autofluorescence of the tissue sample is reduced as compared to an unquenched tissue sample. In some embodiments, the autofluorescence is reduced by at least about 50%, at least about 60%, at least about 70% or at least about 80% as compared to an unquenched tissue sample. In some embodiments, signals associated with detectable probes are detected at locations in the tissue sample and the detected signal has a signal-to-noise ratio that is increased as compared to an unquenched tissue sample. In some embodiments, signals detected at a location in the tissue sample are analyzed to generate a signal-to-noise ratio that is increased as compared to an unquenched tissue sample. In some embodiments, the signal-to-noise ratio is increased by at least about 10%, at least about 20%, or at least about 25% as compared to an unquenched tissue sample. In some embodiments, signals associated with detectable probes are detected at locations in the tissue sample and a detectable object count density associated with the tissue sample is increased as compared to an unquenched tissue sample. In some embodiments, signals associated with detectable probes are detected at locations in the tissue sample and are analyzed to generate a detectable object count density that is increased as compared to an unquenched tissue sample. In some embodiments, the detectable object count density is increased by at least about 2 times, at least about 3 times, at least about 4 times, or at least about 5 times as compared to an unquenched tissue sample.

In some embodiments, the tissue sample is contacted with the detectable probe prior to being contacted with the quencher. In some embodiments, the tissue sample is contacted with the detectable probe after being contacted with the quencher. In some embodiments, the tissue sample is contacted with the detectable probe and the quencher simultaneously.

In some embodiments, the method further comprises bleaching the tissue sample with a chemical reagent, an enzyme, light, heat, or any combination thereof, prior to, simultaneously, or after the contacting of the tissue sample with the quencher comprising the quencher dye and the targeting moiety.

In some embodiments, the method further comprises removing the detectable probe or a portion thereof from the tissue sample, wherein the quencher remains in the tissue sample. In some embodiments, the removing step comprises treating the tissue sample with a denaturing agent and/or heating. In some embodiments, the denaturing agent comprises dimethyl sulfoxide (DMSO), formamide, and/or an alkaline solution.

In some embodiments, the method further comprises contacting the tissue sample with one or more additional detectable probes, wherein each additional detectable probe directly or indirectly binds to an additional molecule of interest in the tissue sample, and the additional molecule of interest is the same or different from the molecule of interest. In some embodiments, the method further comprises detecting a signal or signals associated with the one or more additional detectable probes in the tissue sample, wherein the autofluorescence of the tissue sample remains at least partially quenched by the quenching moiety of the quencher. In some embodiments, during the detection of the signal or signals associated with the one or more additional detectable probes, the autofluorescence of the tissue sample remains reduced as compared to an unquenched tissue sample. In some embodiments, the one or more additional detectable probes are contacted with the tissue sample and the signal or signals associated with the one or more additional detectable probes are detected in one or more cycles. In some embodiments, each cycle comprises removing the additional detectable probe(s) for the cycle from the tissue sample prior to contacting the tissue sample with the additional detectable probe(s) for a subsequent cycle. In some embodiments, the autofluorescence of the tissue sample remains at least partially quenched by the quenching moiety of the quencher during the detection of the signal or signals associated with the detectable probes in the sequential cycles.

In some embodiments, the molecule of interest and the additional molecule of interest are independently selected from the group consisting of a nucleic acid (e.g., genomic DNA, RNA, or cDNA), a protein or peptide, a carbohydrate, a lipid, a small molecule, and a complex thereof. In some embodiments, the molecule of interest is a first nucleic acid (e.g., an mRNA transcript of a first gene) and the additional molecule of interest is a second nucleic acid (e.g., an mRNA transcript of a second, different gene, or a different mRNA transcript of the first gene). In some embodiments, the molecule of interest is a first protein and the additional molecule of interest is a second, different protein. In some embodiments, the molecule of interest is a nucleic acid (e.g., an mRNA transcript of a gene) and the additional molecule of interest is a protein (e.g., a protein encoded by the gene or by a different gene), or vice versa. In some embodiments, the molecule of interest is a nucleic acid (e.g., an mRNA transcript of a gene, a probe that directly or indirectly binds the mRNA transcript, or a rolling circle amplification product of the mRNA transcript or the probe) and the additional molecule of interest is the same nucleic acid, where the detectable probe (which targets the molecule of interest) and the additional detectable probe (which targets the additional molecule of interest) are the same or different. In cases where the detectable probe and the additional detectable probe are different, they can be different in their nucleic acid sequences and/or in their detectable labels, but probes still directly or indirectly bind the same nucleic acid and the binding can be at the same sequence or different sequences in the nucleic acid.

In some embodiments, which may be after a given cycle, the quencher remains in the tissue sample and autofluorescence of the tissue sample remains reduced as compared to an unquenched tissue sample. In some embodiments, the autofluorescence remains reduced by at least about 50%, at least about 60%, at least about 70% or at least about 80% for a given cycle as compared to an unquenched tissue sample. In some embodiments, the autofluorescence increases by less than about 5%, less than about 10% or less than about 15% for a given cycle as compared to the preceding cycle. In some embodiments, after a given cycle, the signal-to-noise ratio remains increased as compared to an unquenched tissue sample. In some embodiments, the signal-to-noise ratio remains increased by at least about 10%, at least about 20%, or at least about 25% for a given cycle as compared to an unquenched tissue sample. In some embodiments, the signal-to-noise ratio decreases by less than about 5%, less than about 10% or less than about 15% for a given cycle as compared to the preceding cycle. In some embodiments, the detectable object count density remains increased for a given cycle as compared to an unquenched tissue sample. In some embodiments, the detectable object count density remains increased by at least about 2 times, at least about 3 times, at least about 4 times, or at least about 5 times for a given cycle as compared to an unquenched tissue sample. In some embodiments, the detectable object count density decreases by less than about 5%, less than about 10% or less than about 15% for a given cycle as compared to the preceding cycle. In some embodiments, the method comprises at least two, three, four, five, six, or more cycles of contacting the tissue sample with the one or more additional detectable probes.

In some embodiments, the method further comprises bleaching the tissue sample with a chemical reagent, an enzyme, light, heat, or any combination thereof, prior to, simultaneously, or after the contacting the tissue sample with the quencher.

In some embodiments, the method further comprises staining the tissue sample. In some embodiments, the method further comprises fixing the tissue sample. In some embodiments, the method further comprises de-crosslinking the tissue sample.

In another aspect, provided herein is a method for analyzing a biological sample, comprising: contacting the biological sample with a quencher comprising a quencher dye and a targeting moiety, wherein the targeting moiety directly or indirectly binds and/or reacts with a biological moiety endogenous to the biological sample, thereby targeting the quencher to the biological moiety; contacting the biological sample with a detectable probe that directly or indirectly binds to a molecule of interest in the biological sample; and detecting a signal associated with the detectable probe bound to the molecule of interest in the biological sample, wherein the quencher dye reduces autofluorescence of the biological sample, thereby detecting the molecule of interest in the biological sample.

In some embodiments, the quencher reduces the autofluorescence of the biological sample without substantially reducing the signal associated with the detectable probe. In some embodiments, the autofluorescence of the biological sample is reduced as compared to an unquenched biological sample. In some embodiments, the autofluorescence is reduced by at least about 50%, at least about 60%, at least about 70% or at least about 80% as compared to an unquenched biological sample. In some embodiments, the signal associated with the detectable probe is detected at a location in the biological sample, and the detected signal has a signal-to-noise ratio that is increased as compared to an unquenched biological sample. In some embodiments, the in situ signal detection in the biological sample generates a signal-to-noise ratio that is increased as compared to an unquenched biological sample. In some embodiments, the signal-to-noise ratio is increased by at least about 10%, at least about 20%, or at least about 25% as compared to an unquenched biological sample. In some embodiments, a detectable object count density associated with the biological sample is increased as compared to an unquenched biological sample. In some embodiments, the in situ signal detection in the biological sample generates a detectable object count density that is increased as compared to an unquenched biological sample. In some embodiments, the detectable object count density is increased by at least about 2 times, at least about 3 times, at least about 4 times, or at least about 5 times as compared to an unquenched biological sample.

In some embodiments, the biological sample is contacted with the detectable probe prior to being contacted with the quencher. In other embodiments, the biological sample is contacted with the detectable probe after being contacted with the quencher. In yet other embodiments, the biological sample is contacted with the detectable probe and the quencher simultaneously.

In some embodiments, the method further comprises bleaching the biological sample with a chemical reagent, an enzyme, light, heat, or any combination thereof, prior to, simultaneously, or after the contacting of the biological sample with the detectable probe that directly or indirectly binds to the molecule of interest in the biological sample.

In some embodiments, prior to contacting the biological sample with a detectable probe that directly or indirectly binds to a molecule of interest in the biological sample, the method comprises contacting the biological sample with a nucleic acid probe that directly or indirectly binds to the molecule of interest in the biological sample, and wherein the detectable probe binds directly or indirectly to the nucleic acid probe.

In some embodiments, the method further comprises removing the detectable probe or a portion thereof from the biological sample, wherein the quencher remains in the biological sample. In some embodiments, the removing step comprises treating the biological sample with a denaturing agent and/or heating. In some embodiments, the denaturing agent comprises dimethyl sulfoxide (DMSO), formamide, and/or an alkaline solution. In some embodiments, the method further comprises contacting the biological sample with one or more additional detectable probes, wherein each additional detectable probe directly or indirectly binds to an additional molecule of interest in the biological sample, and the additional molecule of interest is the same or different from the molecule of interest.

In some embodiments, the method further comprises detecting a signal or signals associated with the one or more additional detectable probes in the biological sample, wherein the autofluorescence of the biological sample remains reduced as compared to an unquenched biological sample. In some embodiments, the one or more additional detectable probes are contacted with the biological sample and the signal or signals associated with the one or more additional detectable probes are detected in one or more cycles. In some embodiments, each cycle comprises removing the additional detectable probe(s) for the cycle from the biological sample prior to contacting the biological sample with the additional detectable probe(s) for a subsequent cycle.

In some embodiments, after a given cycle, the quencher remains in the biological sample and autofluorescence of the biological sample remains reduced as compared to an unquenched biological sample. In some embodiments, the autofluorescence remains reduced by at least about 50%, at least about 60%, at least about 70% or at least about 80% for a given cycle as compared to an unquenched biological sample. In some embodiments, the autofluorescence increases by less than about 5%, less than about 10% or less than about 15% for a given cycle as compared to the preceding cycle. In some embodiments, after a given cycle, the signal-to-noise ratio remains increased as compared to an unquenched biological sample. In some embodiments, the signal-to-noise ratio remains increased by at least about 10%, at least about 20%, or at least about 25% for a given cycle as compared to an unquenched biological sample. In some embodiments, the signal-to-noise ratio decreases by less than about 5%, less than about 10% or less than about 15% for a given cycle as compared to the preceding cycle. In some embodiments, the detectable object count density remains increased for a given cycle as compared to an unquenched biological sample. In some embodiments, the detectable object count density remains increased by at least about 2 times, at least about 3 times, at least about 4 times, or at least about 5 times for a given cycle as compared to an unquenched biological sample. In some embodiments, the detectable object count density decreases by less than about 5%, less than about 10% or less than about 15% for a given cycle as compared to the preceding cycle.

In some embodiments, the method comprises comprising at least two, three, four, five, six, or more cycles of contacting the biological sample with the one or more additional detectable probes.

In some embodiments, the method further comprises staining the biological sample. In some embodiments, the method further comprises fixing the biological sample. In some embodiments, the method further comprises de-cross-linking the biological sample.

In some embodiments, the biological sample is a tissue sample.

In some embodiments of any of the preceding aspects, each detectable probe is independently detectably labeled or hybridizes to a detectably labeled probe. In some embodiments, each detectable probe is independently covalently labeled with a fluorophore or hybridizes to a probe covalently labeled with a fluorophore. In some embodiments of any of the preceding aspects, the quencher further comprises a linker moiety linking the quencher dye and the targeting moiety. In certain embodiments, the linker moiety is an alkylene moiety, an aminoalkylene moiety, an amino(alkyl) alkylene moiety, a polyethylene glycol moiety, a disulfide moiety, or a carbamate moiety.

In some embodiments of any of the preceding aspects, the quencher dye comprises: (a) at least three aromatic residues, wherein each aromatic residue is independently unsubstituted aryl, substituted aryl, unsubstituted heteroaryl, or substituted heteroaryl, wherein at least one aromatic residue is covalently linked to two other aromatic residues via two exocyclic azo bonds; or (b) at least two aromatic residues, wherein each aromatic residue is independently unsubstituted aryl, substituted aryl, unsubstituted heteroaryl, or substituted heteroaryl, wherein at least two of said aromatic residues are covalently linked via an exocyclic azo bond, wherein at least one said aromatic residue is an unsubstituted polycyclic aryl, a substituted polycyclic aryl, an unsubstituted polycyclic heteroaryl group, or a substituted polycyclic heteroaryl group. In some embodiments of any of the preceding aspects, the quencher dye comprises an optionally substituted 1,4-bis((E)-phenyldiazenyl)benzene moiety

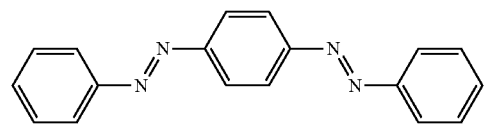

or an optionally substituted (E)-5-phenyl-3-(phenyldiazenyl)phenazin-5-ium moiety

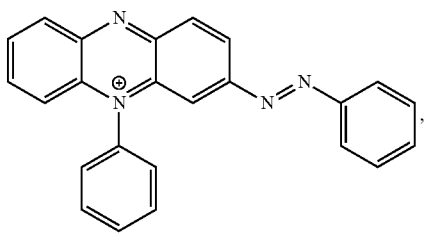 [SMILES: c1ccc(/N=N/c2ccc3nc4ccccc4[n+](-c4ccccc4)c3c2)cc1]

or a salt thereof. In some embodiments of any of the preceding aspects, the quencher has a UV-visible absorption spectrum as shown in FIG. 1. In some embodiments of any of the preceding aspects, the quencher has a UV-visible absorption profile with at least one absorption peak with an absorption maximum between about 400 nm and 700 nm and full-width half-maximum of at least about 100 nm. In some embodiments of any of the preceding aspects, the quencher has a UV-visible absorption profile with at least one absorption peak with an absorption maximum between about 500 and about 600 nm and full-width half-maximum of at least about 100 nm.

In some embodiments of any of the preceding aspects, the quencher is a compound formula (I)

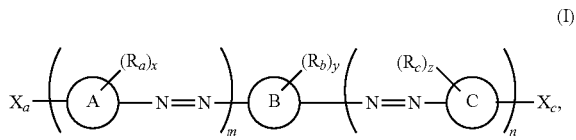

or a salt thereof, as defined herein.

In some embodiments of any of the preceding aspects, the quencher is a compound formula (II)

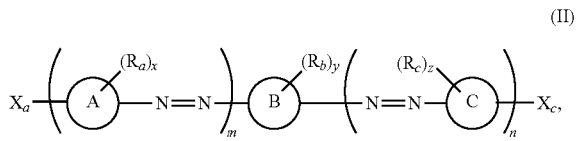

or a salt thereof, as defined herein.

In yet another aspect, provided herein is a method for analyzing a tissue sample, comprising contacting the tissue sample with a nucleic acid probe that directly or indirectly binds to a molecule of interest in the tissue sample; contacting the tissue sample with a quencher comprising a quencher dye and a targeting moiety, wherein the targeting moiety directly or indirectly binds and/or reacts with a biological moiety endogenous in the tissue sample, thereby targeting the quencher to the biological moiety, wherein the quencher is a compound of formula (I) or Formula (II), or a salt thereof, as defined herein; contacting the tissue sample with a fluorescently labeled detectable probe that directly or indirectly binds the nucleic acid probe or an amplification product of the nucleic acid probe; and detecting a signal associated with the fluorescently labeled detectable probe in the tissue sample, wherein the quencher dye reduces autofluorescence in the tissue sample, thereby detecting the molecule of interest in the tissue sample.

In some embodiments, the autofluorescence of the tissue sample is reduced as compared to an unquenched tissue sample. In some embodiments, the autofluorescence is reduced by at least about 50%, at least about 60%, at least about 70% or at least about 80% as compared to an unquenched tissue sample. In some embodiments, the in situ signal detection generates a signal-to-noise ratio that is increased as compared to an unquenched tissue sample. In some embodiments, the detected signal has a signal-to-noise ratio, wherein the signal-to-noise ratio is increased as compared to an unquenched tissue sample. In some embodiments, the signal-to-noise ratio is increased by at least about 10%, at least about 20%, or at least about 25% as compared to an unquenched tissue sample. In some embodiments, the in situ signal detection generates a detectable object count density that is increased as compared to an unquenched tissue sample. In some embodiments, the signal associated with the detectable probe is detected at a location in the tissue sample, and a detectable object count density associated with the tissue sample is increased as compared to an unquenched tissue sample. In some embodiments, the detectable object count density is increased by at least about 2 times, at least about 3 times, at least about 4 times, or at least about 5 times as compared to an unquenched tissue sample.

In some embodiments, the tissue sample is contacted with the detectable probe prior to being contacted with the quencher. In other embodiments, the tissue sample is contacted with the detectable probe after being contacted with the quencher. In yet other embodiments, the tissue sample is contacted with the detectable probe and the quencher simultaneously.

In some embodiments, the method further comprises bleaching the tissue sample with a chemical reagent, an enzyme, light, heat, or any combination thereof, prior to, simultaneously, or after contacting the tissue sample with the quencher.

In some embodiments, the method further comprises removing the detectable probe or a portion thereof from the tissue sample, wherein the quencher remains in the tissue sample. In some embodiments, the removing step comprises treating the tissue sample with a denaturing agent and/or heating. In some embodiments, the denaturing agent comprises dimethyl sulfoxide (DMSO), formamide, and/or an alkaline solution.

In some embodiments, the method further comprises contacting the tissue sample with one or more additional detectable probes, wherein each additional detectable probe directly or indirectly binds to an additional molecule of interest in the tissue sample, and the additional molecule of interest is the same or different from the molecule of interest. In some embodiments, the method further comprises detecting a signal or signals associated with the one or more additional detectable probes in the tissue sample, wherein the autofluorescence of the tissue sample remains reduced as compared to an unquenched tissue sample. In some embodiments, the one or more additional detectable probes are contacted with the tissue sample and the signal or signals associated with the one or more additional detectable probes are detected in one or more cycles. In some embodiments, each cycle comprises removing the additional detectable probe(s) for the cycle from the tissue sample prior to contacting the tissue sample with the additional detectable probe(s) for a subsequent cycle. In some embodiments, after a given cycle, the quencher remains in the tissue sample and autofluorescence of the tissue sample remains reduced as compared to an unquenched tissue sample. In some embodiments, the autofluorescence remains reduced by at least about 50%, at least about 60%, at least about 70% or at least about 80% for a given cycle as compared to an unquenched tissue sample. In some embodiments, the autofluorescence increases by less than about 5%, less than about 10% or less than about 15% for a given cycle as compared to the preceding cycle. In some embodiments, after a given cycle, the signal-to-noise ratio remains increased as compared to an unquenched tissue sample. In some embodiments, the signal-to-noise ratio remains increased by at least about 10%, at least about 20%, or at least about 25% for a given cycle as compared to an unquenched tissue sample. In some embodiments, the signal-to-noise ratio decreases by less than about 5%, less than about 10% or less than about 15% for a given cycle as compared to the preceding cycle. In some embodiments, the detectable object count density remains increased for a given cycle as compared to an unquenched tissue sample. In some embodiments, the detectable object count density remains increased by at least about 2 times, at least about 3 times, at least about 4 times, or at least about 5 times for a given cycle as compared to an unquenched tissue sample. In some embodiments, the detectable object count density decreases by less than about 5%, less than about 10% or less than about 15% for a given cycle as compared to the preceding cycle.

In some embodiments, the method comprises at least two, three, four, five, six, or more cycles of contacting the tissue sample with the one or more additional detectable probes.

In some embodiments, the method further comprises staining the tissue sample. In some embodiments, the method further comprises fixing the tissue sample. In some embodiments, the method further comprises de-crosslinking the tissue sample.

In some embodiments wherein the quencher is a compound of formula (I), m is an integer from 1 to 6 and n is an integer from 1 to 6. In some embodiments wherein the quencher is a compound of formula (I), at least one, at least two or at least three instances of

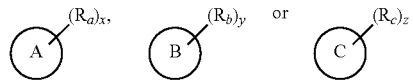

or is substituted phenyl or unsubstituted phenyl.

In some embodiments wherein the quencher is a compound of formula (II), m is an integer from 1 to 6 and n is an integer from 1 to 6. In some embodiments wherein the quencher is a compound of formula (II), at least one, at least two or at least three instances of

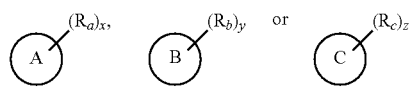

or is substituted phenyl or unsubstituted phenyl.

In some embodiments of any of the preceding aspects, the quencher has the following structure:

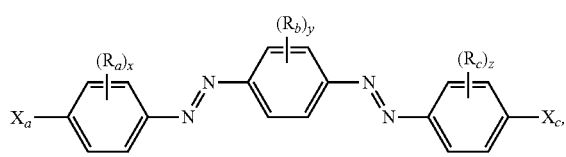

or a salt thereof, provided that at least one of $X_a$ and $X_c$ is -L-$(R_{target})_w$, wherein w is any integer such as 1 or 2, and wherein L is a bond or a linker moiety; and $R_{target}$ is a targeting moiety.

In some embodiments of any of the preceding aspects, the quencher has the following structure:

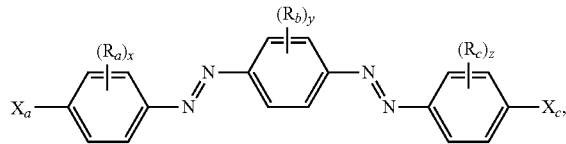

or a salt thereof, provided that at least one of $X_a$ and $X_c$ is -L-$R_{target}$, wherein L is a bond or a linker moiety; and $R_{target}$ is a targeting moiety.

In some embodiments wherein the quencher is a compound of formula (I) or Formula (II),

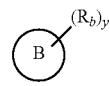

is

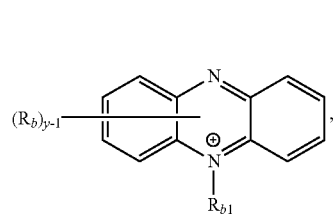

wherein $R_{b1}$ is a substituted or unsubstituted alkyl, a substituted or unsubstituted aryl, or a substituted or unsubstituted heteroaryl. In certain embodiments

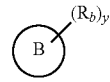

is

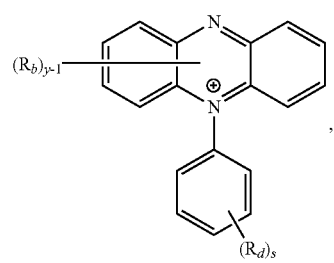

wherein $R_d$ is H, $C_1$-$C_6$ alkyl, or halo; and s is an integer from 0 to 5.

In some embodiments of any of the preceding aspects, the quencher has the following structure:

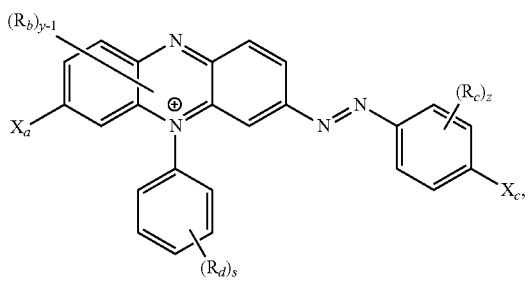

or a salt thereof.

In some embodiments of any of the preceding aspects, which may be combined with any of the preceding embodiments, the molecule of interest is a nucleic acid of interest or a protein of interest. In some embodiments, the detectable probe hybridizes to the nucleic acid of interest. In some embodiments, the detectable probe hybridizes to one or more intermediate probes which directly or indirectly bind to the nucleic acid of interest. In some embodiments, the detectable probe hybridizes to one or more intermediate probes which in turn hybridize to the nucleic acid of interest. In some embodiments of any of the preceding methods, the method further comprises adding a primary probe prior to adding the detectable probe and one or more intermediate probes, wherein the intermediate probe binds to the primary probe or a product thereof.

In some embodiments of any of the preceding aspects, which may be combined with any of the preceding embodiments, the nucleic acid of interest is a cellular or viral DNA or RNA or a product thereof. In some embodiments, the cellular or viral DNA or RNA or product thereof is a genomic DNA, a coding RNA, a non-coding RNA, or a cDNA. In certain embodiments, the nucleic acid of interest is an mRNA.

In some embodiments, the nucleic acid of interest is a nucleic acid probe that directly or indirectly binds to a cellular or viral DNA or RNA or a product thereof. In some embodiments, the cellular or viral DNA or RNA or product thereof is a genomic DNA, a coding RNA, a non-coding RNA, or a cDNA. In certain embodiments, the coding RNA is an mRNA.

In some embodiments of any of the preceding aspects, which may be combined with any of the preceding embodiments, the nucleic acid probe is linear, circularizable, circular, or branched. In some embodiments, the nucleic acid probe comprises a 3' overhang and/or a 5' overhang upon hybridization to the cellular or viral DNA or RNA or product thereof. In some embodiments, the nucleic acid probe comprises one or more barcode regions.

In some embodiments, the nucleic acid of interest is a probe product of one or more nucleic acid probes that directly or indirectly bind to a cellular or viral DNA or RNA or a product thereof. In some embodiments, the cellular or viral DNA or RNA or product thereof is a genomic DNA, a coding RNA, a non-coding RNA, or a cDNA. In certain embodiments, the coding RNA is an mRNA.

In some embodiments, the probe product is a rolling circle amplification (RCA) product, a hybridization chain reaction (HCR) product, a linear oligonucleotide hybridization chain reaction (LO-HCR) product, a primer exchange reaction (PER) product, an assembly of branched structures, a hybridization complex of a plurality of fluorescently labeled probes, or any combination thereof. In some embodiments, the probe product and/or one or more nucleic acid probes comprise one or more barcode regions. In some embodiments, the nucleic acid of interest is a reporter oligonucleotide in a labelling agent comprising a binding moiety that directly or indirectly binds to a non-nucleic acid analyte. In some embodiments, the reporter oligonucleotide comprises one or more barcode regions.

In some embodiments of any of the preceding aspects, which may be combined with any of the preceding embodiments, the detectable probe is linear, circularizable, circular, or branched.

In some embodiments of any of the preceding aspects, which may be combined with any of the preceding embodiments, the tissue sample is a formalin-fixed tissue sample or a formalin-fixed paraffin-embedded (FFPE) sample. In some embodiments of any of the preceding aspects, which may be combined with any of the preceding embodiments, the autofluorescence is fixative-induced autofluorescence. In some embodiments of any of the preceding aspects, which may be combined with any of the preceding embodiments, the tissue sample is melanoma tissue, brain tissue, lung tissue, tonsil tissue, intestinal tissue, kidney tissue, spleen tissue, liver tissue, breast tissue, or liver tissue. In some embodiments, the tissue sample is brain tissue, liver tissue or tonsil tissue.

In some embodiments of any of the preceding aspects, which may be combined with any of the preceding embodiments, the endogenous biological moiety is autofluorescent. In some embodiments of any of the preceding aspects, which may be combined with any of the preceding embodiments, the endogenous biological moiety is selected from the group consisting of lipofuscin, collagen, elastin, red blood cells, flavins, nicotinamide adenine dinucleotide (NADH) and the extracellular matrix. In some embodiments, the targeting moiety comprises a hydrophobic portion for lipophilic insertion into the endogenous biological moiety. In some embodiments, the autofluorescent moiety comprises lipofuscin. In certain embodiments, the hydrophobic portion for lipophilic insertion into the endogenous biological moiety is a $C_6$-$C_{14}$ alkyl moiety, $C_6$-$C_{14}$ alkenyl moiety, terpenoid moiety, sterol moiety, or wax moiety.

In some embodiments of any of the preceding aspects, which may be combined with any of the preceding embodiments, the targeting moiety comprises a first functional group, and the endogenous biological moiety comprises a second functional group capable of reacting with the first functional group to form a covalent bond. In some embodiments, the first functional group is a carboxylic acid moiety or derivative thereof, aldehyde or ketone moiety, sulfonyl halide moiety, hydroxyl moiety, thiol moiety, amino moiety, alkenyl or dienyl moiety, epoxide moiety, or a haloalkyl moiety. In some embodiments, the first functional group is a maleimido moiety, an azido moiety, an alkynyl moiety, an N-hydroxysuccinimidyl ester moiety, or a carbonylimidazolyl moiety. In certain embodiments, the first functional group is a maleimido moiety.

In some embodiments of any of the preceding aspects, which may be combined with any of the preceding embodiments, the quencher is selected from the group consisting of:

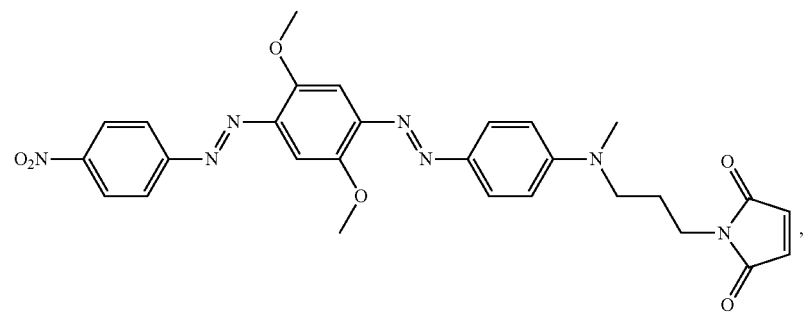
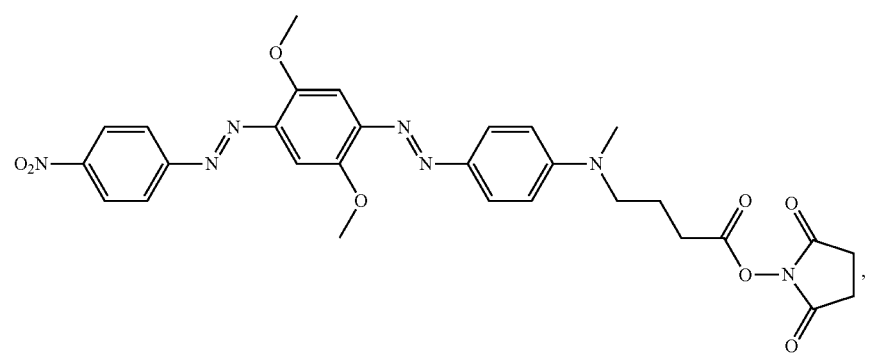
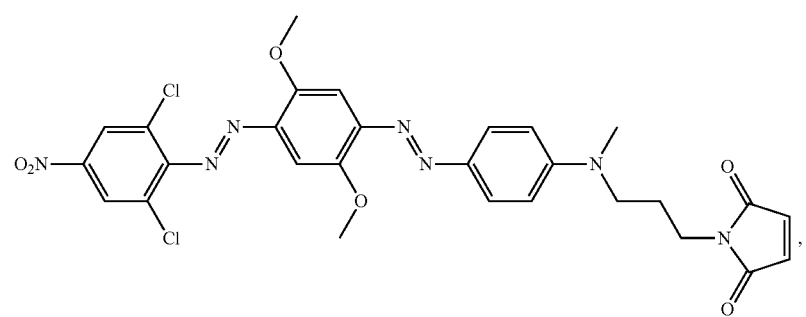
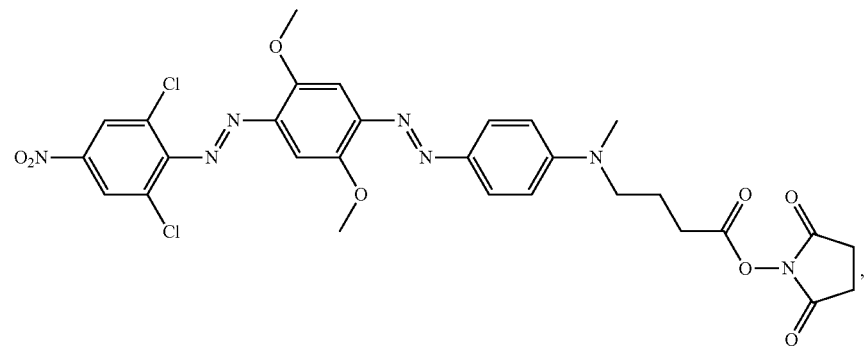
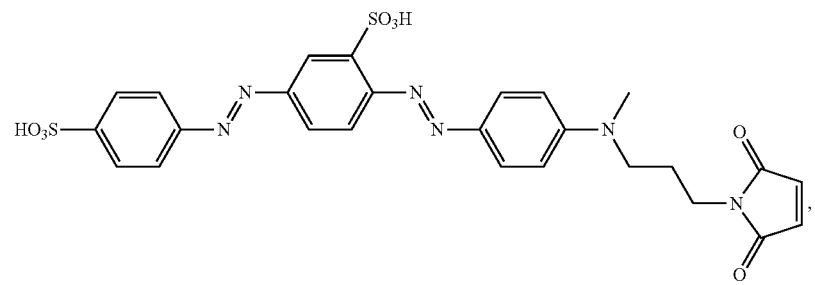

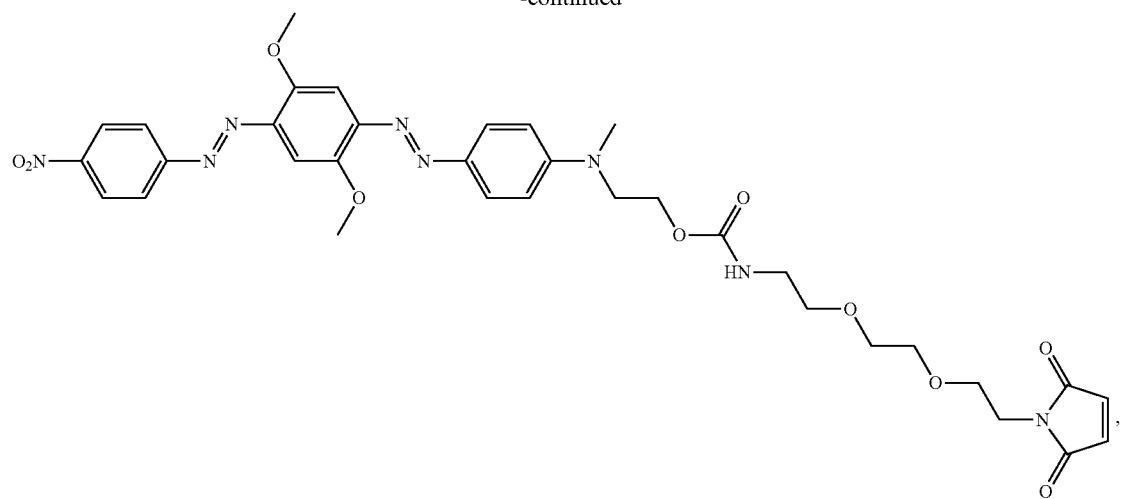
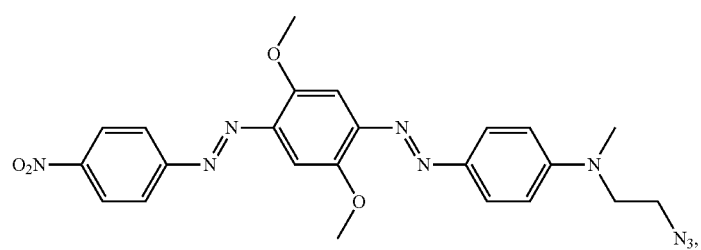
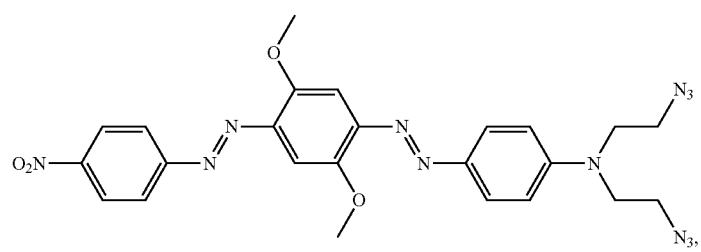
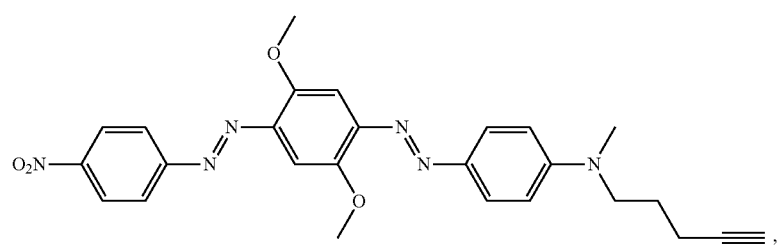
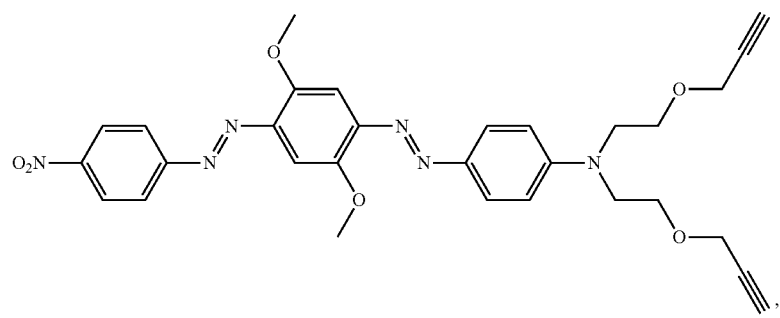

-continued
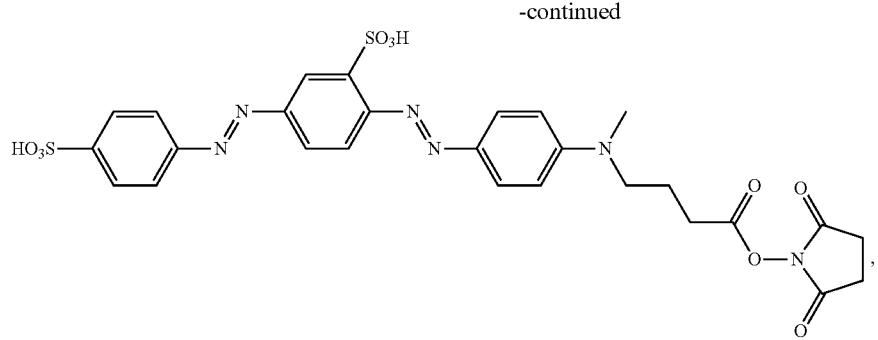
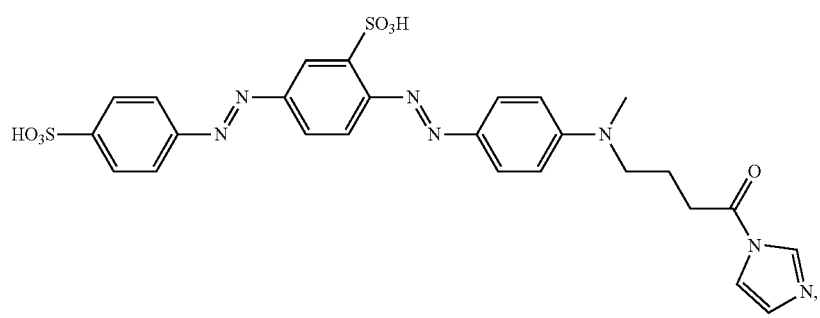
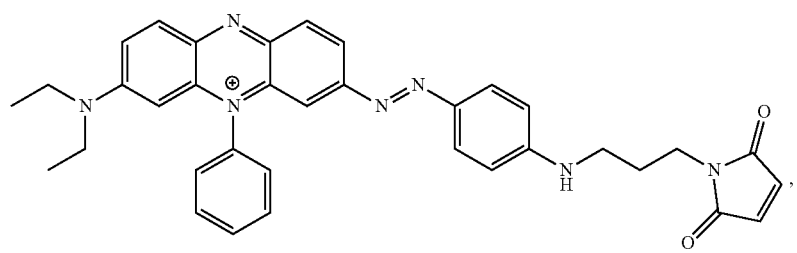
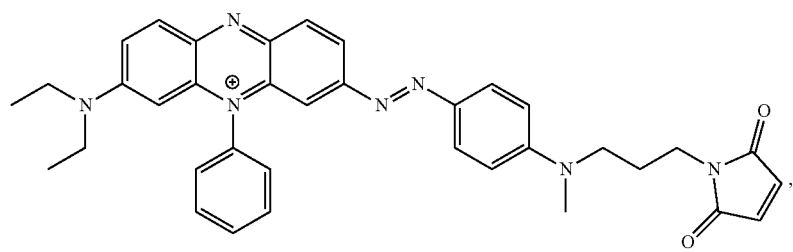
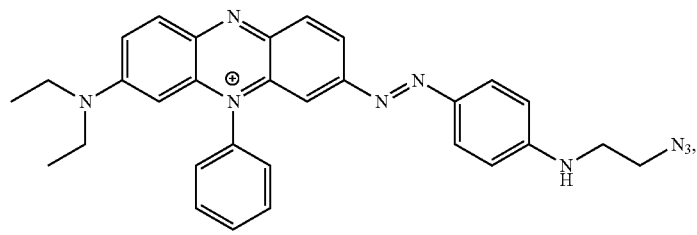
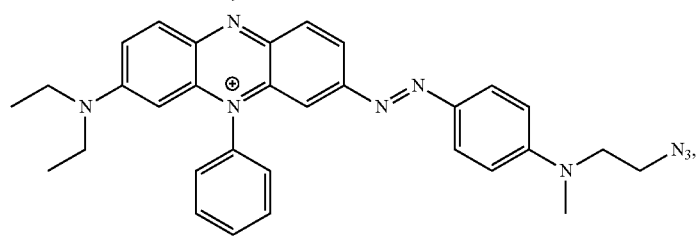

-continued
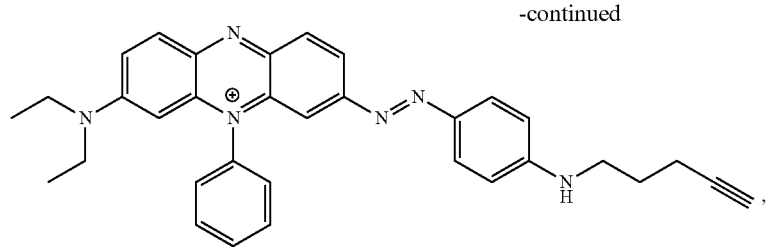,
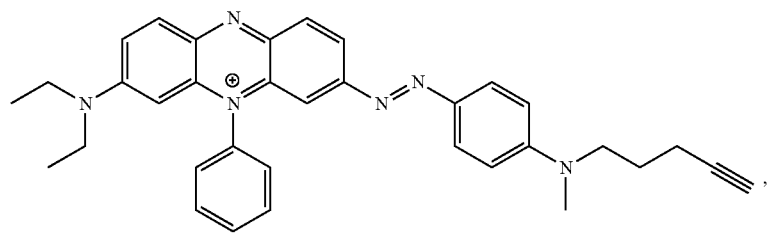,
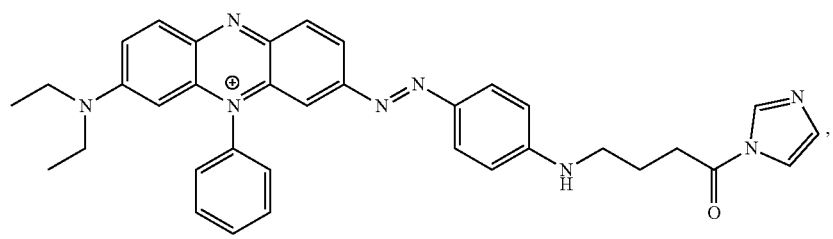,
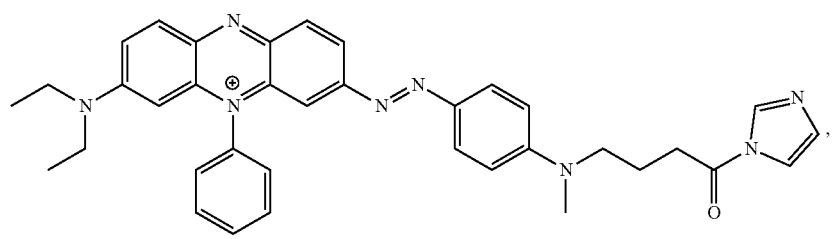,
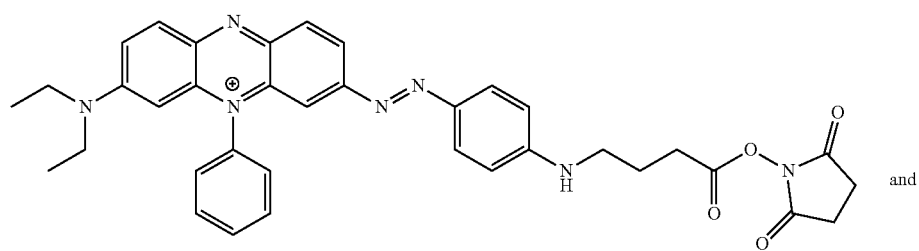 and
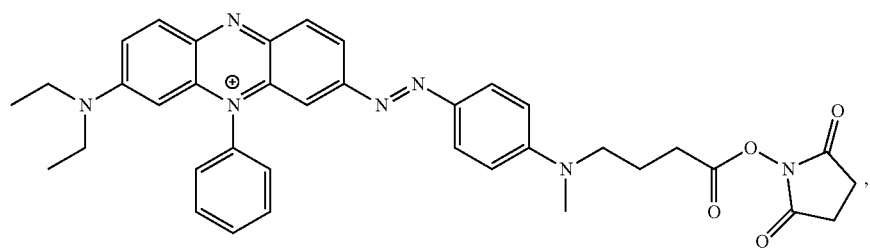, and any salt thereof. In some embodiments, the quencher is a compound selected from the group consisting of
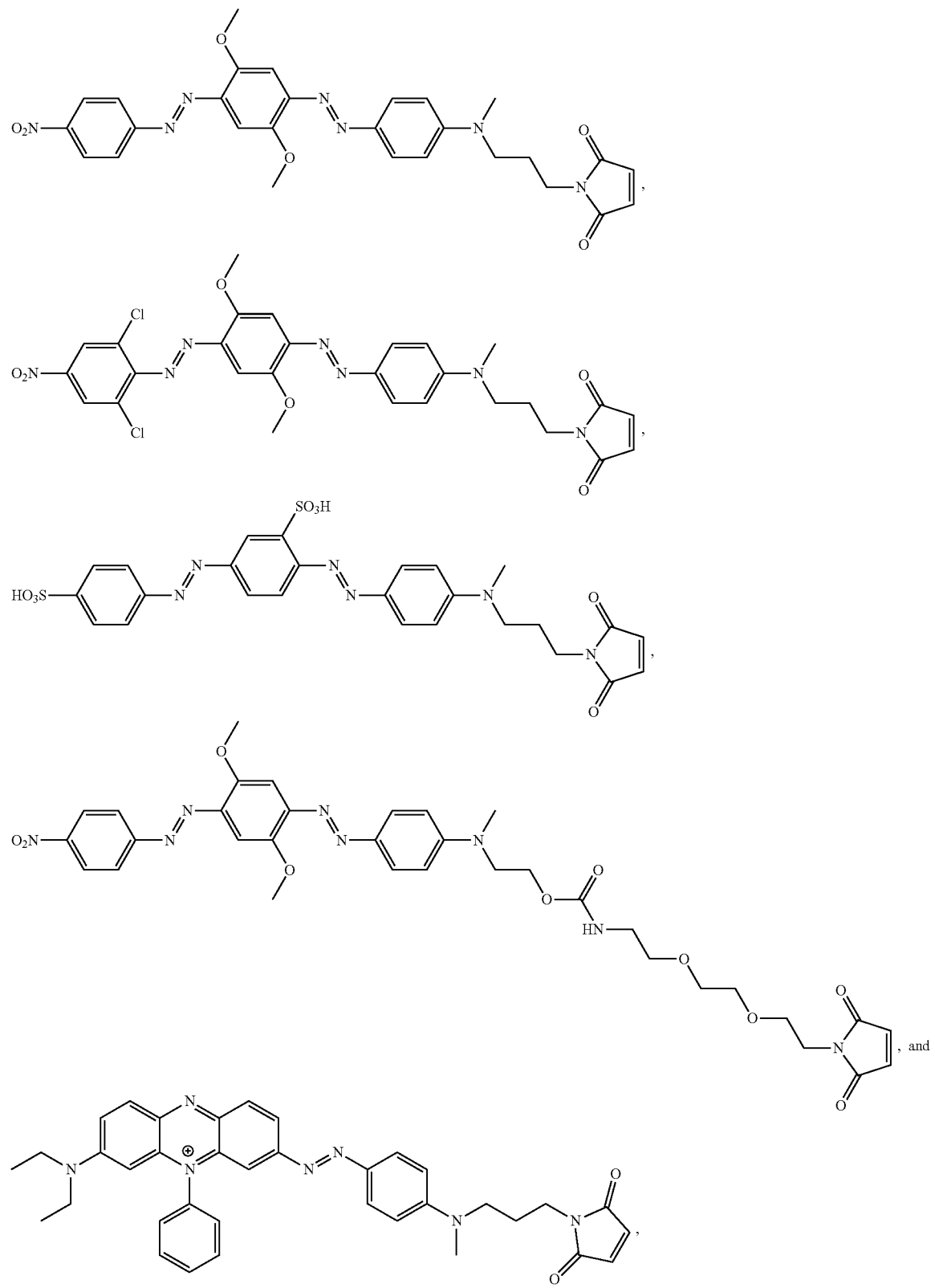
and any salt thereof.

In some embodiments of any of the preceding aspects, which may be combined with any of the preceding embodiments, the method further comprises a step of treating the biological sample or tissue sample to enrich, create and/or introduce the second functional group in the endogenous biological moiety. In some embodiments, the second functional group is thiol, and the biological sample or tissue sample is treated with a reducing agent to convert disulfide groups to thiol groups. In some embodiments, the reducing agent is dithiothreitol (DTT) or tris(2-carboxyethyl)phosphine (TCEP). In some embodiments, the first functional group is maleimide. In certain other embodiments, the endogenous biological moiety comprises a third functional group, which is different from the second functional group, and wherein the biological sample or tissue sample is treated with a heterobifunctional crosslinker comprising the second functional group and a fourth functional group capable of reacting with the third functional group to form a covalent bond, thereby introducing the second functional group in the endogenous biological moiety. In some embodiments, the third functional group is an amine and the second functional group is thiol. In some embodiments, the heterobifunctional crosslinker is succinimidyl 3-(2-pyridyldithio)propionate (SPDP) or 2,5-dioxopyrrolidin-1-yl 3-oxo-1-(pyridin-2-yldisulfaneyl)-7,10,13,16-tetraoxa-4-azanonadecan-19-oate (PEG4-SPDP).

In some embodiments of any of the preceding aspects, which may be combined with any of the preceding embodiments, the step of detecting a signal associated with the detectable probe bound to the molecule of interest comprises imaging at one or more wavelengths between about 400 nm and about 700 nm. In some embodiments, the one or more wavelengths are selected from the group consisting of 488 nm, 532 nm, 561 nm, 590 nm, 640 nm, and 647 nm. In some embodiments of any of the preceding aspects, which may be combined with any of the preceding embodiments, the quencher is provided in DMSO solution at a concentration of between about 0.01 mM and about 0.8 mM.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings illustrate certain embodiments of the features and advantages of this disclosure. These embodiments are not intended to limit the scope of the appended claims in any manner.

FIGS. 3A-3D depict in situ imaging of fresh frozen mouse brain tissues before and after targeted quenching using quencher Compound 1A. FIGS. 3A-3B depict the detected fluorescence in mouse brain dentate gyrus (DG) section, and FIGS. 3C-3D depict the detected fluorescence in a mouse brain cortex section. FIGS. 3A and 3C show fluorescence in unquenched mouse brain tissue sections; FIGS. 3B and 3D depict fluorescence in mouse brain tissue sections subjected to stripping of fluorescently labeled probes, treated with quencher comprising a targeting moiety, and rehybridized with additional fluorescently labeled probes. The autofluorescence quenching effect was retained after stripping.

FIGS. 4A-4C depict in situ imaging of an FFPE human brain tissue after detectable probe hybridization (before quenching), post quenching with Compound 1A comprising a targeting moiety, and after stripping of fluorescently labeled probes and rehybridization of additional fluorescently labeled probes. The autofluorescence quenching effect was retained after stripping.

FIGS. 6A, 6B, 6C, and 6D depict the quantitation of detected object local signal-to-noise ratio using ATTO 488, ATTO 532, ATTO 590, and ATTO 647 fluorescent dye labeled detectable probes, respectively. The signal-to-noise ratio was maintained after a single quenching application, even after 5 cycles of stripping and rehybridization with fluorescent probes.

FIGS. 7A, 7B, 7C, and 7D depict the quantitation of background signals.

FIGS. 8A, 8B, and 8C depict the detected object local signal-to-noise ratio (mean) using ATTO 532, ATTO 590, and ATTO 647 fluorescent dye labeled detectable probes, respectively.

FIG. 9A depicts the background signals in detection of RPLP0 in tonsil tissues, after quenching (cycle 5) as compared to before quenching (cycle 1). FIG. 9B depicts the comparison of post-quenching background signals (cycle 6) to pre-quenching background signals (cycle 2) in detection of GAPDH in tonsil tissues. FIG. 9C depicts the comparison of post-quenching background signals (cycle 7) to pre-quenching background signals (cycle 3) in detection of ACTB in tonsil tissues. Significant reduction of background signal was observed across all the quencher concentrations tested and over multiple cycles of stripping and re-probing, as compared to the unquenched tonsil tissues.

DETAILED DESCRIPTION

Figure 1:
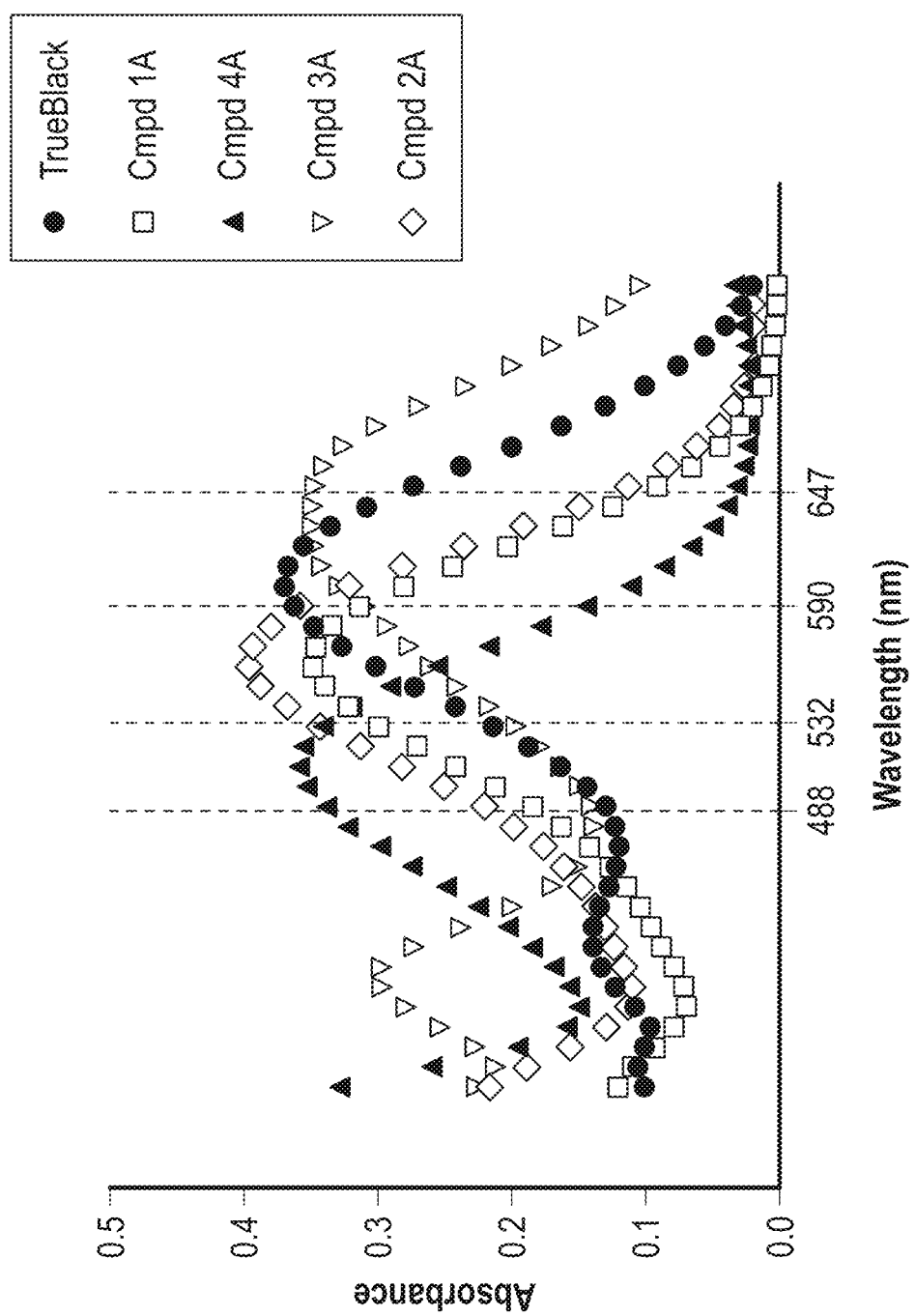
FIG. 1 shows UV-visible absorption spectra for exemplary quenchers of the present disclosure compared to the absorption spectrum of a TrueBlack® quencher dye.

The present disclosure relates to methods for masking or reducing autofluorescence in biological samples. More specifically, the present disclosure relates to methods and compositions for in situ analysis or detection of analytes in a sample, and compounds for the same.

Analysis of biological samples by fluorescence in situ hybridization hinges upon the ability to produce and detect fluorescence signals associated with analytes of interest or probes specific to those analytes of interest. Importantly, these analytes or the probes thereof should be distinguishable from and have a brighter fluorescence signal as compared to other non-analytes that may be autofluorescent and contribute to background noise. Tissue autofluorescence—which can be associated with various endogenous biological moieties including but not limited to lipofuscin, collagen, elastin, red blood cells, flavins, nicotinamide adenine dinucleotide (NADH), and even the extracellular matrix—is generally observed in most tissue types. Such autofluorescence also exhibits a broad color emission, such that fluorescence signals associated with analytes of interest may be obscured across the visible light region of the electromagnetic spectrum—the primary band of wavelengths evaluated in in situ fluorescence imaging. As a result, certain wavelengths cannot be read without auxiliary treatments to reduce fluorescence.

In order to reduce autofluorescence, various commercial quencher compounds and compositions have been developed for application to biological samples. Existing commercially available quenchers for reducing autofluorescence are combined in quenching mixtures specifically tailored to certain tissues and/or types of autofluorescence. However, quenching efficiency often depends upon the quencher compound being utilized and the tissue type being analyzed. Indeed, no single universal quencher exists for all tissue types. Even under circumstances where background autofluorescence is substantially reduced, the occurrence of even minor occurrences of unwanted fluorescence may be detrimental to the detection of actual fluorescence signals. For example, punctuate background fluorescence signals may appear similar in size and shape to the fluorescence signals expected from rolling circle amplification products. Due to the similar size and shape of background autofluorescence to actual fluorescent signals, failure to reduce autofluorescence sufficiently may lead to higher readings of false positives.

An additional disadvantage of commercially available quenchers is that they are only weakly physically adsorbed onto tissue samples when they are applied. As such, existing quenchers not only require high concentrations to reduce background fluorescence to provide sufficient quenching but are also easily washed away with standard stripping agents typically used for fluorescence imaging across multiple cycles of hybridization and detection. Consequently, commercially available quenchers are applied and re-applied to a single tissue sample with each cycle of hybridization and imaging. The repeated treatments add significant burden to the analysis of a given tissue sample—lengthening assay time, increasing reagent expenditures and necessitating a certain level of complexity for automated sequencing equipment to accommodate the additional step of re-applying quenchers between imaging cycles.

Thus, there is an ongoing need for improved compounds and methods for reducing autofluorescence and analyzing tissue samples or other biological samples with multiplexed (multicolor) and reiterative (multiple cycle) fluorescence imaging techniques.

The section headings used herein are for organizational purposes only and are not to be construed as limiting the subject matter described.

The following description sets forth exemplary methods, parameters and the like. It should be recognized, however, that such description is not intended as a limitation on the scope of the present disclosure but is instead provided as a description of exemplary embodiments.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

I. Overview

The present disclosure addresses these needs for improved methods for multicolor, multi-cycle fluorescence imaging by providing methods of reducing autofluorescence and analyzing biological and/or tissue samples. The methods of the present disclosure achieve long-lasting reductions of background autofluorescence over multiple cycles of imaging by employing quencher compounds that combine broad visible spectrum absorption with durable targeting chemistries.

The absorptive dye moieties of the quenching compounds utilized herein are capable of broad spectrum visible light absorption from 400-700 nm, particularly in the range of 500-600 nm, which is a primary region of fluorescence imaging as well as a region of high background autofluorescence. However, the absorption spectrum of the quencher dye may be readily shifted, and the solubility easily adjusted, via synthetic modifications of the substituents and linker groups as required for specific applications.

The targeting moieties of the quenchers are targeted to functional groups native to tissue samples, particularly those present on endogenous biological moieties or autofluorescent moieties. The targeting moieties of the quenchers form durable chemical or physical interactions with these autofluorescent endogenous biological moieties by covalent chemical bonds or by energetically favorable intermolecular attraction in close proximity. As the functional groups present on certain endogenous biological moieties may differ, the targeting moieties of the quenchers may be selected or combined with other quenchers to provide optimal targeting to the autofluorescent entities in the samples. The application of the quenchers may also be combined with pre-treatment steps to enrich the presence of functional groups in the biological samples that can bind to the quencher targeting moieties.

The quenching can be carried out in a single step on a benchtop prior to the first cycle of imaging. Once reacted with or bound to the endogenous biological moieties via the targeting moieties, the quenchers remain intact in the biological sample or tissue sample. The samples treated with quenchers as provided in the present disclosure may undergo subsequent, repeated treatments with washing and stripping buffers in order to remove and introduce different detectable probes for imaging, without substantial loss of the quenchers and with little to no increase in background autofluorescence. The combination of the durable targeting moieties and broadband quencher dyes work in a single application step to reduce autofluorescence across a broad spectrum and over multiple cycles of imaging without the need for additional quenching steps.

Elimination of the need for repeated application of quenchers to a given biological sample has significant implications for the cost and speed of multiplexed, multi-cycle in situ analysis. For example, fluorescence imaging can be conducted with less quenching reagent as well as with reduced sample preparation time and less downtime for each imaging cycle, when performed on a sample treated with a quencher comprising a quencher dye and a targeting moiety. Furthermore, as additional quenching steps are no longer required, the device or instrument for performing the assay may no longer need to accommodate quenching steps as part of each cycle program or in their engineering configurations. Where repeated quenching steps previously may have precluded such measurements from be conducted on lower cost, simpler devices, the same devices can now can be utilized to perform multi-cycle, multiplexed imaging analyses. Thus, the methods and compounds of the present disclosure enable more efficient, more cost-effective fluorescence in situ hybridization imaging.

A. Methods (i) Method for Reducing Autofluorescence

In one aspect, provided herein are methods for reducing autofluorescence in a biological sample, comprising contacting the biological sample with a quencher comprising a quencher dye and a targeting moiety, where the targeting moiety reacts with a biological moiety endogenous to the biological sample, thereby targeting the quencher to the endogenous biological moiety; and detecting a signal associated with a detectable probe directly or indirectly bound to a molecule of interest in the biological sample, wherein the quencher reduces autofluorescence in the biological sample. In some embodiments, the biological sample is a tissue sample. In some embodiments, the biological sample is contacted with a plurality of detectable probes each directly or indirectly bound to a molecule of interest in the biological sample, and signals associated with the plurality of detectable probes are detected at locations in the biological sample.

In some embodiments, the biological sample is contacted with the detectable probe prior to being contacted with the quencher. In other embodiments, the biological sample is contacted with the detectable probe after being contacted with the quencher. In yet other embodiments, the biological sample is contacted with the detectable probe and the quencher simultaneously.

In one aspect, provided herein are methods for reducing autofluorescence in a biological sample, comprising: contacting the biological sample with a quencher comprising a quencher dye and a targeting moiety, where the targeting moiety reacts with a biological moiety endogenous to the biological sample, thereby targeting the quencher to the endogenous biological moiety; contacting the biological sample with a detectable probe that directly or indirectly binds to a molecule of interest in the biological sample; and detecting a signal associated with the detectable probe directly or indirectly bound to the molecule of interest in the biological sample, wherein the quencher reduces autofluorescence in the biological sample.

In one aspect, provided herein are methods for reducing autofluorescence in a biological sample, comprising: contacting the biological sample with a detectable probe that directly or indirectly binds to a molecule of interest in the biological sample; optionally detecting a signal associated with the detectable probe at a location in the biological sample; contacting the biological sample with a quencher comprising a quencher dye and a targeting moiety, where the targeting moiety reacts with a biological moiety endogenous to the biological sample, thereby targeting the quencher to the endogenous biological moiety; and detecting a signal associated with the detectable probe directly or indirectly bound to the molecule of interest in the biological sample, wherein the quencher reduces autofluorescence in the biological sample.

In one aspect, provided herein are methods for reducing autofluorescence in a biological sample, comprising: contacting the biological sample with a detectable probe that directly or indirectly binds to a molecule of interest in the biological sample; optionally detecting a signal associated with the detectable probe at a location in the biological sample; contacting the biological sample with a quencher comprising a quencher dye and a targeting moiety, where the targeting moiety reacts with a biological moiety endogenous to the biological sample, thereby targeting the quencher to the endogenous biological moiety; detecting a signal associated with the detectable probe directly or indirectly bound to the molecule of interest in the biological sample; removing the detectable probe and/or extinguishing the signal associated therewith; contacting the biological sample with an additional detectable probe that directly or indirectly binds to an additional molecule of interest in the biological sample; and detecting a signal associated with the additional detectable probe directly or indirectly bound to the additional molecule of interest in the biological sample, wherein the quencher reduces autofluorescence in the biological sample. The molecule of interest and the additional molecule of interest can be the same or different, and the detectable probe and the additional detectable probe can be the same or different. In some embodiments, the signal associated with the additional detectable probe is detected without contacting the biological sample with a quencher after contacting with the quencher comprising the quencher dye and the targeting moiety. In some embodiments, removing the detectable probe from the biological sample is performed by stripping, for instance, by washing the sample in a solution comprising a denaturing agent and/or under a denaturing condition (e.g., heating).

In one aspect, provided herein are methods for reducing autofluorescence in a biological sample, comprising: contacting the biological sample with a nucleic acid probe or probe set that directly or indirectly binds to a molecule of interest in the biological sample; contacting the biological sample with a quencher comprising a quencher dye and a targeting moiety, where the targeting moiety reacts with a biological moiety endogenous to the biological sample, thereby targeting the quencher to the endogenous biological moiety; contacting the biological sample with a labeling agent (e.g., a nucleic acid-tagged binder such as a DNA-tagged antibody against a protein analyte) that directly or indirectly binds to an additional molecule of interest in the biological sample; and detecting signals associated with the labeling agent and the nucleic acid probe or probe set at one or more locations in the biological sample, wherein the quencher reduces autofluorescence in the biological sample. In some embodiments, the nucleic acid probe or probe set is a circular probe or circularizable probe or probe set that hybridizes to a nucleic acid in the biological sample, and a product (e.g., RCA product) of the circular probe or circularizable probe or probe set is generated in the biological sample. In some embodiments, the biological sample is contacted with detectably labeled nucleic acid probes that hybridize to the RCA product, prior to contacting the biological sample with the quencher. In some embodiments, the biological sample is contacted with intermediate nucleic acid probes that hybridize to the RCA product and detectably labeled nucleic acid probes that hybridize to the intermediate nucleic acid probes, prior to contacting the biological sample with the quencher. In some embodiments, detecting signals associated with the nucleic acid probe or probe set comprises detecting signals associated with the detectably labeled nucleic acid probes; while the biological sample can be contacted with the detectably labeled nucleic acid probes prior to contacting the quencher and the labeling agent, the detectably labeled nucleic acid probes can be detected after the quenching and contacting with the labeling agent (e.g., DNA-tagged antibody staining of the sample).

In another aspect, provided herein are methods for reducing autofluorescence in a biological sample, comprising: contacting the biological sample with a nucleic acid probe or probe set that directly or indirectly binds to a molecule of interest in the biological sample; contacting the biological sample with a labeling agent (e.g., a nucleic acid-tagged binder such as a DNA-tagged antibody) that directly or indirectly binds to an additional molecule of interest in the biological sample; contacting the biological sample with a quencher comprising a quencher dye and a targeting moiety, where the targeting moiety reacts with a biological moiety endogenous to the biological sample, thereby targeting the quencher to the endogenous biological moiety; and detecting signals associated with the labeling agents and the nucleic acid probe or probe set at one or more locations in the biological sample, wherein the quencher reduces autofluorescence in the biological sample. In some embodiments, the nucleic acid probe or probe set is a circular probe or circularizable probe or probe set that hybridizes to a nucleic acid in the biological sample, and a product (e.g., RCA product) of the circular probe or circularizable probe or probe set is generated in the biological sample. In some embodiments, the biological sample is contacted with detectably labeled nucleic acid probes that hybridize to the RCA product, prior to contacting the biological sample with the labeling agent. In some embodiments, the biological sample is contacted with intermediate nucleic acid probes that hybridize to the RCA product and detectably labeled nucleic acid probes that hybridize to the intermediate nucleic acid probes, prior to contacting the biological sample with the labeling agent. In some embodiments, detecting signals associated with the nucleic acid probe or probe set comprises detecting signals associated with the detectably labeled nucleic acid probes; while the biological sample can be contacted with the detectably labeled nucleic acid probes prior to contacting the labeling agent and the quencher, the detectably labeled nucleic acid probes can be detected after contacting with the labeling agent (e.g., DNA-tagged antibody staining of the sample) and the quenching.

In yet another aspect, provided herein are methods for reducing autofluorescence in a biological sample, comprising: contacting the biological sample with a nucleic acid probe or probe set that directly or indirectly binds to a molecule of interest in the biological sample; bleaching the biological sample; contacting the biological sample with a labeling agent (e.g., a nucleic acid-tagged binder such as a DNA-tagged antibody) that directly or indirectly binds to an additional molecule of interest in the biological sample; contacting the biological sample with a quencher comprising a quencher dye and a targeting moiety, where the targeting moiety reacts with a biological moiety endogenous to the biological sample, thereby targeting the quencher to the endogenous biological moiety; and detecting signals associated with the labeling agents and the nucleic acid probe or probe set at one or more locations in the biological sample, wherein the quencher reduces autofluorescence in the biological sample. In some embodiments, bleaching the biological sample comprises photochemical bleaching using a chemical agent and a light source. In some embodiments, bleaching the biological sample comprises contacting the biological sample with a chemical (e.g., 1% hydrogen peroxide) and exposing the biological sample to intense visible light (e.g., light of wavelength 455 nm for 5 mins). Exemplary photochemical bleaching techniques are disclosed in Section I-A. In some embodiments, the nucleic acid probe or probe set is a circular probe or circularizable probe or probe set that hybridizes to a nucleic acid in the biological sample, and a product (e.g., RCA product) of the circular probe or circularizable probe or probe set is generated in the biological sample. In some embodiments, the biological sample is contacted with detectably labeled nucleic acid probes that hybridize to the RCA product, prior to bleaching the biological sample (e.g., using photochemical bleaching). In some embodiments, the biological sample is contacted with intermediate nucleic acid probes that hybridize to the RCA product and detectably labeled nucleic acid probes that hybridize to the intermediate nucleic acid probes, prior to bleaching the biological sample (e.g., using photochemical bleaching). In some embodiments, detecting signals associated with the nucleic acid probe or probe set comprises detecting signals associated with the detectably labeled nucleic acid probes; while the biological sample can be contacted with the detectably labeled nucleic acid probes prior to bleaching the biological sample (e.g., using photochemical bleaching), the detectably labeled nucleic acid probes can be detected after the bleaching, the contacting with the labeling agent (e.g., DNA-tagged antibody staining of the sample), and the quenching.

In some embodiments, prior to detecting a signal associated with a detectable probe, the method comprises contacting the biological sample with a primary probe, such as a nucleic acid probe, that directly or indirectly binds to the molecule of interest in the biological sample, and the detectable probe binds directly or indirectly to the primary probe. In some embodiments, the method further comprises removing the detectable probe or a portion thereof from the biological sample, wherein the quencher remains in the biological sample, optionally wherein the removing step comprises treating the biological sample with a denaturing agent and/or heating. In some embodiments, the denaturing agent comprises dimethyl sulfoxide (DMSO), formamide, and/or an alkaline solution.

Additional sample processing steps may be included or omitted in the methods as described herein. For example, in some embodiments, the methods of the present disclosure comprise staining the biological sample. In some embodiments, which may be combined with the preceding embodiments, the methods further comprise fixing the biological sample. In some embodiments, which may be combined with the preceding embodiments, the methods further comprise de-crosslinking the biological sample. In some embodiments, the step of contacting the biological sample with the quencher may be carried out before or after one or more treatments for fixing, permeabilizing/de-crosslinking, and/or staining the biological sample.

In another aspect, provided herein are methods for reducing autofluorescence, comprising contacting a tissue sample with a quencher comprising a quencher dye and a targeting moiety, where the targeting moiety reacts with a biological moiety endogenous in the tissue sample, thereby targeting the quencher to the endogenous biological moiety; and detecting a signal associated with a detectable probe directly or indirectly bound to a molecule of interest in the tissue sample, wherein the quencher reduces autofluorescence in the tissue sample.

In some embodiments, the tissue sample is contacted with the detectable probe prior to being contacted with the quencher. In other embodiments, the tissue sample is contacted with the detectable probe after being contacted with the quencher. In yet other embodiments, the tissue sample is contacted with the detectable probe and the quencher simultaneously.

In some embodiments, prior to detecting a signal associated with a detectable probe, the method comprises contacting the tissue sample with a primary probe, such as a nucleic acid probe, that directly or indirectly binds to the molecule of interest in the tissue sample, and wherein the detectable probe binds directly or indirectly to the primary probe. In some embodiments, the method further comprises removing the detectable probe or a portion thereof from the tissue sample, wherein the quencher remains in the tissue sample, optionally wherein the removing step comprises treating the tissue sample with a denaturing agent and/or heating. In some embodiments, the denaturing agent comprises dimethyl sulfoxide (DMSO), formamide, and/or an alkaline solution.

It should be recognized that the order of contacting the biological or tissue sample with the quencher and the detectable probes may be adjusted to accommodate one or more additional sample processing steps as desired. Depending upon the class of analytes to be evaluated, certain sample processing steps may be included or omitted and the order of reagent application may change. For example, in analyses involving proteins as molecules of interest and protein-related sample processing steps, the quencher is preferably added after fixation, permeabilization/de-crosslinking, and staining to achieve better protein stability and signal downstream but prior to introduction of any detectable probes to the sample. In analyses involving only nucleic acids as molecules of interest and nucleic acid-related processing steps, such as in RNA workflows, the quencher is preferably added after application of primary probes to the sample, but may be added either before or after any amplification step, such as rolling circle amplification.

In some embodiments, the method for reducing autofluorescence comprises bleaching (e.g., chemical bleaching, photobleaching, photochemical bleaching, exposure to heat) the sample prior to, simultaneously, or after being contacted with a quencher disclosed herein. In some embodiments, the combination of bleaching and quenching prior to signal detection increases signal-to-noise ratios and detectable object count density as compared to an unbleached and/or unquenched tissue sample.

Unbleached biological sample or unbleached tissue sample is understood to be a biological sample or tissue sample of the same type having undergone identical treatments as the bleached sample excepting treatment with the bleaching agent (e.g., chemical reagent in chemical bleaching, light in photobleaching, chemical and light in photochemical bleaching, heat, and/or enzyme), as described herein.

In some embodiments, the method for reducing autofluorescence comprises chemical bleaching. In some embodiments, the sample is treated with a chemical (e.g., hydrogen peroxide, sodium borohydride, Trypan blue, eriochrome black T, ammonium chloride, copper sulfate, Sudan black or comparable chromophores). Any suitable chemicals or dyes can be used for chemical bleaching a tissue sample.

Some tissues can have high endogenous enzymes (e.g., high endogenous peroxidase, phosphatase) resulting in high background. In some embodiments, the sample is treated with a chemical to block enzyme activity (e.g., hydrogen peroxide, acetic acid, potassium borohydride). Any suitable chemical to block background resulting from high endogenous enzyme activity can be used.

In some embodiments, the method for reducing autofluorescence comprises enzymatic bleaching. In one aspect, enzymatic bleaching may comprise hydrolytic enzymes. In one aspect, enzymatic bleaching may comprise enzymes targeting endogenous biological moieties such as those described in Section I-C.

In some embodiments, the method for reducing autofluorescence comprises photobleaching. In some embodiments, the sample is exposed to an intense visible light source. In some aspects, the intense visible light source can be a fluorescent light, incandescent ultra-violet bulb, light-emitting diode (LED) lamps with broad-spectrum emission of white phosphor, LED lamps with blue and red emission peaks or LED arrays. Any suitable light source can be used for photobleaching a tissue sample.

In some embodiments, the method for reducing autofluorescence comprises exposing the sample to heat. In some embodiments, the sample is exposed to heat.

In some embodiments, the method for reducing autofluorescence comprises photochemical bleaching. In some embodiments, the sample is treated with a chemical and exposed to an intense visible light source, simultaneously or in any order thereof. For example, the tissue sample is bleached by exposure to a solution comprising methanol, ethanol or octanol and DMSO and an agent such a potassium hydroxide, bleach, or hydrogen peroxide. In one embodiment, 1% hydrogen peroxide is used. In another embodiment, a mixture of methanol and DMSO and 30% hydrogen peroxide is used. In some embodiments, a tissue sample is photobleached with 1% hydrogen peroxide and exposed to light of wavelength 455 nm for 5 minutes. In some embodiments, the intense visible light source is a fluorescent light, incandescent ultra-violet bulb, light-emitting diode (LED) lamps with broad-spectrum emission of white phosphor, LED lamps with blue and red emission peaks, LED arrays, sunlight or any suitable light source. In some embodiments, the tissue sample is exposed to light between about 400 nm to 700 nm. In some embodiments, the photobleaching is performed in the presence of a quencher (e.g., between about 0.1 nM and about 0.1 mM of quencher dye). In some embodiments, the sample is exposed to light, such as between 365 nm and 525 nm wavelength of light. In some embodiments, the sample is exposed to light of about 365 nm, about 375 nm, about 385 nm, about 395 nm, about 405 nm, about 415 nm, about 425 nm, about 430 nm, about 435 nm, about 445 nm, about 455 nm, about 465 nm, about 475 nm, about 485 nm, about 495 nm, about 505 nm, about 515 nm, about 525 nm, or any wavelength between the foregoing. In some embodiments, the sample is exposed to light, such as between 100 watts and 200 watts. In some embodiments, the sample is exposed to light of about 100 watts, 110 watts, 120 watts, 130 watts, 140 watts, 150 watts, 160 watts, 170 watts, 180 watts, 200 watts, or between any of the foregoing. In some embodiments, the sample is photobleached for about 2 minutes, about 3 minutes, about 4 minutes, about 5 minutes, about 6 minutes, about 7 minutes, about 8 minutes, or between any of the foregoing. In some embodiments, the sample is photobleached for about 2 minutes, about 5 minutes, or about 8 minutes. In some embodiments, concentration of hydrogen peroxide used is about 1%, about 1.5%, about 2%, about 2.5%, about 3%, about 3.5%, about 4%, or between any of the foregoing. In some embodiments, a tissue sample is treated with a combination of a 0.1 mM quencher, 1% hydrogen peroxide, and exposed to light of wavelength 455 nm (high power) for 5 minutes, in any order thereof. In some embodiments, for photochemical bleaching, a tissue sample is treated with between about 1% and about 4% hydrogen peroxide, and exposed to light of wavelength between about 365 nm and about 525 nm for about 2, about 5, and about 8 minutes and at a power between about 100 W and about 200 W. In some embodiments, for photochemical bleaching, a tissue sample is treated with about 1% hydrogen peroxide, and exposed to light of wavelength of about 455 nm for about 5 minutes and at a high power, such as between about 150 W and about 200 W. The photochemical bleaching can be performed prior to, during, and/or after contacting the sample with a quencher disclosed herein.

In some embodiments, the method for reducing autofluorescence comprises any combination of the foregoing. In some embodiments, the method further comprises bleaching the biological sample or tissue sample with a chemical reagent, an enzyme, light, heat, or any combination thereof, prior to, simultaneously, or after the contacting the biological sample or tissue sample with the quencher.

In some embodiments, the bleaching is performed for at least 1, at least 2, at least 3, at least 4, at least, 5, at least 6 cycles of bleaching (e.g., photochemical bleaching). In some embodiments, each cycle is performed for about 1 min, about 2 minutes, 5 minutes, 10 minutes, 20 minutes, 30 minutes, 40 minutes, 50 minutes, 60 minutes, or any time between the foregoing. In some embodiments, a sample is treated with an agent (e.g., hydrogen peroxide) and photochemical bleaching is performed for about no more than 1 min, no more than 2 minutes, no more than 5 minutes, no more than 8 minutes, or no more than 10 minutes. In certain embodiments, the autofluorescence is reduced by at least about 50%, at least about 60%, at least about 70% or at least about 80% as compared to an unquenched and/or unbleached tissue sample. In any embodiment herein, photochemical bleaching methods are compatible with methods of analyzing biological samples (e.g., tissue sample) as described herein. Additional methods and aspects of bleaching tissue samples are described for example in Du et al., *Nature Protocols* 14(10):2900-2930, 2019, U.S. Pat. No. 6,232,092, Meeker A. K., Photochemical pre-bleaching of formalin-fixed archival prostate tissues significantly reduces autofluorescence to facilitate multiplex immunofluorescence staining, bioRxiv doi: 10.1101/2021.11.09.467916, all the contents of which are incorporated herein by reference in their entireties. In any of the preceding embodiments, the methods for reducing autofluorescence may be performed using a buffer comprising a crowding agent. In some embodiments, the crowding agent is selected from the group consisting of poly(ethylene glycol) (PEG), glycerol, Ficoll®, and dextran sulfate. In any of the preceding embodiments, the crowding agent can be poly(ethylene glycol) (PEG). In some embodiments, the crowding agent comprises PEG having an average molecular weight between about 200 Da and about 35,000 Da. In some embodiments, the PEG has an average molecular weight between about 2000 Da and about 16,000 Da. In some embodiments, the PEG is PEG 200, PEG 2000, PEG 3000, PEG 4000, PEG 5000, PEG 6000, PEG 7000, PEG 8000, PEG 9000, PEG 10000, PEG 11000, PEG 12000, PEG 13000, PEG 14000, PEG 15000, PEG 16000, PEG 30000, PEG 35000, or PEG 40000. In any of the preceding embodiments, the PEG can be selected from the group consisting of PEG200, PEG8000, and PEG35000.

In some embodiments, the PEG is present at a concentration between about 2% to 25%, from about 4% to about 23%, from about 6% to about 21%, or from about 8% to about 20% (v/v). In any of the preceding embodiments, the buffer may comprise between about 5% and about 15% PEG (v/v), optionally wherein the buffer comprises about 10% PEG (v/v).

(ii) Method for Analyzing a Biological Sample

In another aspect, provided herein are methods for analyzing a biological sample, comprising contacting the biological sample with a quencher comprising a quencher dye and a targeting moiety, wherein the targeting moiety directly or indirectly binds and/or reacts with a biological moiety endogenous to the biological sample, thereby targeting the quencher to the biological moiety; contacting the biological sample with a detectable probe that directly or indirectly binds to a molecule of interest in the biological sample; and detecting a signal associated with the detectable probe bound to the molecule of interest in the biological sample, wherein the quencher dye reduces autofluorescence of the biological sample, thereby detecting the molecule of interest in the biological sample.

In some embodiments, the biological sample is contacted with the detectable probe prior to being contacted with the quencher. In other embodiments, the biological sample is contacted with the detectable probe after being contacted with the quencher. In yet other embodiments, the biological sample is contacted with the detectable probe and the quencher simultaneously.

In some embodiments, prior to contacting the biological sample with a detectable probe that directly or indirectly binds to a molecule of interest in the biological sample, the method comprises contacting the biological sample with a nucleic acid probe that directly or indirectly binds to the molecule of interest in the biological sample, and wherein the detectable probe binds directly or indirectly to the nucleic acid probe. In some embodiments, the method further comprises removing the detectable probe or a portion thereof from the biological sample, wherein the quencher remains in the biological sample, optionally wherein the removing step comprises treating the biological sample with a denaturing agent and/or heating.

Additional sample processing steps may be included or omitted in the methods as described herein. For example, in some embodiments, the methods of the present disclosure comprise staining the biological sample. In some embodiments, which may be combined with the preceding embodiment, the methods further comprise fixing the biological sample. In some embodiments, which may be combined with the preceding embodiments, the methods further comprise de-crosslinking the biological sample. In some embodiments, the step of contacting the biological sample with the quencher may be carried out before or after one or more treatments for staining, permeabilizing, fixing and/or de-crosslinking the biological sample.

In some embodiments wherein the biological sample is a tissue sample, similar treatments and orders of applying the quencher and detectable probes may be taken. For example, in some embodiments, the methods of the present disclosure comprise staining the tissue sample. In some embodiments, which may be combined with the preceding embodiment, the methods further comprise fixing the tissue sample. In some embodiments, which may be combined with the preceding embodiments, the methods further comprise de-crosslinking the tissue sample.

As described herein, it should be recognized that the order of contacting the biological or tissue sample with the quencher and the detectable probes may be adjusted to accommodate one or more additional sample processing steps as desired. Depending upon the class of analytes to be evaluated, certain sample processing steps may be included or omitted and the order of reagent application may change. For example, in analyses involving proteins as molecules of interest and protein-related sample processing steps, the quencher is preferably added after fixation, permeabilization/de-crosslinking, and staining to achieve better protein stability and signal downstream but prior to introduction of any detectable probes to the sample. In analyses involving only nucleic acids as molecules of interest and nucleic acid-related processing steps, such as in RNA workflows, the quencher is preferably added after application of primary probes to the sample, but may be added either before or after any amplification step, such as rolling circle amplification.

In some embodiments, the method for analyzing a biological sample comprises bleaching (e.g., chemical bleaching, photobleaching, photochemical bleaching, and/or exposure to heat) the sample prior to, simultaneously, or after being contacted with a quencher. In some embodiments, the combination of bleaching and quenching prior to signal detection increases signal-to-noise ratios and detectable object count density of the quenched biological sample as compared to an unbleached and/or unquenched biological sample.

(iii) Method for Analyzing a Tissue Sample

In one aspect, provided herein are methods for analyzing a tissue sample, comprising: contacting the tissue sample with a nucleic acid probe that directly or indirectly binds to a molecule of interest in the tissue sample; contacting the tissue sample with a quencher comprising a quencher dye and a targeting moiety, wherein the targeting moiety directly or indirectly binds and/or reacts with a biological moiety endogenous in the tissue sample, thereby targeting the quencher to the biological moiety; contacting the tissue sample with a fluorescently labeled detectable probe that directly or indirectly binds the nucleic acid probe or an amplification product of the nucleic acid probe; and detecting a signal associated with the fluorescently labeled detectable probe in the tissue sample, wherein the quencher dye reduces autofluorescence in the tissue sample, thereby detecting the molecule of interest in the tissue sample.

In another aspect, provided herein are methods for analyzing a tissue sample, comprising: contacting the tissue sample with a nucleic acid probe that directly or indirectly binds to a molecule of interest in the tissue sample; contacting the tissue sample with a quencher comprising a quencher dye and a targeting moiety, wherein the targeting moiety directly or indirectly binds and/or reacts with a biological moiety endogenous in the tissue sample, thereby targeting the quencher to the biological moiety, wherein the quencher is a compound of formula (I)

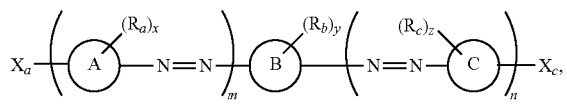

or a salt thereof, wherein,
each

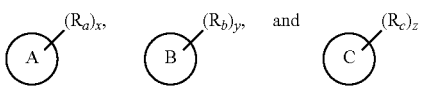

is independently selected from the group consisting of substituted or unsubstituted aryl, and substituted or unsubstituted heteroaryl;

$X_a$ is H, halo, —OH, $C_1$-$C_6$alkyl, $C_1$-$C_6$haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$alkyl, —$OSO_2$—$C_1$-$C_6$ haloalkyl, —CN, —SCN, —NCO, -cyano, or -L-($R_{target}$)$_w$, wherein w is any integer such as 1 or 2;

$X_c$ is H, halo, —OH, $C_1$-$C_6$ alkyl, $C_1$-$C_6$ haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, -cyano, or -L-($R_{target}$)$_w$, wherein w is any integer such as 1 or 2;

wherein $R^1$ and $R^2$ are independently H, $C_1$-$C_6$ alkyl or substituted $C_1$-$C_6$ alkyl; and each $R_a$ and $R_c$ is independently H, halo, —OH, $C_1$-$C_6$alkyl, $C_1$-$C_6$haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -cyano; each $R_b$ is H, halo, —OH, $C_1$-$C_6$alkyl, $C_1$-$C_6$haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, -cyano, $R_{b1}$, or -L-($R_{target}$)$_w$, wherein w is any integer such as 1 or 2;

$R_{b1}$ is a substituted or unsubstituted alkyl, a substituted or unsubstituted aryl, or a substituted or unsubstituted heteroaryl;

L is a bond or a linker moiety;

$R_{target}$ is a targeting moiety;

m is an integer from 0 to 6;

n is an integer from 0 to 6; and each of x, y and z is independently an integer from 0 to 5;

provided that at least one of m and n is nonzero; and
provided that at least one of
$X_a$, $X_c$, or $R_b$ is -L-$(R_{target})_w$, wherein w is any integer such as 1 or 2;
contacting the tissue sample with a fluorescently labeled detectable probe that directly or indirectly binds the nucleic acid probe or an amplification product of the nucleic acid probe; and detecting a signal associated with the fluorescently labeled detectable probe in the tissue sample, wherein the quencher dye reduces autofluorescence in the tissue sample, thereby detecting the molecule of interest in the tissue sample.

In another aspect, provided herein are methods for analyzing a tissue sample, comprising: contacting the tissue sample with a nucleic acid probe that directly or indirectly binds to a molecule of interest in the tissue sample; contacting the tissue sample with a quencher comprising a quencher dye and a targeting moiety, wherein the targeting moiety directly or indirectly binds and/or reacts with a biological moiety endogenous in the tissue sample, thereby targeting the quencher to the biological moiety, wherein the quencher is a compound of formula (II)

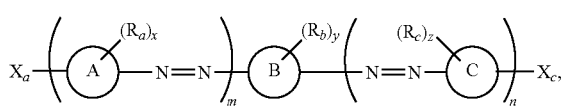

(II)

or a salt thereof, wherein,
each

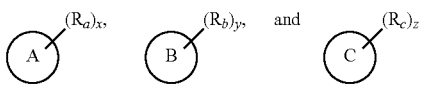

and is independently selected from the group consisting of substituted or unsubstituted aryl, and substituted or unsubstituted heteroaryl;
$X_a$ is H, halo, —OH, $C_1$-$C_6$ alkyl, $C_1$-$C_6$ haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, -cyano, or -L-$R_{target}$;
$X_c$ is H, halo, —OH, $C_1$-$C_6$ alkyl, $C_1$-$C_6$ haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, -cyano, or -L-$R_{target}$;
wherein $R^1$ and $R^2$ are independently H, $C_1$-$C_6$ alkyl or substituted $C_1$-$C_6$ alkyl; and
each $R_a$ and $R_c$ is independently H, halo, —OH, $C_1$-$C_6$ alkyl, $C_1$-$C_6$ haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -cyano; each $R_b$ is H, halo, —OH, $C_1$-$C_6$alkyl, $C_1$-$C_6$ haloalkyl, $C_1$-$C_6$ alkoxy, $C_1$-$C_6$ alkyl, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, -cyano, $R_{b1}$, or -L-$R_{target}$;
$R_{b1}$ is a substituted or unsubstituted alkyl, a substituted or unsubstituted aryl, or a substituted or unsubstituted heteroaryl;
L is a bond or a linker moiety;
$R_{target}$ is a targeting moiety;
m is an integer from 0 to 6;
n is an integer from 0 to 6; and
each of x, y and z is independently an integer from 0 to 5;
provided that at least one of m and n is nonzero; and
provided that at least one of $X_a$, $X_c$, or $R_b$ is -L-$R_{target}$;
contacting the tissue sample with a fluorescently labeled detectable probe that directly or indirectly binds the nucleic acid probe or an amplification product of the nucleic acid probe; and detecting a signal associated with the fluorescently labeled detectable probe in the tissue sample, wherein the quencher dye reduces autofluorescence in the tissue sample, thereby detecting the molecule of interest in the tissue sample.

In some embodiments, the tissue sample is contacted with the detectable probe prior to being contacted with the quencher. In other embodiments, the tissue sample is contacted with the detectable probe after being contacted with the quencher. In yet other embodiments, the tissue sample is contacted with the detectable probe and the quencher simultaneously.

In some embodiments, the step of contacting the tissue sample with the quencher may be carried out before or after one or more treatments for fixing, permeabilizing/de-crosslinking, and/or staining the biological sample. For example, in some embodiments, the methods of the present disclosure comprise staining the tissue sample. In some embodiments, which may be combined with the preceding embodiment, the methods further comprise fixing the tissue sample. In some embodiments, which may be combined with the preceding embodiments, the methods further comprise de-crosslinking the tissue sample.

It should be recognized that the order of contacting the tissue sample with the quencher and the detectable probes may be adjusted to accommodate one or more additional sample processing steps as desired. Depending upon the class of analytes to be evaluated, certain sample processing steps may be included or omitted and the order of reagent application may change. For example, in analyses involving proteins as molecules of interest and protein-related sample processing steps, the quencher is preferably added after fixation, permeabilization/de-crosslinking, and staining to achieve better protein stability and signal downstream but prior to introduction of any detectable probes to the sample. In analyses involving only nucleic acids as molecules of interest and nucleic acid-related processing steps, such as in RNA workflows, the quencher is preferably added after application of primary probes to the sample, but may be added either before or after any amplification step, such as rolling circle amplification.

In some embodiments, the method for analyzing a tissue sample comprises bleaching (e.g., chemical bleaching, photobleaching, photochemical bleaching, exposure to heat) the sample prior to, simultaneously, or after being contacted with a quencher. In some embodiments, the combination of bleaching and quenching prior to signal detection increases signal-to-noise ratios and detectable object count density in the quenched tissue sample as compared to an unbleached and/or unquenched tissue sample.

(iv) Additional Detectable Probes and Multiple Imaging Cycles

The methods of any of the preceding aspects may also encompass multiple cycles of imaging and the accompanying treatments for addition and/or removal of detectable probes. As detailed herein, the quenchers of the present disclosure combine broadband absorption with durable targeting chemistries such that the quenchers persist in the biological sample or tissue samples being evaluated of the course of multiple rounds of washing and stripping to exchange detectable probes.

In some embodiments of any of the preceding aspects, the methods further comprise removing the detectable probe or a portion thereof from the biological sample, wherein the quencher remains in the biological sample, optionally wherein the removing step comprises treating the biological sample with a denaturing agent and/or heating. In some embodiments of any of the preceding aspects, the methods further comprise removing the detectable probe or a portion thereof from the tissue sample, wherein the quencher remains in the tissue sample, optionally wherein the removing step comprises treating the tissue sample with a denaturing agent and/or heating. In certain embodiments, the denaturing agent comprises dimethyl sulfoxide (DMSO), formamide, and/or an alkaline solution. In some embodiments, the method comprises a signal removal step. For example, the methods provided herein may comprise photobleaching, chemical deactivation, chemical cleavage of the fluorophores (e.g., disulfide cleavage), enzymatic cleavage (using, for example, an exonuclease, endonuclease, protease, or USER™ (Uracil-Specific Excision Reagent) cleavage system), DNA/RNA strand displacement, chemical or heat denaturing of an intermediate fluorescent oligonucleotide, and/or any suitable signal removal step. In some embodiments, the removal step comprises performing a stringent wash. Exemplary detectable methods are described in U.S. Pat. No. 6,828,109, US 2019/0376956, US 2019/0376956, US 2022/0026433, US 2022/0128565, and US 2021/0222234, all of which are incorporated herein by reference in their entireties. The signal removing step can be performed prior to, after, and/or simultaneously with the quencher quenching autofluorescence in the biological sample, and can be repeated one or more times while the quencher remains in the biological sample and at least partially quenches the autofluorescence in the biological sample.

In some embodiments of any of the preceding aspects, the methods further comprise contacting the biological sample with one or more additional detectable probes, wherein each additional detectable probe directly or indirectly binds to an additional molecule of interest in the biological sample, and the additional molecule of interest is the same or different from the molecule of interest in the detecting step (b). In certain embodiments of any of the preceding aspects, the methods further comprise contacting the tissue sample with one or more additional detectable probes, wherein each additional detectable probe directly or indirectly binds to an additional molecule of interest in the tissue sample, and the additional molecule of interest is the same or different from the molecule of interest in the detecting step (b).

In some embodiments, the method further comprises detecting a signal or signals associated with the one or more additional detectable probes in the biological sample, wherein the autofluorescence of the biological sample remains reduced as compared to an unquenched biological sample. In certain embodiments, the method further comprises detecting a signal or signals associated with the one or more additional detectable probes in the tissue sample, wherein the autofluorescence of the tissue sample remains reduced as compared to an unquenched tissue sample.

In other embodiments, the one or more additional detectable probes are contacted with the biological sample and the signal or signals associated with the one or more additional detectable probes are detected in one or more cycles, optionally wherein each cycle comprises removing the additional detectable probe(s) for the cycle from the biological sample prior to contacting the biological sample with the additional detectable probe(s) for a subsequent cycle. In still other embodiments, the one or more additional detectable probes are contacted with the tissue sample and the signal or signals associated with the one or more additional detectable probes are detected in one or more cycles, optionally wherein each cycle comprises removing the additional detectable probe(s) for the cycle from the tissue sample prior to contacting the tissue sample with the additional detectable probe(s) for a subsequent cycle.

In some embodiments of any of the foregoing aspects wherein one or more additional detectable probes are contacted with the biological sample and the signal or signals associated with the one or more additional detectable probes are detected in one or more cycles the methods comprise at least two, three, four, five, six, or more cycles of contacting the biological sample with the one or more additional detectable probes. In some embodiments of any of the foregoing aspects wherein one or more additional detectable probes are contacted with the tissue sample and the signal or signals associated with the one or more additional detectable probes are detected in one or more cycles the methods comprise at least two, three, four, five, six, or more cycles of contacting the tissue sample with the one or more additional detectable probes.

B. Quencher

As provided herein, the methods for reducing autofluorescence and analyzing biological samples, optionally wherein the biological samples are tissue samples, employ quencher compounds comprising quencher dye moieties having a broad absorption spectrum of visible light and targeting moieties that react or bind with endogenous biological moieties present in the biological samples over multiple cycles of imaging. The quenchers provided herein may be described in terms of their constitutive chemical moieties, their chemical structures as a whole, or even their optical properties.

A quencher dye can absorb energy from a fluorophore (such as a fluorescent dye) and re-emit energy as either heat (in the case of dark quenchers) or visible light (in the case of fluorescent quenchers). In some embodiments, a quencher dye disclosed herein is a dark quencher such as one comprising a dabcyl moiety. In some embodiments, a quencher dye disclosed herein is not a fluorescent quencher. In some embodiments, a quencher dye disclosed herein is targeted to the proximity of an autofluorescent source in a sample, and the quencher dye absorbs the energy emitted from the autofluorescent source, thereby suppressing autofluorescence emission. In some embodiments, a quencher dye is a masking moiety, wherein the quencher dye masks the energy emitted from the autofluorescent source. In some embodiments, a quencher disclosed herein comprises a quencher dye coupled to a targeting moiety, and the quencher is dimensioned such that upon binding and/or reaction of the targeting moiety with an autofluorescent source in a sample, the quencher dye is sufficiently close to the autofluorescent source to quench the autofluorescent source. In some embodiments, the quencher dye is less than 15 nm away from the autofluorescent source. In some embodiments, the quencher dye is less than 10 nm away from the autofluorescent source. In some embodiments, the quencher dye is less than 5 nm away from the autofluorescent source. In some embodiments, the quencher dye is targeted by the targeting moiety preferentially to autofluorescent sources in the sample than to detectable probes (e.g., fluorescently labeled probes) directly or indirectly bound to molecules of interest in the sample.

(i) Quencher Dye

The quencher dye as described herein encompasses the chemical moiety of the quencher that reduces the autofluorescence emitted by endogenous biological moieties by absorbing the emitted light. The quencher dyes, and thus also the quenchers containing the quencher dye moieties, have broadband absorption in the visible region of the electromagnetic spectrum. The quencher dyes are typified by several mono-, bi-, or polycyclic aromatic or heteroaromatic rings. The absorption spectrum of the quencher may be shifted or tuned via adjustments to the substitution patterns of the various (hetero)aromatic residues or rings.

In some embodiments, the quencher dye comprises (a) at least three aromatic residues, wherein each aromatic residue is independently unsubstituted aryl, substituted aryl, unsubstituted heteroaryl, or substituted heteroaryl, wherein at least one aromatic residue is covalently linked to two other aromatic residues via two exocyclic azo bonds; or (b) at least two aromatic residues, wherein each aromatic residue is independently unsubstituted aryl, substituted aryl, unsubstituted heteroaryl, or substituted heteroaryl, wherein at least two of said aromatic residues are covalently linked via an exocyclic azo bond, wherein at least one said aromatic residue is an unsubstituted polycyclic aryl, a substituted polycyclic aryl, an unsubstituted polycyclic heteroaryl group, or a substituted polycyclic heteroaryl group. In any of the embodiments herein, "polycyclic" comprises an aromatic ring system or heteroaromatic ring system having multiple rings (e.g., more than one ring). In any of the embodiments herein, "azo" comprises a diazenyl functional group having the structure —N═N—.

In some embodiments, the quencher dye comprises an optionally substituted 1,4-bis((E)-phenyldiazenyl)benzene moiety

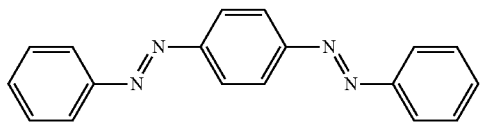 [SMILES: c1ccc(/N=N/c2ccc(/N=N/c3ccccc3)cc2)cc1]

or an optionally substituted (E)-5-phenyl-3-(phenyldiazenyl)phenazin-5-ium moiety

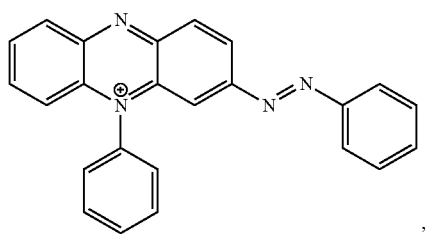 [SMILES: c1ccc(/N=N/c2ccc3nc4ccccc4[n+](-c4ccccc4)c3c2)cc1]

or a salt thereof.

In some embodiments, the quencher dye comprises at least three aromatic moieties or residues, wherein each aromatic moiety or residue is independently unsubstituted aryl, substituted aryl, unsubstituted heteroaryl, or substituted heteroaryl, wherein at least one aromatic moiety or residue is covalently linked to two other aromatic moieties or residues via two exocyclic azo bonds. In certain embodiments, the quencher dye comprises an optionally substituted 1,4-bis((E)-phenyldiazenyl)benzene moiety

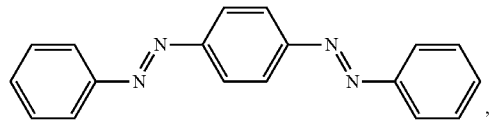

or a salt thereof. In other embodiments, the quencher dye comprises at least two aromatic moieties or residues, wherein each aromatic moiety or residue is independently unsubstituted aryl, substituted aryl, unsubstituted heteroaryl, or substituted heteroaryl, wherein at least two of said aromatic moieties or residues are covalently linked via an exocyclic azo bond, wherein at least one said aromatic moiety or residue is an unsubstituted polycyclic aryl, a substituted polycyclic aryl, an unsubstituted polycyclic heteroaryl group, or a substituted polycyclic heteroaryl group. In certain other embodiments, the quencher dye comprises an optionally substituted (E)-5-phenyl-3-(phenyldiazenyl)phenazin-5-ium moiety

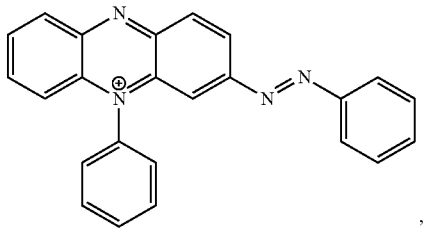 [SMILES: c1ccc(/N=N/c2ccc3nc4ccccc4[n+](-c4ccccc4)c3c2)cc1]

or a salt thereof.

It should be recognized by those skilled in the art that the effective quenching of any fluorescent entity is highly dependent upon the distance between the quenching dye and the fluorescent or autofluorescent source. Despite the broadband absorption of the quencher dyes as provided herein, the quenchers of the present disclosure achieve high quenching efficiency of background autofluorescence without also substantially reducing the desired fluorescence signals emitted by or associated with detectable probes. The quenchers of the present disclosure achieve the specific quenching of background autofluorescence by employing targeting moieties to react the quencher dyes to or near the sources of autofluorescence in biological samples or tissue samples.

(ii) Targeting Moiety

In some embodiments, a quencher dye can be modified with functional groups that target the endogenous biological moiety, such as lipofuscin, collagen, elastin, etc. For instance, lipofuscin is a brown-yellow, electron-dense, autofluorescent material that accumulates progressively over time in lysosomes of postmitotic cells, such as neurons and cardiac myocytes. In some embodiments, a quencher dye can be a dark quencher such as a dark dye that absorbs energy from a fluorophore and re-emits most of the energy as heat. In some embodiments, the quencher dye is chemically modified with one, two, or more functional groups for targeting the quencher dye to one or more autofluorescence sources in a sample. In some embodiments, two or more quencher dye molecules can be modified with the same one or more functional groups. In some embodiments, two or more quencher dye molecules can be modified with one or more different functional groups. In some embodiments, two or more functional groups on the same modified quencher dye molecule can be the same or different. In some embodiments, one or more hydrophobic tails can be attached (directly or indirectly and/or covalently or non-covalently) to a quencher dye to bind lipofuscin or other molecules or complexes comprising lipid. For instance, a hydrophobic tail can be inserted into a lipid layer, thereby targeting a quencher dye to the complex comprising the lipid layer. In some embodiments, an NHS moiety can bind to a polypeptide such as a protein, thereby targeting a quencher dye to the polypeptide.

In some embodiments, a quencher comprising a targeting moiety disclosed herein can provide selectivity and durability for targeting and masking autofluorescence in a sample, for example, via lipophilic and/or covalent anchoring of the quencher dye in the sample. In some embodiments, a quencher comprising a targeting moiety disclosed herein can be used for targeted quenching, e.g., the quencher dye is targeted to one or more autofluorescence sources in a sample and does not substantially interfere with detectable signals associated with detectable probes directly or indirectly bound to molecules of interest in the tissue sample. In some embodiments, the quencher dye targeted to one or more autofluorescence sources in a sample does not substantially interfere with detectable signals associated with rolling circle amplification products in the sample. In some embodiments, the quencher dye targeted to one or more autofluorescence sources in a sample remains in the sample, e.g., through covalent bonds and/or non-covalent interactions such as lipophilic insertion. In some embodiments, a quencher dye coupled to a targeting moiety disclosed herein remains in the sample (e.g., a tissue sample) longer than a quencher dye not coupled to a targeting moiety. In some embodiments, a quencher dye coupled to a targeting moiety disclosed herein requires less frequent quenching than a quencher dye not coupled to a targeting moiety. In some embodiments, the quencher dye coupled to the targeting moiety can be contacted with the sample once. In some embodiments, the quencher dye coupled to the targeting moiety allows detection of signals associated with molecules of interest in the sample with high signal-to-noise ratios and/or high detectable object count densities through sequential probe hybridization, stripping, and re-hybridization cycles.

The targeting moiety as provided herein encompasses the portion of the quencher which reacts or binds to the endogenous biological moieties in the biological samples. In some embodiments, the targeting moiety binds directly or indirectly to the endogenous biological moiety present in the biological or tissue sample.

In some embodiments, the interaction between the targeting moiety and the endogenous biological moiety may take the form of covalent chemical bonds such that the quencher remains intact in the biological or tissue sample. In some embodiments, the targeting moiety comprises a first functional group, and the endogenous biological moiety comprises a second functional group capable of reacting with the first functional group to form a covalent bond.

Suitable first functional groups of the targeting moiety may include but are not limited to: carboxylic acids or derivatives thereof, such as various acid halides or esters, hydroxyl groups, thiol groups, amino groups, alkenyl or dienyl groups, epoxide groups, haloalkyl groups, or phosphoramidite groups. In certain embodiments, the first functional group is a carboxylic acid moiety or derivative thereof, aldehyde or ketone moiety, sulfonyl halide moiety, hydroxyl moiety, thiol moiety, amino moiety, alkenyl or dienyl moiety, epoxide moiety, or a haloalkyl moiety.

In certain embodiments, the first functional group is a maleimido moiety, an azido moiety, an alkynyl moiety, an N-hydroxysuccinimidyl ester moiety, or a carbonylimidazolyl moiety. In still certain other embodiments, the first functional group is a maleimido moiety.

It should be recognized that the first functional groups of the targeting moiety may react with the second functional group of the endogenous biological moiety in a number of different chemical reaction mechanisms, depending on the first functional group selected. For example, certain first functional groups may contain chemical moieties suitable as leaving groups or nucleophiles for nucleophilic or electrophilic substitution, or others may contain chemical moieties capable of undergoing cycloaddition. In still other embodiments, certain first functional groups may be converted to other functional groups capable of forming a covalent bond to the endogenous biological moiety.

Alternatively, in other embodiments, the endogenous biological moiety may not possess any functional groups with which another functional group could easily form a covalent bond. In such instances, the interaction between the targeting moiety and endogenous biological moiety may take the form of intermolecular attraction between similarly polar or similarly non-polar moieties. For example, lipofuscin, an endogenous biological moiety, encompasses autofluorescent granules composed of lipid-containing residues resulting from lysosomal digestion. The hydrocarbon, lipid-containing residues of lipofuscin are not readily reacted with other functional groups to form covalent bonds. The targeting moiety for lipofuscin instead can include a hydrophobic, lipophilic moiety that forms favorable intermolecular interactions with the lipid residues, by insertion between adjacent lipid-containing residues such that the targeting moiety becomes effectively wedged in the lipofuscin. In some instances, a targeting moiety for lipofuscin may comprise a protein targeting moiety (e.g., thiol or amine targeting chemistry).

In some embodiments, the targeting moiety comprises a hydrophobic portion for lipophilic insertion into the endogenous biological moiety, optionally wherein the autofluorescent moiety comprises lipofuscin. In some embodiments, the hydrophobic portion for lipophilic insertion into the endogenous biological moiety is a $C_6$-$C_{14}$ alkyl moiety, $C_6$-$C_{14}$ alkenyl moiety, terpenoid moiety, sterol moiety, or wax moiety.

The targeting moieties, which react or bind the quencher dye to the endogenous biological moieties of the biological sample, constrain the distance of the quencher dyes to fall within a certain range of autofluorescence source(s), such as the endogenous biological moieties detailed herein. The targeting of the quencher dyes to the endogenous biological moieties contrasts existing uses of commercially available quenchers. For example, commercially available quenchers used in fluorescence in situ hybridization measurements are randomly physi-sorbed onto biological samples, without targeting autofluorescent background sources. As a result, these commercially available quenchers may also quench the fluorescence signal associated with the analytes of interest. Furthermore, the use of the quenchers provided herein is distinguished from other techniques, such as Forster Resonance Energy Transfer, wherein the quencher is targeted to an analyte of interest and actively employed to quench a fluorescence signal associated with the analyte of interest.

(iii) Linker Moiety

In some embodiments, the quencher further comprises a linker moiety, which is not a bond, linking the quencher dye and the targeting moiety. In other embodiments, the linker moiety is an alkylene moiety, an aminoalkylene moiety, an amino(alkyl)alkylene moiety, a polyethylene glycol moiety, a disulfide moiety, or a carbamate moiety.

The linker moiety of the quencher may be selected as required for synthesis of the complete quencher compound in view of availability of starting reagents, but also provides additional levers to tune the chemical properties of the quencher as a whole and to control the distance between the quencher dye and the endogenous biological activity. For example, in some embodiments, certain linkers may be selected, such as polyethylene glycol moieties or alkylene moieties, to modify the solubility of the quencher in polar or non-polar solvents. Other linkers may be selected for facile enzymatic cleavage such as carbamate linkers, or chemical removal, such as disulfide bridges, as required for analysis by other techniques.

In some embodiments, the linker is cleavable or comprises hydrophilic groups or stimuli-driven cleavable functional groups (such as smart autofluorescence masking) to facilitate higher solubility. In certain embodiments, the linker comprises a stimuli-driven cleavable functional group that releases the entire quencher or at least a portion of the quencher, such as the quenching dye, when exposed to the stimulus. The removal of the quencher from the quenched biological sample may be useful for downstream processing, such as Hematoxylin and Eosin (H&E) staining after fluorescence imaging. For example, in some embodiments wherein the linker is cleavable, the methods provided herein may comprise contacting a quenched biological sample or quenched tissue sample with a reducing agent, thereby cleaving the quencher dye. In certain embodiments, the reducing agent is sodium dithionate ($Na_2S_2O_4$). In some embodiments, the method comprises contacting the quenched biological sample or quenched tissue sample with sodium dithionate, optionally wherein the sample is contacted with a 10 mM aqueous solution of sodium dithionate at room temperature.

(iv) UV-Visible Absorption

The visible light region of the electromagnetic spectrum is the primary region evaluated in fluorescence measurements for in situ analysis. However, many endogenous biological moieties that are autofluorescent also fluoresce in this range of wavelengths. As detailed above, the quenchers of the present disclosure combine broadband visible light absorption with targeted chemistry to remain intact in biological samples and maintain high levels of autofluorescence quenching over multiple cycles of imaging.

In some embodiments, the quencher has a UV-visible absorption profile with at least one absorption peak with an absorption maximum between about 400 nm and 700 nm, between about 400 nm and 600 nm, between about 400 nm and 500 nm, between about 500 nm and 700 nm, between about 500 nm and 600 nm, or between about 600 nm and 700 nm, and full-width half-maximum of at least about 50 nm, at least about 75 nm or at least about 100 nm. In certain embodiments, the quencher has a UV-visible absorption profile with at least one absorption peak with an absorption maximum between about 400 nm and 700 nm and full-width half-maximum of at least about 100 nm. In some embodiments, the quencher has a UV-visible absorption profile with at least one absorption peak with an absorption maximum between about 500 and about 600 nm and full-width half-maximum of at least about 100 nm.

In some embodiments, the quencher has a UV-visible absorption spectrum as shown in FIG. 1.

(v) Compounds of Formula (I) and Formula (II)

In some embodiments of the foregoing methods, the quencher is a compound of formula (I),

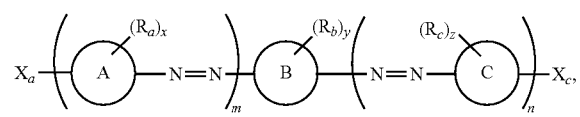

or a salt thereof, wherein
each

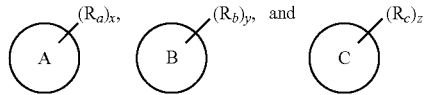

and is independently selected from the group consisting of substituted or unsubstituted aryl, and substituted or unsubstituted heteroaryl;

$X_a$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-($R_{target}$)$_w$, wherein w is any integer such as 1 or 2;

$X_c$ is H, halo, —OH, $C_1$-$C_6$alkyl, $C_1$-$C_6$haloalkyl, $C_1$-$C_6$alkoxy, $C_1$-$C_6$ haloalkoxy, hydroxyl-$C_1$-$C_6$alkylene, —$NR^1R^2$, —$NO_2$, —$SO_3H$, —$SO_3^-$, —$OSO_2$—$C_1$-$C_6$alkyl, —$OSO_2$—$C_1$-$C_6$haloalkyl, —CN, —SCN, —NCO, or -L-($R_{target}$)$_w$, wherein w is any integer such as 1 or 2;

wherein $R^1$ and $R^2$ are independently H, unsubstituted $C_1$-$C_6$ alkyl or substituted $C_1$-$C_6$ alkyl; and each $R_a$ and $R_c$ is independently H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, or —NCO;

each $R_b$ is independently H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, $R_{b1}$, or -L-($R_{target}$), wherein w is any integer such as 1 or 2, $R_{b1}$ is a substituted or unsubstituted alkyl, a substituted or unsubstituted aryl, or a substituted or unsubstituted heteroaryl;

L is a bond or a linker moiety;

$R_{target}$ is a targeting moiety;

n is an integer from 0 to 6;

n is an integer from 0 to 6; and each of x, y and z is independently an integer from 0 to 5;

provided that at least one of m and n is nonzero; and provided that at least one of $X_a$, $X_c$, or $R_b$ is -L-($R_{target}$), wherein w is any integer such as 1 or 2.

In some embodiments of the foregoing methods, the quencher is a compound of formula (II),

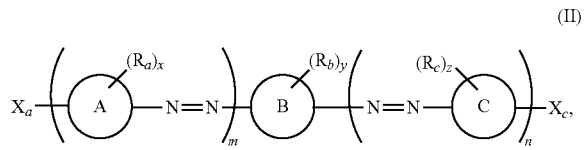

or a salt thereof, wherein
each

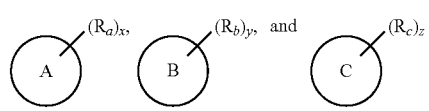

is independently selected from the group consisting of substituted or unsubstituted aryl, and substituted or unsubstituted heteroaryl $X_a$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-$R_{target}$, $X_c$ is 1, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-$R_{target}$, wherein $R^1$ and $R^2$ are independently 1, unsubstituted $C_1$-$C_6$ alkyl or substituted $C_1$-$C_6$ alkyl, and each $R^a$ and $R^c$ is independently H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, or —NCO;

each $R_b$ is independently H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, $R_{b1}$, or -L-$R_{target}$;

$R_{b1}$ is a substituted or unsubstituted alkyl, a substituted or unsubstituted aryl, or a substituted or unsubstituted heteroaryl;

L is a bond or a linker moiety,
$R_{target}$ is a targeting moiety;
m is an integer from 0 to 6;
n is an integer from 0 to 6; and
each of x, y and z is independently an integer from 0 to 5;

provided that at least one of m and n is nonzero, and provided that at least one of $X_a$, $X_c$, or $R_b$ is -L-$R_{target}$.

In some embodiments, m is an integer from 0 to 6, provided that at least one of m and n is nonzero. In certain embodiments, m is an integer 0, 1, 2, 3, 4, 5 or 6, provided that at least one of m and n is nonzero. In other embodiments, m is an integer from 1 to 6, from 2 to 6, from 3 to 6, from 4 to 6, or from 5 to 6. In some embodiments, n is an integer from 0 to 6, provided that at least one of m and n is nonzero. In certain embodiments, n is an integer 0, 1, 2, 3, 4, 5 or 6, provided that at least one of m and n is nonzero. In other embodiments, n is an integer from 1 to 6, from 2 to 6, from 3 to 6, from 4 to 6, or from 5 to 6.

In some embodiments, m is an integer from 1 to 6 and n is an integer from 0 to 6. In other embodiments, m is an integer from 0 to 6 and n is an integer from 1 to 6. In certain embodiments, m is an integer from 1 to 6 and n is an integer from 1 to 6. In some embodiments, m is 0 and n is 1. In other embodiments, m is 1 and n is 0. In yet other embodiments, in is 1 and n is 1.

In some embodiments, each

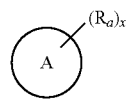

is independently selected from the group consisting of substituted or unsubstituted aryl, and substituted or unsubstituted heteroaryl. In some embodiments, each

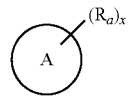

is independently a substituted or unsubstituted aryl. In certain embodiments, each

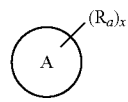

is independently a substituted or unsubstituted phenyl. In other embodiments, each

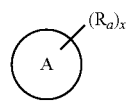

is independently a substituted or unsubstituted heteroaryl. In certain other embodiments, each

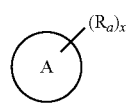

is independently a substituted or unsubstituted pyridinyl.

In some embodiments,

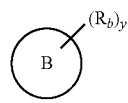

is selected from the group consisting of substituted or unsubstituted aryl, and substituted or unsubstituted heteroaryl. In some embodiments,

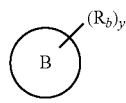

is a substituted or unsubstituted aryl. In certain embodiments,

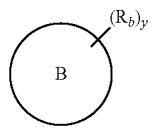

is a substituted or unsubstituted phenyl. In other embodiments,

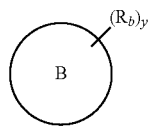

is a substituted or unsubstituted heteroaryl. In certain other embodiments,

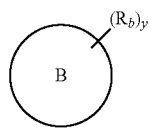

is a substituted or unsubstituted pyridinyl or a substituted or unsubstituted phenazinyl.

In some embodiments, each

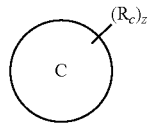

is independently selected from the group consisting of substituted or unsubstituted aryl, and substituted or unsubstituted heteroaryl. In some embodiments, each

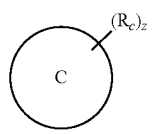

is independently a substituted or unsubstituted aryl. In certain embodiments, each

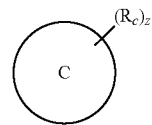

is independently a substituted or unsubstituted phenyl. In other embodiments, each

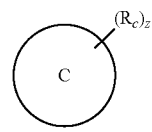

is independently a substituted or unsubstituted heteroaryl. In certain other embodiments,

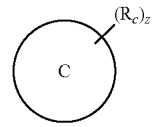

is a substituted or unsubstituted pyridinyl.

In some embodiments of the compound of Formula (I) or Formula (II), at least one, at least two or at least three instances of or

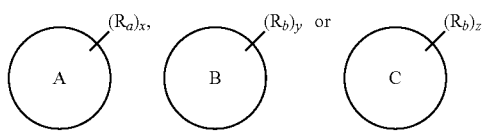

is substituted phenyl or unsubstituted phenyl. In some embodiments of the compound of Formula (I), the quencher has the following structure:

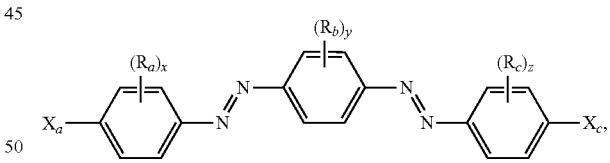

or a salt thereof, provided that at least one of $X_a$ and $X_c$ is -L-$(R_{target})_w$, wherein w is any integer such as 1 or 2, and wherein L is a bond or a linker moiety; and $R_{target}$ is a targeting moiety.

In some embodiments of the compound of formula (II), the quencher has the following structure:

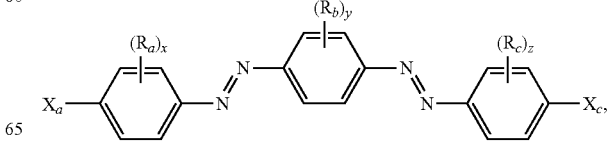

or a salt thereof, provided that at least one of $X_a$ and $X_c$ is -L-$R_{target}$, wherein L is a bond or a linker moiety; and $R_{target}$ is a targeting moiety.

In other embodiments,

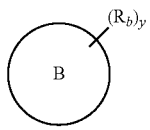

is

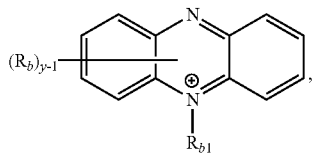

wherein $R_{b1}$ is a substituted or unsubstituted alkyl, a substituted or unsubstituted aryl, or a substituted or unsubstituted heteroaryl. In certain embodiments,

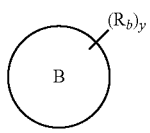

is

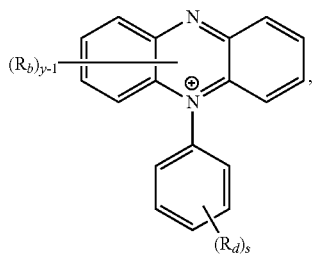

wherein $R_d$ is H, $C_1$-$C_6$ alkyl, or halo; and s is an integer from 0 to 5. In some embodiments, the quencher has the following structure.

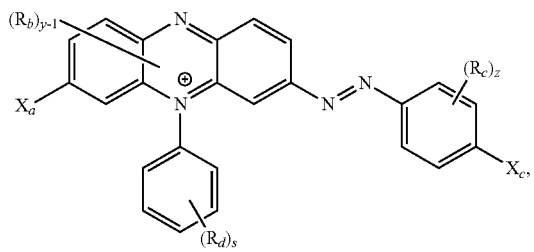

or a salt thereof.

In some embodiments, $X_a$ is H, halo, —OH—, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-$(R_{target})_w$, wherein w is any integer such as 1 or 2. In some embodiments, $X_a$ is H, halo, —OH, $C_1$-$C_6$-alkyl, —$NR^1R^2$, —$NO_2$, —$SO_3H$, —$SO_3^-$, —CN, or -L-$(R_{target})_w$, wherein w is any integer such as 1 or 2.

In some embodiments, $X_a$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-$R_{target}$. In some embodiments, $X_a$ is H, halo, —OH, $C_1$-$C_6$ alkyl, —$NR^1R^2$, —$NO_2$, —$SO_3H$, —$SO_3^-$, —CN, or -L-$R_{target}$.

In some embodiments, $X_c$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-$(R_{target})_w$, wherein w is any integer such as 1 or 2. In some embodiments, $X_c$ is H, halo, —OH, $C_1$-$C_6$ alkyl, —$NR^1R^2$, —$NO_2$, —$SO_1H$, —$SO_3^-$, —CN, or -L-$(R_{target})_w$, wherein w is any integer such as 1 or 2.

In some embodiments, $X_c$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, or -L-$R_{target}$. In some embodiments, $X_c$ is H, halo, —OH, $C_1$-$C_6$ alkyl, —$NR^1R^2$, —$NO_2$, —$SO_3H$, —$SO_3^-$, —CN, or -L-$R_{target}$.

In some embodiments, $R^1$ and $R^2$ are independently H, unsubstituted $C_1$-$C_6$ alkyl or substituted $C_1$-$C_6$ alkyl. In some embodiments $R^1$ is H and $R^2$ is H. In other embodiments, $R^1$ is H and $R^2$ is unsubstituted $C_1$-$C_6$ alkyl or substituted $C_1$-$C_6$ alkyl. In other embodiments, $R^1$ is unsubstituted $C_1$-$C_6$ alkyl or substituted $C_1$-$C_6$ alkyl and $R^2$ is H. In yet other embodiments, $R^1$ is unsubstituted $C_1$-$C_6$ alkyl or substituted $C_1$-$C_6$ alkyl and $R^2$ is unsubstituted $C_1$-$C_6$ alkyl or substituted $C_1$-$C_6$ alkyl.

In some embodiments, each $R_a$ and $R_c$ is independently H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, or —NCO. In some embodiments, $R_a$ is H, halo, —OH, $C_1$-$C_6$ alkyl, —$NR^1R^2$, —$NO_2$, —$SO_3H$, —$SO_3^-$, or —CN. In other embodiments $R_c$ is H, halo, —OH, $C_1$-$C_6$ alkyl, —$NR^1R^2$, —$NO_2$, —$SO_3H$, —$SO_3^-$, —CN, In some embodiments, each $R_b$ independently is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_2$, —$SO_3H$, —$SO_3^-$, —$OSO_2$—$C_1$-$C_6$ alkyl, —$OSO_2$—$C_1$-$C_6$ haloalkyl, —CN, —SCN, —NCO, $R_{b1}$, or -L-$(R_{target})_w$, wherein w is any integer such as 1 or 2. In some embodiments, each $R_b$ is independently —$NR^1R^2$, $R_{b1}$, or -L-$(R_{target})_w$, wherein w is any integer such as 1 or 2.

In some embodiments, each $R_b$ independently is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —$NR^1R^2$, —$NO_3$, —$SO_3H$, —$SO_3^-$, —$OSO_2$—$C_1$-$C_6$ alkyl, —$OSO_2$—$C_1$-$C_6$ haloalkyl, —CN, —SCN, —NCO, $R_{b1}$, or -L-$R_{target}$. In some embodiments, each $R_b$ is independently —$NR^1R^2$, $R_{b1}$, or -L-$R_{target}$.

In some embodiments, $R^1$ and $R^2$ are independently H, unsubstituted $C_1$-$C_6$ alkyl or substituted $C_1$-$C_6$ alkyl. In some embodiments $R^1$ is H and $R^2$ is H. In other embodiments, $R^1$ is H and $R^2$ is unsubstituted $C_1$-$C_6$ alkyl or substituted $C_1$-$C_6$ alkyl. In other embodiments, $R^1$ is unsubstituted $C_1$-$C_6$ alkyl or substituted $C_1$-$C_6$ alkyl and $R^2$ is H.

In yet other embodiments, $R^1$ is unsubstituted $C_1$-$C_6$alkyl or substituted $C_1$-$C_6$ alkyl and $R^2$ is unsubstituted $C_1$-$C_6$ alkyl or substituted $C_1$-$C_6$ alkyl.

In some embodiments, $R_{b1}$ is a substituted or unsubstituted alkyl, a substituted or unsubstituted aryl, or a substituted or unsubstituted heteroaryl. In some embodiments, $R_{b1}$ is a substituted or unsubstituted alkyl. In other embodiments, $R_{b1}$ is a substituted or unsubstituted aryl. In certain embodiments, $R_{b1}$ is a substituted or unsubstituted phenyl. In yet other embodiments, $R_{b1}$ is a substituted or unsubstituted heteroaryl. In certain other embodiments, $R_{b1}$ is a substituted or unsubstituted pyridinyl.

In some embodiments, L is a bond or a linker moiety. In certain embodiments L is a linker moiety. In certain other embodiments, L is an alkylene moiety, an aminoalkylene moiety, an amino(alkyl)alkylene moiety, a polyethylene glycol moiety, a disulfide moiety, or a carbamate moiety. In some embodiments, L is a linker moiety comprising one or more of an alkylene moiety, an aminoalkylene moiety, an amino(alkyl)alkylene moiety, an oligoethylene glycol moiety, a polyethylene glycol moiety, a disulfide moiety, or a carbamate moiety. In some embodiments, L is a linker moiety comprising a carbamate and a polyethylene glycol moiety.

In some embodiments, $R_{target}$ is a targeting moiety. In some embodiments, $R_{target}$ is a $C_6$-$C_{14}$ alkyl moiety, $C_6$-$C_{14}$ alkenyl moiety, terpenoid moiety, sterol moiety, or wax moiety. In other embodiments, $R_{target}$ is a carboxylic acid moiety or derivative thereof, aldehyde or ketone moiety, sulfonyl halide moiety, hydroxyl moiety, thiol moiety, amino moiety, alkenyl or dienyl moiety, epoxide moiety, or haloalkyl moiety. In certain embodiments, $R_{target}$ is a maleimido moiety, an azido moiety, an alkynyl moiety, an N-hydroxysuccinimidyl ester moiety, or a carbonylimidazolyl moiety. In still certain other embodiments, $R_{target}$ is a maleimido moiety.

In some embodiments, the quencher is selected from the group consisting of:

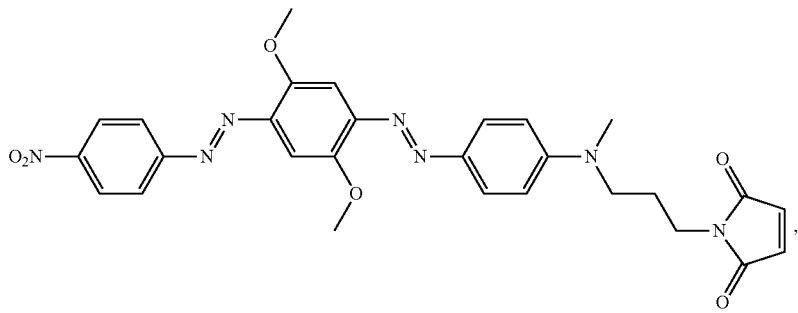

,

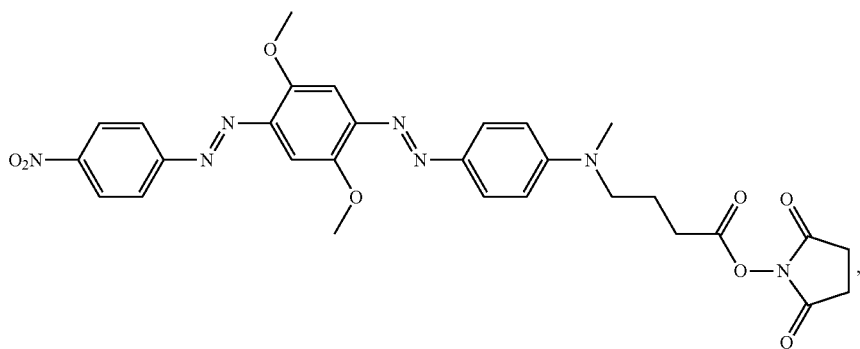

,

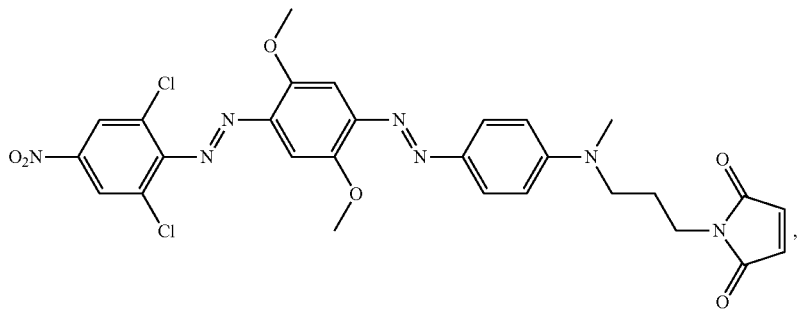

,

-continued
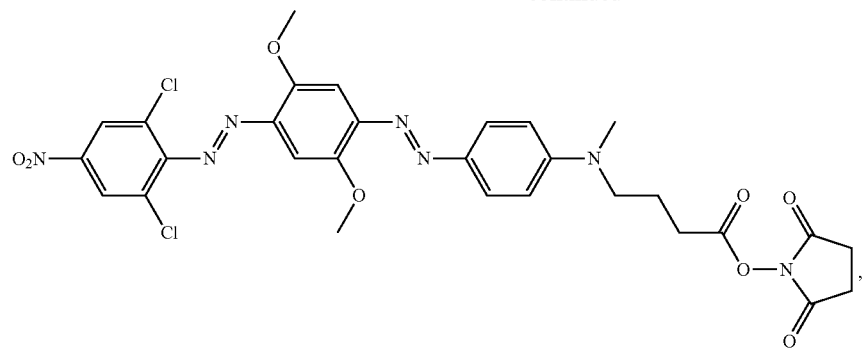
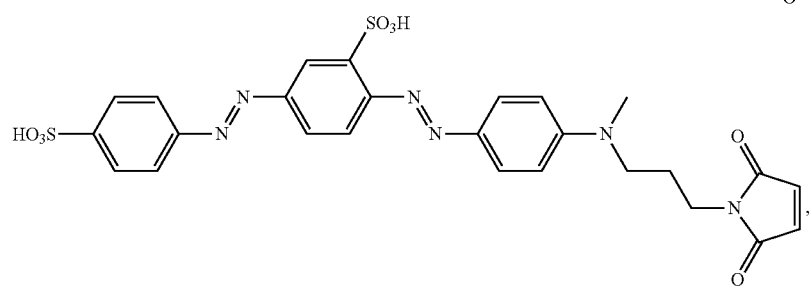
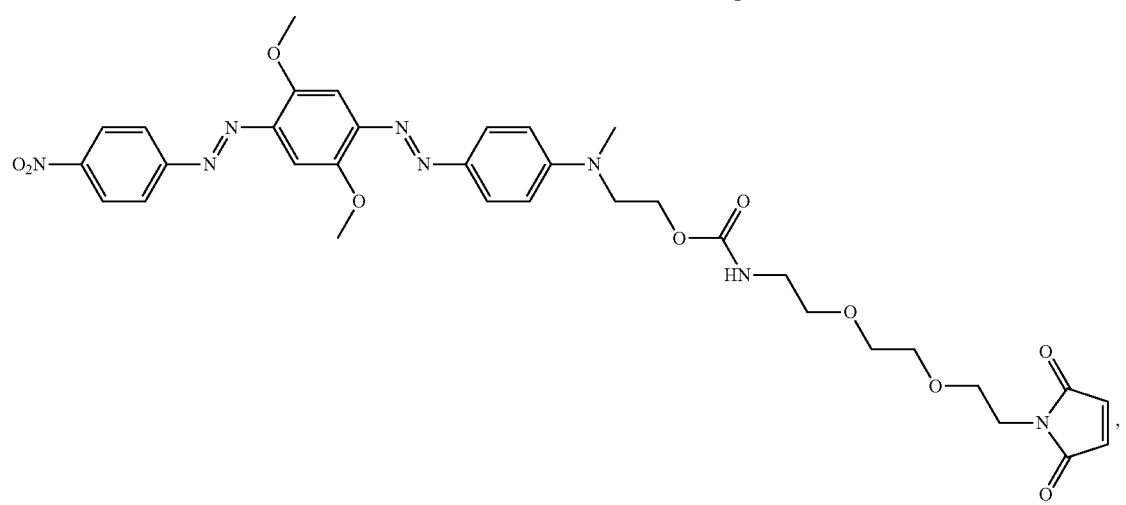
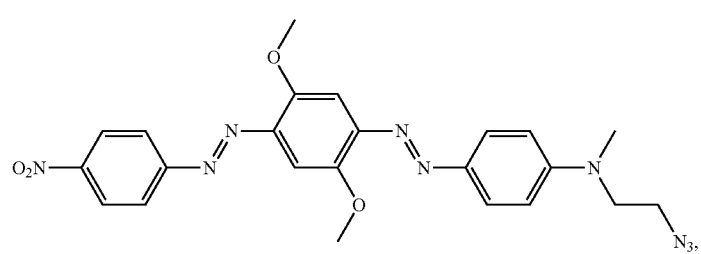
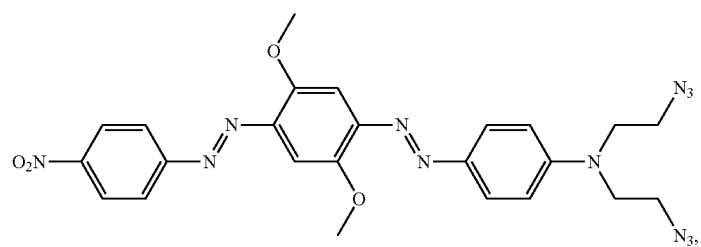

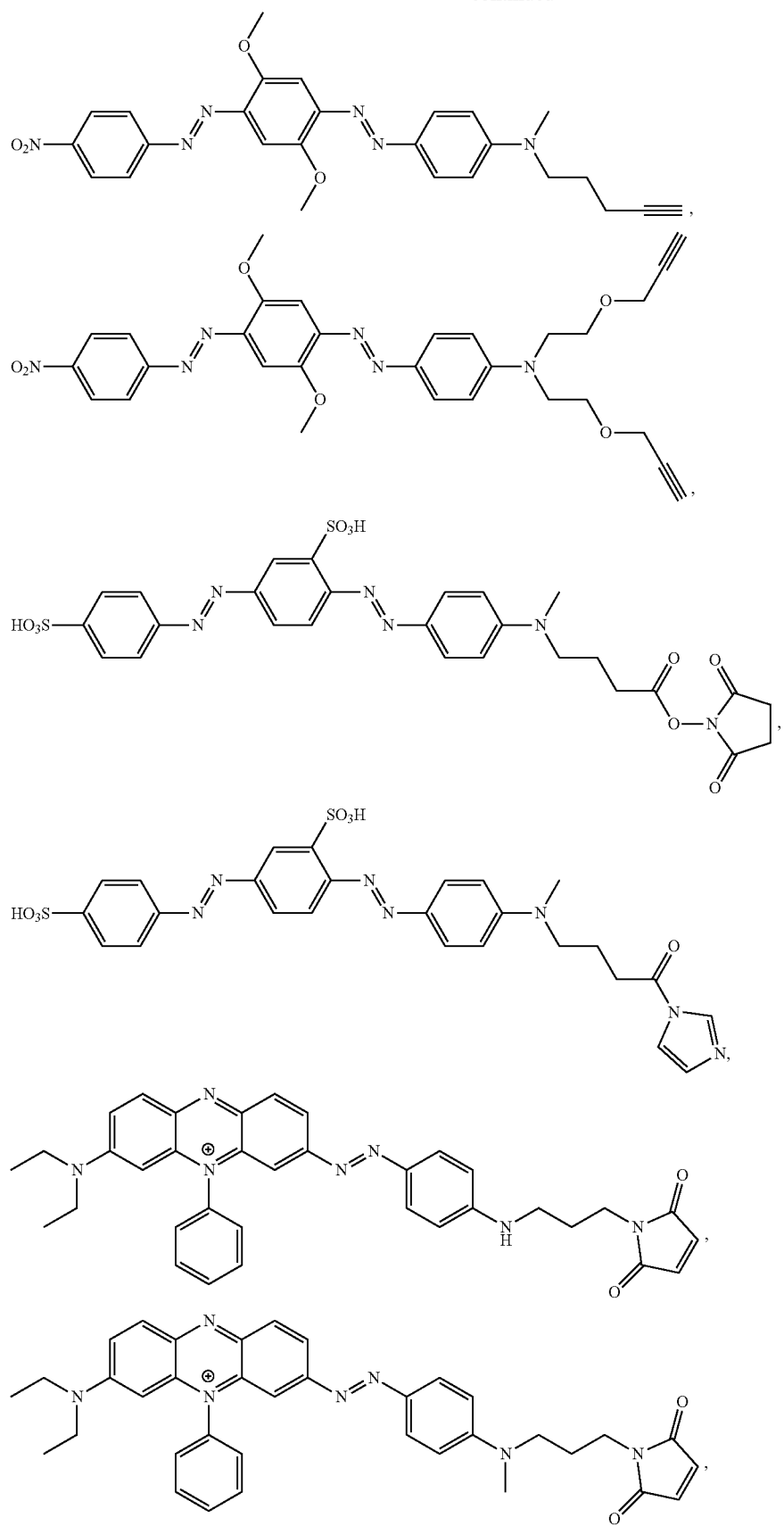

-continued
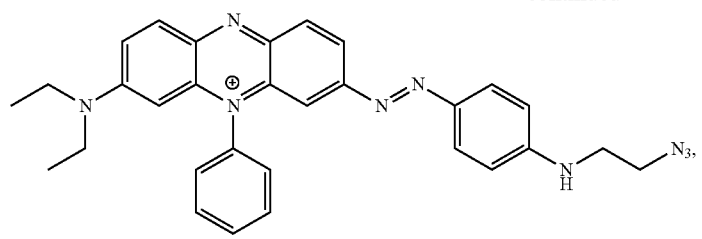
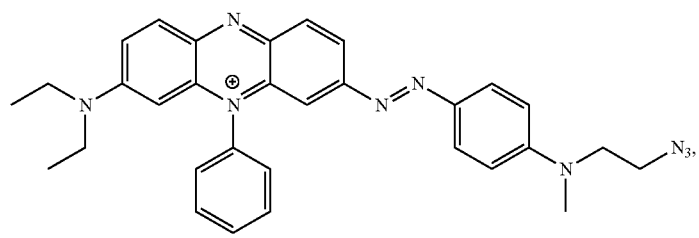
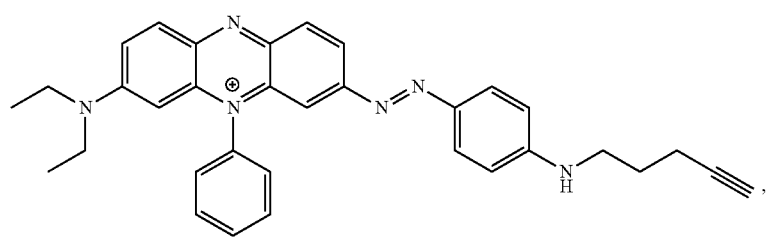
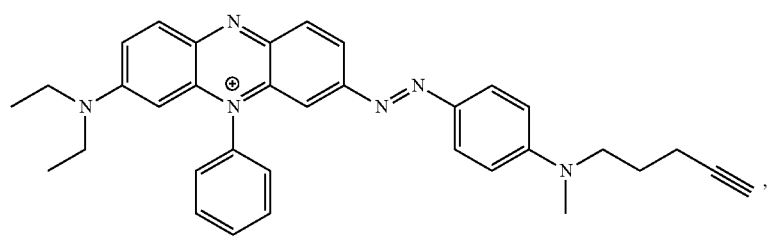
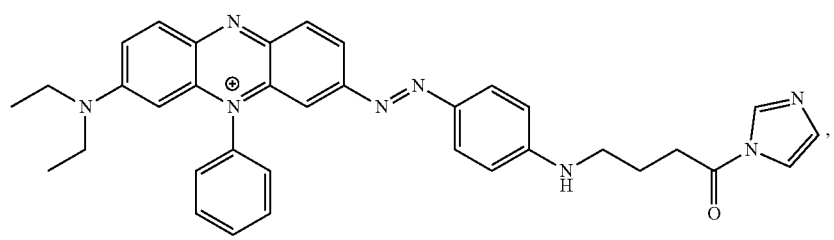
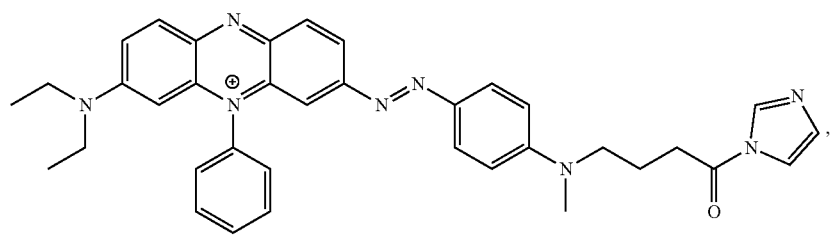
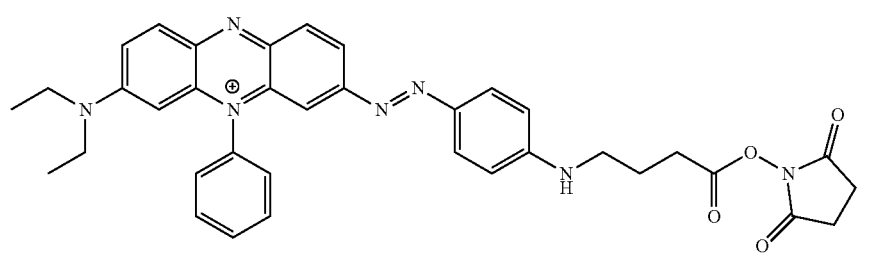
and

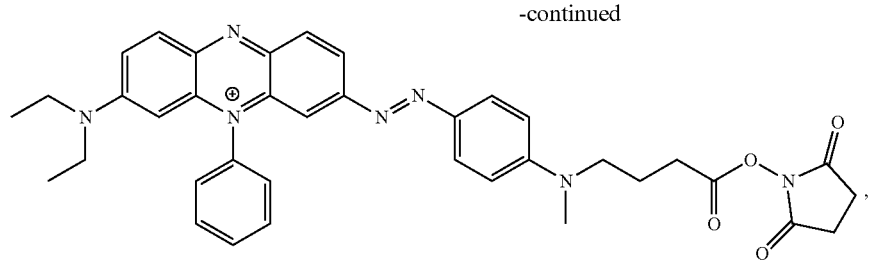
and any salt thereof.
In certain embodiments, the quencher is a compound selected from the group consisting of:
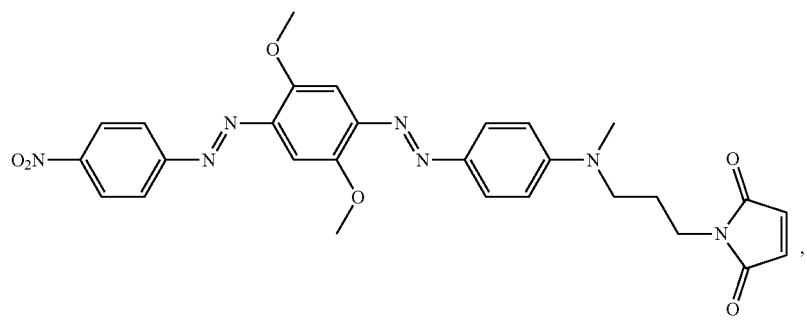
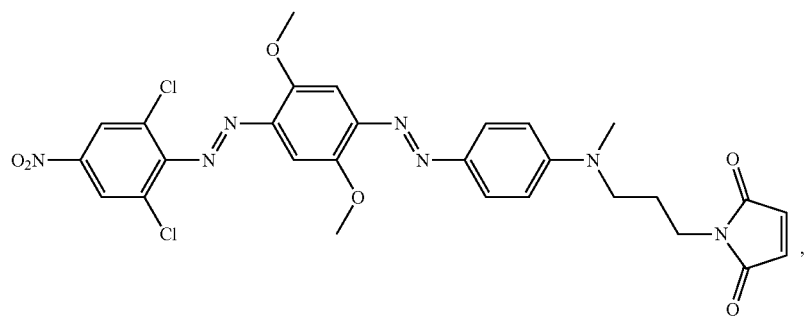
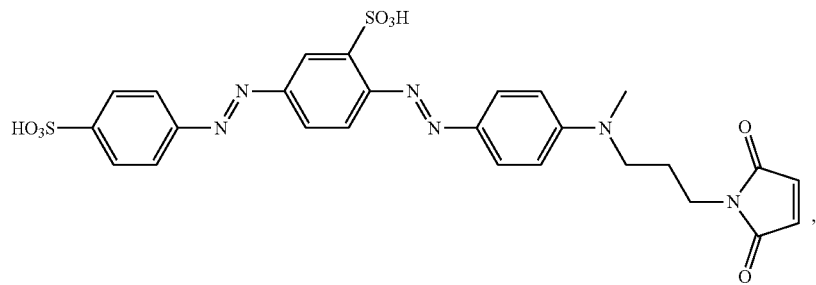

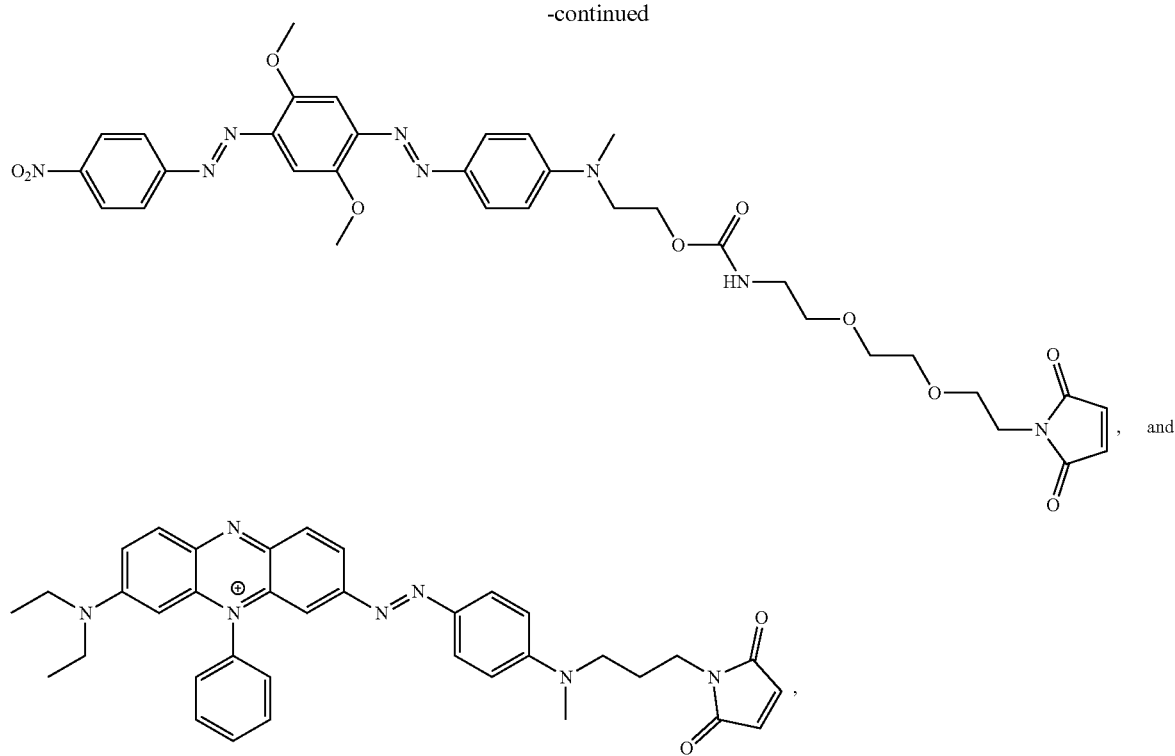

and any salt thereof.

In yet another aspect, the present disclosure also provides compounds of formula (I), formula (II), or a salt thereof, as described above, compositions, combinations, and kits thereof, as well as methods of preparing such compounds, and any intermediates for the same.

In any of the embodiments herein, "alkyl", by itself or as part of another substituent, comprises, unless otherwise stated, a straight or branched chain hydrocarbon radical, having the number of carbon atoms designated (e.g., $C_1$-$C_6$ means one to six carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. In some embodiments, the term "alkyl" may encompass $C_1$-$C_6$ alkyl, $C_2$-$C_6$ alkyl, $C_3$-$C_6$ alkyl, $C_4$-$C_6$ alkyl, $C_5$-$C_6$ alkyl, $C_1$-$C_5$ alkyl, $C_2$-$C_5$ alkyl, $C_3$-$C_5$ alkyl, $C_4$-$C_5$ alkyl, $C_1$-$C_4$ alkyl, $C_2$-$C_4$ alkyl, $C_3$-$C_4$ alkyl, $C_1$-$C_3$ alkyl, $C_2$-$C_3$ alkyl, or $C_1$-$C_2$ alkyl.

In any of the embodiments herein, "alkoxy" and "alkylamino" are used in their conventional sense, and comprise those alkyl groups attached to the remainder of the molecule via an oxygen atom or an amino group, respectively.

In any of the embodiments herein, the terms "halo" or "halogen," by themselves or as part of another substituent, comprise, unless otherwise stated, a fluorine, chlorine, bromine, or iodine atom or ion. In some embodiments, terms such as "haloalkyl" comprise monohaloalkyl or polyhaloalkyl. For example, the term "$C_1$-$C_4$ haloalkyl" may comprise trifluoromethyl, 2,2,2-trifluoroethyl, 4-chlorobutyl, 3-bromopropyl, difluoromethyl, or the like.

In any of the embodiments herein, the terms "hydroxyalkylene" or "alkyl-OH" comprise an alkyl substituted by one or more hydroxyl groups. The terms may comprise alkyl substituted by one hydroxyl group, or alkyl substituted by multiple hydroxyl groups. For example, the term "alkyl-OH" may comprise —$CH_2OH$, —$CH(OH)CH_3$, —$CH_2CH_2OH$, or the like.

In any of the embodiments herein, the term "aryl" comprises, unless otherwise stated, a polyunsaturated, aromatic, hydrocarbon group, which can be a single ring or multiple rings (up to three rings) which are fused together. In some embodiments, "aryl" comprises $C_6$-$C_{14}$ aryl, $C_8$-$C_{14}$ aryl, $C_{10}$-$C_{14}$ aryl, $C_{12}$-$C_{14}$ aryl, $C_6$-$C_{12}$ aryl, $C_8$-$C_{12}$ aryl, $C_{10}$-$C_{12}$ aryl, $C_6$-$C_{20}$ aryl, $C_8$-$C_{10}$ aryl, or $C_6$-$C_8$ aryl. In some embodiments, a typical aryl comprises $C_6$-$C_{20}$ aryl. Non-limiting examples of aryl groups include phenyl, naphthyl and biphenyl.

In any of the embodiments herein, "heteroaryl" comprises an aromatic ring containing the indicated number of atoms (e.g., 5 to 20, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. In some embodiments, the term "heteroaryl" may comprise 5- to 10-membered heteroaryl, 6- to 10-membered heteroaryl, 7- to 10-membered heteroaryl, 8- to 10-membered heteroaryl, 9- to 10-membered heteroaryl, 5- to 9-membered heteroaryl, 6- to 9-membered heteroaryl, 7- to 9-membered heteroaryl, 8- to 9-membered heteroaryl, 5- to 8-membered heteroaryl, 6- to 8-membered heteroaryl, 7- to 8-membered heteroaryl, 5- to 7-membered heteroaryl, 6- to 7-membered heteroaryl, or 5- to 6-membered heteroaryl. In some embodiments, heteroaryl is a monocyclic ring. In some embodiments, heteroaryl is a bicyclic fused ring. In some embodiments, heteroaryl is a tricyclic fused ring. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

The above terms (e.g., "alkyl," "aryl" and "heteroaryl"), in some embodiments, will include both substituted and unsubstituted forms of the indicated radical. In any of the embodiments herein, the term "substituted" comprises that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. In any of the embodiments herein the term "unsubstituted" comprises that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

In any of the embodiments herein, by "optional" or "optionally" means that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

In any of the embodiments herein, salts comprise salts of the compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19, the content of which is herein incorporated by reference in its entirety). In any of the embodiments herein, certain specific compounds of the present disclosure contain both basic and acidic functionalities that allow the compounds to be converted into either base or acid addition salts.

In any of the embodiments herein, the neutral forms of the compounds can be regenerated by contacting the salt with a base or acid and isolating the parent compound in the conventional manner. In any of the embodiments herein, the parent form of the compound may differ from the various salt forms in certain physical properties, such as solubility in polar solvents, but otherwise the salts are equivalent to the parent form of the compound for the purposes of the present disclosure.

(vi) Concentration

In some embodiments of the present disclosure, the biological samples or tissue samples to be analyzed may be treated with a quencher at specific concentration. The concentration of quencher applied to the samples may be optimized to achieve the desired reduction on background autofluorescence without substantially reducing the fluorescence signal associated with the molecule or analyte of interest.

In some embodiments, the methods of the present disclosure comprise contacting the biological sample with the quencher, wherein the quencher is provided in DMSO solution at a concentration of at least about 0.01 mM, at least about 0.02 mM, at least about 0.05 mM, at least about 0.07 mM, at least about 0.1 mM, at least about 0.2 mM, at least about 0.3 mM, at least about 0.4 mM, or at least about 0.5 mM. In some embodiments, the methods of the present disclosure comprise contacting the biological sample with the quencher, wherein the quencher is provided in DMSO solution at a concentration of less than or equal to about 2 mM, less than or equal to about 1.7 mM less than or equal to about 1.5 mM, less than or equal to about 1.2 mM, less than or equal to about 1.1 mM, or less than or equal to about 1 mM. In other embodiments, the methods of the present disclosure comprise contacting the biological sample with the quencher, wherein the quencher is provided in DMSO solution at a concentration of less than or equal to about 0.8 mM, less than or equal to about 0.7 mM, less than or equal to about 0.6 mM, less than or equal to about 0.5 mM, or less than or equal to about 0.4 mM. In certain embodiments, the methods of the present disclosure comprise contacting the biological sample with the quencher, wherein the quencher is provided in DMSO solution at a concentration of between about 0.01 mM and about 0.8 mM, between about 0.05 mM and about 0.8 mM, between about 0.1 mM and about 0.8 mM, between about 0.1 mM and about 0.7 mM, between about 0.1 mM and about 0.6 mM, between about 0.1 mM and about 0.5 mM, between about 0.1 mM and about 0.4 mM, between about 0.2 mM and about 0.8 mM, between about 0.2 mM and about 0.7 mM, between about 0.2 mM and about 0.6 mM, between about 0.2 mM and about 0.5 mM, between about 0.2 mM and about 0.4 mM, between about 0.3 mM and about 0.8 mM, between about 0.3 mM and about 0.7 mM, between about 0.3 mM and about 0.6 mM, between about 0.3 mM and about 0.5 mM, between about 0.3 mM and about 0.4 mM, between about 0.4 mM and about 0.8 mM, between about 0.4 mM and about 0.7 mM, between about 0.4 mM and about 0.6 mM, or between about 0.4 mM and about 0.5 mM.

Certain concentrations of quencher may also be observed as resulting in certain reductions in autofluorescence background, increases in signal-to-noise ratio or increase in the detectable object density. In some embodiments, the autofluorescence background is reduced by at least about 20%, at least about 30%, at least about 40%, or at least about 50% when the concentration of quencher is at least about 0.05 mM. In certain embodiments, the autofluorescence background is reduced by at least 20%, at least about 30%, at least about 40%, or at least about 50% when the quencher is Compound 1A and the concentration of quencher is at least about 0.05 mM. In other embodiments, the signal-to-noise ratio is increased by at least about 5%, at least about 7%, at least about 10%, at least about 12% or at least about 15% when the concentration of quencher is at least about 0.05 mM. In certain other embodiments, the signal-to-noise ratio is increased by at least about 5%, at least about 7%, at least about 10%, at least about 12% or at least about 15% when the quencher is Compound 1A and the concentration of quencher is at least about 0.05 mM. In some embodiments, the detectable object density is increased by at least 2 times, at least 3 times, at least 4 times, or at least 5 times when the concentration of the quencher is about 0.8 mM. In certain embodiments, the detectable object density is increased by at least 2 times, at least 3 times, at least 4 times, or at least 5 times when the quencher is Compound 1A and the concentration of the quencher is about 0.8 mM.

C. Endogenous Biological Moiety

In some embodiments, the endogenous biological moieties present in the biological or tissue samples as described herein are autofluorescent or are associated with or proximal to another endogenous biological moiety that is autofluorescent. In some embodiments, the endogenous biological moiety is autofluorescent. An endogenous biological moiety that is autofluorescent may also be referred to herein as "an autofluorescent moiety".

In some embodiments, the endogenous biological moiety is selected from the group consisting of lipofuscin, collagen, elastin, red blood cells, flavins, nicotinamide adenine dinucleotide (NADH) and the extracellular matrix. In some embodiments, the endogenous biological moiety is lipofuscin. In other embodiments, the endogenous biological moiety is collagen. In some embodiments, the endogenous biological moiety is elastin. In other embodiments, the endogenous biological moiety are red blood cells. In yet other embodiments, the endogenous biological moiety are flavins. In yet other embodiments, the endogenous biological moiety is nicotinamide adenine dinucleotide. In still yet other embodiments, the endogenous biological moiety is the extracellular matrix. It should be recognized that various biological samples and tissue samples may comprise one or more of the aforementioned endogenous biological moieties. It should also be recognized that certain tissue types may comprise combinations of certain endogenous biological moieties which differentiate the tissue type from other tissue types.

As described herein, the methods for reducing autofluorescence and for analyzing a biological sample or a tissue sample employ quenchers having targeting moieties that reacts or binds to an endogenous biological moiety present in the biological sample or tissue sample. The resulting interaction between the targeting moiety and the endogenous biological moiety provides a durable linkage between the quencher and the endogenous biological moiety, even after several cycles of washing, stripping and dehybridization. In some embodiments wherein the quencher remains in the biological sample or the tissue sample after removal of the detectable probe, the quencher remains targeted to the endogenous biological moiety. In some embodiments, the presence of the quencher may be observed visually and confirmed. In still other embodiments, the presence of the quencher is observed by virtue of the sustained decrease in autofluorescence background, sustained increase in signal-to-noise ratio, and/or sustained increase in detected object density over multiple cycles of washing, stripping, dehybridization and imaging.

(i) Interaction Between Targeting Moiety and Endogenous Biological Moiety Via Second Functional Groups The targeting moieties of the quencher as described herein may interact via formation of a covalent bond or via intermolecular attraction.

In some embodiments, the targeting moiety comprises a first functional group, and the endogenous biological moiety comprises a second functional group capable of reacting with the first functional group to form a covalent bond. As detailed above for the targeting moiety, the targeting moieties may comprise a first functional group which can form covalent bonds with the endogenous biological moieties via a second functional group on the endogenous biological moiety. Suitable second functional groups may include but are not limited to amines, thiols, hydroxyls, alkenes, alkynes or azides. It should be recognized that the second functional group present on the endogenous biological moieties may vary with the type of endogenous biological moiety being targeted and that the first functional group on the targeting moiety will be selected to complement the reactivity of the second functional group to enable formation of a covalent bond. The mechanism for covalent bond formation may include but is not limited to such reaction types as nucleophilic or electrophilic substitution or cycloaddition. For example, in some embodiments wherein the second functional group is an amine, the first functional group of the targeting moiety is a carboxylic acid or derivative thereof. In other embodiments wherein the second functional group is a thiol, the first functional group is a maleimide. In yet other embodiments wherein the second functional group is an alkyne, the first functional group is an azide.

(ii) Enrichment of Second Functional Groups

In some embodiments, the second functional groups may be native to the endogenous biological moieties in a protected or precursor form, but may require enrichment to increase the concentration of or introduction of the second functional group in the sample. In some embodiments, the methods of the present disclosure comprise a step of treating the biological sample or tissue sample to enrich, create and/or introduce the second functional group in the endogenous biological moiety.

For example, the biological sample or tissue sample may contain a precursor to the second functional group, which is not available to form covalent bonds with the first functional group until being exposed, such as a disulfide bond which can be reduced by any suitable reducing agents to enrich the concentration of free thiol groups as the second functional group. In some embodiments, the second functional group is thiol, and the biological sample or tissue sample is treated with a reducing agent to convert disulfide groups to thiol groups. In certain embodiments, the reducing agent is dithiothreitol (DTT) or tris(2-carboxyethyl)phosphine (TCEP). In certain other embodiments wherein the second functional group is thiol, and the biological sample or tissue sample is treated with a reducing agent to convert disulfide groups to thiol groups, the first functional group is maleimide.

An endogenous biological moiety may comprise two or more independent second functional groups, such as an amine and a thiol, or it may be desired to target two endogenous biological moieties having different available functional groups, such as collagen and red blood cells. In such instances, additional treatment to convert the functional groups present on the endogenous biological moiety or moieties to the same second functional group. Suitable treatments may include the introduction of a heterobifunctional crosslinker. For example, in some embodiments, the endogenous biological moiety comprises a third functional group, which is different from the second functional group, and wherein the biological sample or tissue sample is treated with a heterobifunctional crosslinker comprising the second functional group and a fourth functional group capable of reacting with the third functional group to form a covalent bond, thereby introducing the second functional group in the endogenous biological moiety. In certain embodiments, the third functional group is an amine and the second functional group is thiol. In certain other embodiments wherein the third functional group is an amine and the second functional group is thiol, the heterobifunctional crosslinker is succinimidyl 3-(2-pyridyldithio)propionate (SPDP) or a derivative thereof. In certain embodiments, the heterobifunctional crosslinker is 2,5-dioxopyrrolidin-1-yl 3-oxo-1-(pyridin-2-yldisulfaneyl)-7,10,13,16-tetraoxa-4-azanonadecan-19-oate (PEG4-SPDP).

D. Detection

As detailed herein, the methods of the present disclosure comprise a step or multiple steps of detecting a signal associated with a detectable probe or one or more signals associated with one or more detectable probes. The signal associated with the detectable probe(s) is a fluorescence signal, which becomes observable or becomes more readily observable after quenching to reduce autofluorescence according to the methods describe herein.

(i) Detectable Probes

The detectable probes (e.g., fluorescently labeled detectable probes) may themselves contain a fluorescent moiety or may bind or hybridize to an additional probe containing a fluorescent moiety. In some embodiments of any of the preceding aspects, each detectable probe is independently detectably labeled or hybridizes to a detectably labeled probe. In certain embodiments, each detectable probe is independently covalently labeled with a fluorophore or hybridizes to a probe covalently labeled with a fluorophore.

In some embodiments, the molecule of interest is a nucleic acid of interest or a protein of interest. In certain embodiments wherein the molecule of interest is a nucleic acid of interest, the detectable probe hybridizes to the nucleic acid of interest. In certain other embodiments, the detectable probe hybridizes to one or more intermediate probes which directly or indirectly bind to the nucleic acid of interest. In yet other embodiments, the detectable probe hybridizes to one or more intermediate probes which in turn hybridize to the nucleic acid of interest.

In other embodiments, the methods further comprise adding a primary probe prior to adding the detectable probe and one or more intermediate probes, wherein the intermediate probe binds to the primary probe or a product thereof. In some embodiments, the primary probe is a nucleic acid probe that directly or indirectly binds to a cellular or viral DNA or RNA or a product thereof. In other embodiments, the intermediate probe is a nucleic acid probe that hybridizes to the primary probe or a product thereof, wherein the primary probe is a nucleic acid probe.

In some embodiments, the signals associated with one or more detectable probes are associated with a probe that is linear, circularizable, circular, or in a branched complex of hybridized probes (e.g., various probes and amplification methods are described in Section III-V). In some embodiments, a probe that binds to the target analyte directly or indirect or to a primary nucleic acid probe or a product thereof directly or indirectly (e.g., an amplification product) comprises a detectable label that may be detected and associated with the analyte of interest. In some embodiments, the barcode sequences (e.g., in a probe or a product thereof) are used to combinatorially encode a plurality of analytes of interest. As such, signals associated with the detectably labeled probes at particular locations in a biological sample can be used to generate distinct signal signatures through a plurality of hybridization cycles that each corresponds to an analyte in the sample, thereby identifying the analytes at the particular locations.

(ii) Imaging and Detection Wavelengths

In some embodiments, the methods comprise a step of detecting a signal associated with the detectable probe bound to the molecule of interest comprises imaging at one or more wavelengths between about 400 nm and about 700 nm. In some embodiments, the one or more wavelengths are selected from the group consisting of 488 nm, 532 nm, 561 nm, 590 nm, 640 nm, and 647 nm.

(iii) Improvement in Background Autofluorescence, Signal-to-Noise Ratio, and/or Detectable Object Density As described herein, the methods of the present disclosure reduce background autofluorescence in a single-step application of quencher to provide improved fluorescence imaging as compared to unquenched samples. The improvements in imaging may be observed as long-lasting reductions in background autofluorescence levels, increased signal-to-noise ratios, and even increased detectable object count densities as compared to unquenched tissue samples.

Unquenched biological sample or unquenched tissue sample is understood to be a biological sample or tissue sample of the same type having undergone identical treatments as the quenched sample excepting treatment with the quencher comprising a quencher dye and a targeting moiety, as described herein. It should also be recognized that comparison of autofluorescence background intensity, signal-to-noise ratio, detectable object count density, and/or fluorescence intensity of detectable probes refers to comparison of the characteristic metric at the same wavelength.

The methods of the present disclosure can also achieve these improvements to the detection without substantially reducing the fluorescence signal associated with the detectable probe by virtue of the targeted quenching of autofluorescent moieties. The preservation of fluorescent signal associated with the detectable probe distinguishes the methods of the present disclosure from other techniques such as FRET, wherein the quenching of a fluorescence associated with an analyte of interest is the signal to be measured.

In any of the embodiments herein, the term "autofluorescence" is used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Reduction of autofluorescence may manifest or be characterized by a reduction in the average detected light intensity or detector photoelectron counts for a biological sample. In some embodiments, the autofluorescence of the biological sample is reduced as compared to an unquenched biological sample. In certain embodiments, the autofluorescence is reduced by at least about 50%, at least about 60%, at least about 70% or at least about 80% as compared to an unquenched biological sample. In some embodiments, the autofluorescence of the tissue sample is reduced as compared to an unquenched tissue sample. In certain embodiments, the autofluorescence is reduced by at least about 50%, at least about 60%, at least about 70% or at least about 80% as compared to an unquenched tissue sample.

In some embodiments, the quencher reduces the autofluorescence of the biological sample without substantially reducing the signal associated with the detectable probe. In certain embodiments, the quencher reduces the autofluorescence of the tissue sample without substantially reducing the signal associated with the detectable probe.

In some embodiments, the combination of the reduction of the background autofluorescence and the preservation of the signal intensity associated with the detectable probes arising from the targeted quenching herein may result in improvements in signal-to-noise ratios. In any of the embodiments herein, the phrase "signal-to-noise ratio" (or SNR or S/N) is a comparison of the level of desired signal (e.g., fluorescence signal associated with detectable probe) to the level of background noise. In other embodiments, the signal-to-noise ratio is increased as compared to an unquenched biological sample. In certain embodiments, the signal-to-noise ratio is increased by at least about 10%, at least about 20%, at least about 25%, at least about 30%, at least about 35% or at least about 40% as compared to an unquenched biological sample. In other embodiments, the signal-to-noise ratio is increased as compared to an unquenched tissue sample. In certain embodiments, the signal-to-noise ratio is increased by at least about 10%, at least about 20%, or at least about 25% as compared to an unquenched tissue sample.

In other embodiments, the reduction of background autofluorescence may also allow for observation of low intensity signals, which might otherwise have been obscured by autofluorescence. This improvement in imaging may be characterized by increases in detectable object count density. In any of the embodiments herein, the phrase "detectable object count density", "detectable object density", or "detected object density" is a measure of the number of objects (e.g., fluorescent objects) that can be detected for a given area of a biological sample. In some embodiments, the given area of the biological sample is a nucleus area, for example, as measured by DAPI staining, and the detectable object count density is the detected object count per unit nuclei area (e.g., object count/$\mu m^2$ nuclei area) in cells of the biological sample. In some embodiments, the detectable object count density is increased as compared to an unquenched biological sample. In certain embodiments, the detectable object count density is increased by at least about 2 times, at least about 3 times, at least about 4 times, or at least about 5 times as compared to an unquenched biological sample. In some embodiments, the detectable object count density is increased as compared to an unquenched tissue sample. In certain embodiments, the detectable object count density is increased by at least about 2 times, at least about 3 times, at least about 4 times, or at least about 5 times as compared to an unquenched tissue sample.

Similar to the above improvements observed for detection of signal associated with detectable probes in one imaging cycle, improvements to the imaging as determined by reductions in autofluorescence, increases in signal-to-noise ratios and/or increases in detectable object count density may also be measured when one or more additional probes are detected in one or more cycles. Any reductions in autofluorescence, increases in signal-to-noise ratios and/or increases in detectable object count density may be characterized relative to an unquenched tissue sample having undergone the same number of imaging cycles, or relative to the prior value for the preceding cycle for the quenched sample.

In some embodiments, after a given cycle, the quencher remains in the biological sample and autofluorescence of the biological sample remains reduced as compared to an unquenched biological sample. In certain embodiments, after a given cycle, the quencher remains in the tissue sample and autofluorescence of the tissue sample remains reduced as compared to an unquenched tissue sample.

In some embodiments, after a given cycle, the quencher remains in the biological sample and autofluorescence of the biological sample remains reduced as compared to an unquenched biological sample. In some embodiments, the autofluorescence remains reduced by at least about 50%, at least about 60%, at least about 70% or at least about 80% for a given cycle as compared to an unquenched biological sample. In other embodiments, the autofluorescence increases by less than about 5%, less than about 10% or less than about 15% for a given cycle as compared to the preceding cycle. In some embodiments, after a given cycle, the quencher remains in the tissue sample and autofluorescence of the tissue sample remains reduced as compared to an unquenched tissue sample. In some embodiments, the autofluorescence remains reduced by at least about 50%, at least about 60%, at least about 70% or at least about 80% for a given cycle as compared to an unquenched tissue sample. In other embodiments, the autofluorescence increases by less than about 5%, less than about 10% or less than about 15% for a given cycle as compared to the preceding cycle.

In some embodiments, after a given cycle, the signal-to-noise ratio remains increased as compared to an unquenched biological sample. In some embodiments, the signal-to-noise ratio remains increased by at least about 10%, at least about 20%, or at least about 25% for a given cycle as compared to an unquenched biological sample. In some embodiments, the signal-to-noise ratio decreases by less than about 5%, less than about 10% or less than about 15% for a given cycle as compared to the preceding cycle. In some embodiments, after a given cycle, the signal-to-noise ratio remains increased as compared to an unquenched tissue sample. In some embodiments, the signal-to-noise ratio remains increased by at least about 10%, at least about 20%, or at least about 25% for a given cycle as compared to an unquenched tissue sample. In some embodiments, the signal-to-noise ratio decreases by less than about 5%, less than about 10% or less than about 15% for a given cycle as compared to the preceding cycle.

In some embodiments, the detectable object count density remains increased for a given cycle as compared to an unquenched biological sample. In certain embodiments, the detectable object count density remains increased by at least about 2 times, at least about 3 times, at least about 4 times, or at least about 5 times for a given cycle as compared to an unquenched biological sample. In certain other embodiments, the detectable object count density decreases by less than about 5%, less than about 10% or less than about 15% for a given cycle as compared to the preceding cycle. In some embodiments, the detectable object count density remains increased for a given cycle as compared to an unquenched tissue sample. In certain embodiments, the detectable object count density remains increased by at least about 2 times, at least about 3 times, at least about 4 times, or at least about 5 times for a given cycle as compared to an unquenched tissue sample. In certain other embodiments, the detectable object count density decreases by less than about 5%, less than about 10% or less than about 15% for a given cycle as compared to the preceding cycle.

II. Samples, Analytes, and Target Sequences

A. Samples and Sample Processing

A sample disclosed herein can be or derived from any biological sample. In some embodiments, a sample herein is one in which analysis of target molecules and their position in two- or three-dimensional space is desired. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The biological sample can be obtained as a population of cells, for instance, dissociated cells obtained from a tissue sample or a cell culture. The dissociated cells can be deposited and/or immobilized on a substrate, for instance, for analysis using a platform for in situ detection of one or more analytes in the cells. The sample can be a fluid sample, such as a blood sample, urine sample, or saliva sample, and cells and cellular components therein may be analyzed after placing the cells or cellular components on a substrate. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface and the cells can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include target molecules (e.g., protein, RNA, and/or DNA) in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

The biological sample within the 3D matrix may be cleared of proteins and/or lipids that are not targets of interest. For example, the biological sample can be cleared of proteins (also called "deproteination") by enzymatic proteolysis. The clearing step may be performed before or after covalent immobilization of any target molecules or derivatives thereof.

In some cases, the clearing step is performed after covalent immobilization of target molecules (e.g., RNA or DNA), primers, derivatives of target molecules (e.g., cDNA or amplicons), or probes to a synthetic 3D matrix. Performing the clearing step after immobilization can enable any subsequent nucleic acid hybridization reactions to be performed under conditions where the sample has been substantially deproteinated, as by enzymatic proteolysis ("protein clearing"). This method can have the benefit of removing ribosomes and other RNA- or nucleic-acid-target-binding proteins from the target molecule (while maintaining spatial location), where the protein component may impede or inhibit probe binding.

The clearing step can comprise removing non-targets from the 3D matrix. The clearing step can comprise degrading the non-targets. The clearing step can comprise exposing the sample to an enzyme (e.g., a protease) able to degrade a protein. The clearing step can comprise exposing the sample to a detergent.

Proteins may be cleared from the sample using enzymes, denaturants, chelating agents, chemical agents, and the like, which may break down the proteins into smaller components and/or amino acids. These smaller components may be easier to remove physically, and/or may be sufficiently small or inert such that they do not significantly affect the background. Similarly, lipids may be cleared from the sample using surfactants or the like. In some cases, one or more of these agents are used, e.g., simultaneously or sequentially. Non-limiting examples of suitable enzymes include proteinases such as proteinase K, proteases or peptidases, or digestive enzymes such as trypsin, pepsin, or chymotrypsin. Non-limiting examples of suitable denaturants include guanidine HCl, acetone, acetic acid, urea, or lithium perchlorate. Non-limiting examples of chemical agents able to denature proteins include solvents such as phenol, chloroform, guanidinium isocyanante, urea, formamide, etc. Non-limiting examples of surfactants include Triton X-100 (polyethylene glycol p-(1,1,3,3-tetramethylbutyl)-phenyl ether), SDS (sodium dodecyl sulfate), Igepal CA-630, or poloxamers. Non-limiting examples of chelating agents include ethylenediaminetetraacetic acid (EDTA), citrate, or polyaspartic acid. In some embodiments, compounds such as these may be applied to the sample to clear proteins, lipids, and/or other components. For instance, a buffer solution (e.g., containing Tris or tris(hydroxymethyl)aminomethane) may be applied to the sample, then removed.

In some cases, nucleic acids that are not target molecules of interest may also be cleared. These non-target nucleic acids may be removed with an enzyme to degrade nucleic acid molecules. Non-limiting examples of DNA enzymes that may be used to remove DNA include DNase I, dsDNase, a variety of restriction enzymes, etc. Non-limiting examples of techniques to clear RNA include RNA enzymes such as RNase A, RNase T, or RNase H, or chemical agents, e.g., via alkaline hydrolysis (for example, by increasing the pH to greater than 10). Non-limiting examples of systems to remove sugars or extracellular matrix include enzymes such as chitinase, heparinases, or other glycosylases. Non-limiting examples of systems to remove lipids include enzymes such as lipidases, chemical agents such as alcohols (e.g., methanol or ethanol), or detergents such as Triton X-100 or sodium dodecyl sulfate. In this way, the background of the sample may be removed, which may facilitate analysis of the nucleic acid probes or other targets, e.g., using fluorescence microscopy, or other techniques as described herein.

In some embodiments, a sample disclosed herein may be provided on a substrate. In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

In some embodiments of the methods provided herein, the biological sample is a tissue sample. The methods for reducing autofluorescence and analyzing a biological sample as detailed herein are especially suitable for tissue samples which contain a wide range of endogenous biological moieties that can contribute to background autofluorescence.

In some embodiments, the tissue sample is melanoma tissue, brain tissue, lung tissue, tonsil tissue, intestinal tissue, kidney tissue, spleen tissue, liver tissue, breast tissue, or liver tissue. Certain tissue types, including but not limited to brain, liver and tonsil tissue samples, are predisposed to displaying high levels of background fluorescence and may benefit from the methods as detailed herein for reducing autofluorescence and analyzing tissue samples. In certain embodiments, the tissue sample is brain tissue, liver tissue or tonsil tissue.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes. In some embodiments, one or more post-fixing step is performed after a hybridization complex comprising a probe and a target is formed in a sample.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

Fixation reagents may induce or exacerbate autofluorescence in tissue samples. Accordingly, the methods of the present disclosure for reducing autofluorescence and analyzing a biological sample, such as a tissue sample, as provided herein are also suited for applications to samples which have been subjected to a fixation step. In some embodiments, the tissue sample is a formalin-fixed tissue sample or a formalin-fixed paraffin-embedded (FFPE) sample. In some embodiments, the autofluorescence is fixative-induced autofluorescence.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed, e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). In some aspects, the embedding material can be applied to the sample one or more times. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other suitable hydrogel-formation methods.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., Science 347(6221):543-548, 2015, US2016/0024555, US2019/0276881, US2020/0071751, WO2020/0076976, WO2020/0076979, and WO2020/0096687, the entire contents of which are incorporated herein by reference. Tissue or cell samples can be embedded within conductive hydrogels. U.S. Pat. Publ. No. 2011/0256183 (Frank et al.), U.S. Pat. No. 10,138,509 (Church et al.), U.S. Pat. No. 10,545,075 (Deisseroth et al.) and U.S. Pat. Publ. No. 2019/0233878 (Delaney, et al.) which are herein incorporated by reference, describe hydrogels and their use for embedding tissues and cells.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g., DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranin, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained using any suitable methods of destaining or discoloring a biological sample, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015, the content of which is herein incorporated by reference in its entirety.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly or irreversibly cross-linked prior to, during, or after an assay step disclosed herein.

In some aspects, the analytes, polynucleotides and/or amplification product (e.g., amplicon) of an analyte or a probe bound thereto can be anchored to a polymer matrix. For example, the polymer matrix can be a hydrogel. In some embodiments, the polymer matrix comprises functional moieties. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other suitable hydrogel-formation methods. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by any suitable non-chemical permeabilization methods. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques,* 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some embodiments, any of the target nucleic acid molecules described herein can correspond to an analyte. For instance, a target nucleic acid molecule can be an endogenous nucleic acid analyte (e.g., DNA or RNA), a product of an endogenous nucleic acid analyte, a probe that directly or indirectly binds to an endogenous nucleic acid analyte, or a product of a probe that directly or indirectly binds to an endogenous nucleic acid analyte. In some aspects, an analyte can include any biological substance, structure, moiety, or component to be analyzed. In some embodiments, any of the target nucleic acid molecules described herein can correspond to an analyte. For instance, a target nucleic acid molecule can be an endogenous nucleic acid analyte (e.g., DNA or RNA), a product of an endogenous nucleic acid analyte, a probe that directly or indirectly binds to an endogenous nucleic acid analyte, or a product of a probe that directly or indirectly binds to an endogenous nucleic acid analyte. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific subcellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template. Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes or Molecules of Interest

In some embodiments, a target molecule herein corresponds to an analyte that is endogenous to a biological sample and can include nucleic acid analytes and non-nucleic acid analytes. In some embodiments, the endogenous analytes as detailed herein may also be referred to as analytes of interest or molecules of interest. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence. In some embodiments, the analytes comprises one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

In some embodiments, the molecule of interest is a nucleic acid of interest or a protein of interest. In some embodiments, the molecule of interest is a nucleic acid of interest.

In some embodiments, the nucleic acid of interest is a cellular or viral DNA or RNA or a product thereof. In certain embodiments, the cellular or viral DNA or RNA or product thereof is a genomic DNA, a coding RNA, a non-coding RNA, or a cDNA. In certain other embodiments, the nucleic acid of interest is an mRNA.

In some embodiments, the nucleic acid of interest is a nucleic acid probe that directly or indirectly binds to a cellular or viral DNA or RNA or a product thereof. In certain embodiments, the cellular or viral DNA or RNA or product thereof is a genomic DNA, a coding RNA, a non-coding RNA, or a cDNA. In certain other embodiments, the coding RNA is an mRNA. In some embodiments, the nucleic acid probe is linear, circularizable, circular, or branched. In certain embodiments, the nucleic acid probe comprises a 3' overhang and/or a 5' overhang upon hybridization to the cellular or viral DNA or RNA or product thereof. In some embodiments, the nucleic acid probe comprises one or more barcode regions.

In other embodiments, the nucleic acid of interest is a probe product of one or more nucleic acid probes that directly or indirectly bind to a cellular or viral DNA or RNA or a product thereof. In certain embodiments, the cellular or viral DNA or RNA or product thereof is a genomic DNA, a coding RNA, a non-coding RNA, or a cDNA. In certain other embodiments, the coding RNA is an mRNA. In some embodiments, the probe product is a rolling circle amplification (RCA) product, a hybridization chain reaction (HCR) product, a linear oligonucleotide hybridization chain reaction (LO-HCR) product, a primer exchange reaction (PER) product, an assembly of branched structures, a hybridization complex of a plurality of fluorescently labeled probes, or any combination thereof. In other embodiments, the probe product and/or one or more nucleic acid probes comprise one or more barcode regions.

In yet other embodiments, the nucleic acid of interest is a reporter oligonucleotide in a labelling agent comprising a binding moiety that directly or indirectly binds to a non-nucleic acid analyte, optionally wherein the reporter oligonucleotide comprises one or more barcode regions.

In other embodiments, the molecule of interest is a protein of interest.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, a binder or an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S.

Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

(iii) Products of Endogenous Analyte and/or Labelling Agent

In some embodiments, a molecule herein for detection is a product of an endogenous analyte and/or a labelling agent in a biological sample. In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product) or derivative thereof is analyzed. In some embodiments, a labelling agent (or a reporter oligonucleotide attached thereto) that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product) or derivative of a labelling agent that directly or indirectly binds to an analyte in the biological sample is analyzed.

C. Target Sequences and Barcodes

In some aspects, one or more of the target sequences includes one or more barcode(s), e.g., at least two, three, four, five, six, seven, eight, nine, ten, or more barcodes. A barcode can be attached to an analyte or to another moiety or structure in a reversible or irreversible manner. Barcodes can allow for identification and/or quantification of individual analytes (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In some embodiments, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences corresponding to the target molecules are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and U.S. Pat. Pub. 20210164039, all of which are hereby incorporated by reference in their entirety.

III. Polynucleotides and Hybridization Complexes

The probes may comprise any of a variety of entities that can hybridize to a nucleic acid, typically by Watson-Crick base pairing, such as DNA, RNA, LNA, PNA, etc., depending on the application. The nucleic acid probe(s) typically contains a hybridization region that is able to bind to at least a portion of a target nucleic acid, in some embodiments specifically. The nucleic acid probe may be able to bind to a specific target nucleic acid (e.g., an mRNA, or other nucleic acids as discussed herein). In some embodiments, the nucleic acid probes may be detected using a detectable label, and/or by using secondary nucleic acid probes able to bind to the nucleic acid probes. In some embodiments, the nucleic acid probes are compatible with one or more biological and/or chemical reactions. For instance, a nucleic acid probe disclosed herein can serve as a template or primer for a polymerase, a template or substrate for a ligase, a substrate for a click chemistry reaction, and/or a substrate for a nuclease (e.g., endonuclease for cleavage).

In some aspects, a target nucleic acid disclosed herein comprises any polynucleotide nucleic acid molecule (e.g., DNA molecule; RNA molecule, modified nucleic acid, etc.) for assessment in accordance with the provided embodiments, such as a polynucleotide present in a cell. In some embodiments, the target nucleic acid is a coding RNA (e.g., mRNA). The target may, in some embodiments, be a single RNA molecule. In other embodiments, the target may be at least one RNA molecule, e.g., a group of 2, 3, 4, 5, 6 or more RNA molecules. These RNA molecules may differ in molecule type, and/or may differ in sequence. In some embodiments, the target nucleic acid is, for example, a non-coding RNA (e.g., tRNA, rRNA, microRNA (miRNA), mature miRNA or immature miRNA). In some embodiments, the target nucleic acid is a splice variant of an RNA molecule (e.g., mRNA, pre-mRNA, etc.) in the context of a cell. A suitable target nucleic acid can therefore be an unspliced RNA (e.g., pre-mRNA, mRNA), a partially spliced RNA, or a fully spliced RNA, etc. Target nucleic acids of interest may be variably expressed, e.g., have a differing abundance, within a cell population, wherein the methods of the present disclosure allow profiling and comparison of the expression levels of nucleic acids, comprising but not limited to, RNA transcripts, in individual cells. A target nucleic acid can also be a DNA molecule, e.g., a denatured genomic, viral, plasmid, etc. For example, the methods can be used to detect copy number variants, e.g., in a cancer cell population in which a target nucleic acid is present at different abundance in the genome of cells in the population; a virus-infected cells to determine the virus load and kinetics, and the like.

In some aspects, the methods provided herein are used to analyze a target nucleic acid, e.g., a messenger RNA molecule. In some embodiments, the target nucleic acid is an endogenous nucleic acid present in a biological sample. In some embodiments, the target nucleic acid is present in a cell in a tissue, for instance in a tissue sample or tissue section. In some embodiments, the tissue sample is an intact tissue sample or a non-homogenized tissue sample. In some embodiments, the tissue sample is a fresh tissue sample. In some embodiments, the tissue has previously been processed, e.g., fixed, embedded, frozen, or permeabilized using any of the steps and/or protocols described in Section II. In some embodiments, the target nucleic acid is an exogenous nucleic acid contacted with a biological sample.

In some aspects, the provided embodiments can be employed for in situ detection of a target nucleic acid in a cell, e.g., in cells of a biological sample or a sample derived from a biological sample, such as a tissue section on a solid support, such as on a transparent slide.

In some aspects, provided herein are in situ assays using microscopy as a readout, e.g., detection or determination methods involving an optical readout. In some aspects, detection or determination of a sequence of one, two, three, four, five, or more nucleotides of a target nucleic acid is performed in situ in a cell in an intact tissue. In some aspects, the detection or determination is of a sequence associated with or indicative of a target nucleic acid. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, the present disclosure provides methods for high-throughput profiling one or more single nucleotides of interest in a large number of targets in situ, such as transcripts and/or DNA loci, for detecting and/or quantifying nucleic acids in cells, tissues, organs or organisms.

In some aspects, the methods disclosed herein involve the use of one or more probes or probe sets that hybridize to a target nucleic acid, such as an RNA molecule, wherein at least one probe is a circularizable probe or probe set (e.g., padlock probe) comprising asymmetric arms that hybridize to a nucleic acid molecule. Exemplary probes may be based on a circularizable probe or probe set (e.g., padlock probe), a gapped circularizable probe or probe set (e.g., gapped padlock probe), a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary. In some embodiments, a primary probe (e.g., a DNA probe that directly binds to an RNA target) is amplified through rolling circle amplification. In some embodiments, the primary probes, such as a circularizable probe or probe set (e.g., padlock probe) that comprises a padlock probe, contain one or more barcodes. In some embodiments, one or more barcodes are indicative of a sequence in the target nucleic acid, such as a single nucleotide of interest (e.g., SNPs or point mutations), a dinucleotide sequence, or a short sequence of about 5 nucleotides in length.

In some embodiments, provided herein are methods for assessing one or more target nucleic acids, such as a plurality of different mRNAs, in a biological sample, such as a cell or a tissue sample (such as a tissue section). In some embodiments, the target nucleic acid comprises DNA. In some embodiments, the target nucleic acid comprises RNA. In some embodiments, the probe comprises DNA. In some embodiments, the target nucleic acid is RNA and the probe comprises DNA.

In some aspects, the provided methods are employed for in situ analysis of target nucleic acids, for example for in situ detection or multiplexed analysis in intact tissues or a sample with preserved cellular or tissue structure. In some aspects, the provided methods can be used to detect or determine the identity or amount in situ of single nucleotides of interest in target nucleic acids, for instance of single nucleotide polymorphisms of genes of interest.

In some aspects, the provided methods involve a step of contacting, or hybridizing, one or more polynucleotides, such as any of the probes described herein, to a cell or a sample containing a target nucleic acid with a region (e.g., single nucleotide) of interest in order to form a hybridization complex. In some aspects, the provided methods comprise one or more steps of ligating the polynucleotides, for instance of ligating the ends of a circularizable probe or probe set (e.g., padlock probe) to form a circularized probe. In some aspects, the provided methods involve a step of amplifying one of the polynucleotides (e.g., a padlock probe or a circularized probe produced therefrom), to generate an amplification product. In some aspects, the provided methods involve a step of detecting and/or determining the sequence of all or a portion of the amplification product (for example, of one or more barcodes contained in the amplification product) and/or one or more of the polynucleotides with or without amplification, for instance any barcodes contained therein. In some aspects, the provided methods involve performing one or more of the steps described herein, simultaneously and/or sequentially.

The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some embodiments, the number of distinct barcode sequences in a population of nucleic acid probes is less than the number of distinct targets (e.g., nucleic acid analytes and/or protein analytes) of the nucleic acid probes, and yet the distinct targets may still be uniquely identified from one another, e.g., by encoding a probe with a different combination of barcode sequences. However, not all possible combinations of a given set of barcode sequences need be used. For instance, each probe may contain 1, 2, 3, 4, 5, 6, 7, 8, 9, 10, 11, 12, 13, 14, 15, etc. or more barcode sequences. In some embodiments, a population of nucleic acid probes may each contain the same number of barcode sequences, although in other cases, there may be different numbers of barcode sequences present on the various probes. In some embodiments, the barcode sequences or any subset thereof in the population of nucleic acid probes can be independently and/or combinatorially detected and/or decoded.

IV. Ligation, Extension, and Amplification

In some aspects, after formation of a hybridization complex comprising nucleic acid probes and/or probe sets described in Section III and the target nucleic acids, the assay further comprises one or more steps such as ligation, extension and/or amplification of the probe or probe set hybridized to the target nucleic acid. In some embodiments, the methods of the present disclosure include the step of performing rolling circle amplification in the presence of a target nucleic acid of interest.

In some embodiments, the method comprises using a circular or circularizable construct hybridized to the target nucleic acid comprising the region of interest to generate a product (e.g., comprising a sequence of the region of interest or one or more barcode sequences associated with the target nucleic acid). In some aspects, the product is generated using RCA. In any of the embodiments herein, the method can comprise ligating the ends of a circularizable probe or probe set (e.g., padlock probe) hybridized to the target RNA to form a circularized probe (e.g., circularized padlock probe). In any of the embodiments herein, the method can further comprise generating a rolling circle amplification product of the circularized padlock probe. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In any of the embodiments herein, the method can further comprise detecting a signal associated with the rolling circle amplification product in the biological sample.

In some aspects, the ligation product or a derivative thereof (e.g., extension product) can be detected. In some cases, RCA is not performed.

In some embodiments, the circular construct is directly hybridized to the target nucleic acid. In some embodiments, the circular construct is formed from a circularizable probe or probe set (e.g., padlock probe). In some embodiments, the circular construct is formed from a probe or probe set capable of DNA-templated ligation. See, e.g., U.S. Pat. No. 8,551,710, the content of which is hereby incorporated by reference in its entirety. In some embodiments, the circular construct is formed from a probe or probe set capable of RNA-templated ligation. Exemplary RNA-templated ligation probes and methods are described in US 2020/022424 which is incorporated herein by reference in its entirety. In some embodiments, the circular construct is formed from a specific amplification of nucleic acids via intramolecular ligation (e.g., SNAIL) probe set. See, e.g., U.S. Pat. Pub. 20190055594, the content of which is hereby incorporated by reference in its entirety. In some embodiments, the circular construct is formed from a probe capable of proximity ligation, for instance a proximity ligation assay for RNA (e.g., PLAYR) probe set. See, e.g., U.S. Pat. Pub. 20160108458, the content of which is hereby incorporated by reference in its entirety.

In some embodiments, the circular construct is indirectly hybridized to the target nucleic acid. In some embodiments, the circular construct is formed from a probe set capable of proximity ligation, for instance a proximity ligation in situ hybridization (PLISH) probe set.

In some embodiments, the circularizing step may comprise ligation selected from the group consisting of enzymatic ligation, chemical ligation, template dependent ligation, and/or template independent ligation. In any of the embodiments herein, the ligation can comprise using a ligase having an RNA-templated DNA ligase activity and/or an RNA-templated RNA ligase activity. In any of the embodiments herein, the ligation can comprise using a ligase selected from the group consisting of a Chlorella virus DNA ligase (PBCV DNA ligase), a T4 RNA ligase, a T4 DNA ligase, and a single-stranded DNA (ssDNA) ligase. In any of the embodiments herein, the ligation can comprise using a PBCV-1 DNA ligase or variant or derivative thereof and/or a T4 RNA ligase 2 (T4 Rnl2) or variant or derivative thereof.

Upon addition of a DNA polymerase in the presence of appropriate dNTP precursors and other cofactors, the amplification primer is elongated by replication of multiple copies of the template (e.g., a concatemer of the template is generated). This amplification product can be detected using, e.g., the secondary and higher order probes and detection oligonucleotides described herein. In some embodiments, the sequence of the amplicon or a portion thereof, is determined or otherwise analyzed, for example by using detectably labeled probes and imaging. The analysis of the amplification products can comprise sequencing by hybridization, sequencing by ligation, and/or fluorescent in situ detection, and/or wherein the in situ hybridization comprises sequential fluorescent in situ hybridization. In some instances, in situ detection using, e.g., the secondary and higher order probes and detection oligonucleotides described herein.

In any of the embodiments herein, the method can further comprise generating the product of the circularized probe in situ in the biological sample. In any of the embodiments herein, the product can be generated using rolling circle amplification (RCA). In any of the embodiments herein, the RCA can comprise a linear RCA, a branched RCA, a dendritic RCA, or any combination thereof. In any of the embodiments herein, the product can be generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

In any of the embodiments herein, the product can be immobilized in the biological sample. In any of the embodiments herein, the product can be crosslinked to one or more other molecules in the biological sample.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a $N^6$-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, WO 2014/163886, WO2014/025392, US 2017/0219465, US 2021/0215581, WO 2017/079406, U.S. Ser. No. 10/138,509, US 2016/0024555, US 2018/0251833, US2019/0276881, US2020/0071751, WO2020/0076976, WO2020/0076979, and WO2020/0096687, all of which are incorporated herein by reference in their entireties. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

V. Detection and Analysis

In some embodiments, a method disclosed herein comprises detecting one or more target nucleic acids (e.g., genomic DNA, cellular RNA such as mRNA, cDNA, viral DNA or RNA, a nucleic acid probe, a reporter oligonucleotide attached to a functional moiety such as a binding moiety, or a product thereof) in a sample using a plurality of primary probes configured to hybridize to the one or more target nucleic acids, wherein each primary probe comprises (i) a target-hybridizing region configured to hybridize to a different target region in the corresponding target nucleic acid, and (ii) a barcode region. In some embodiments, the sample is contacted with a plurality of detectable probes, wherein each detectable probe is configured to hybridize to (i) a barcode sequence in the barcode regions of the plurality of primary probes, or (ii) a complement of the barcode sequence. In some embodiments, the method further comprises detecting a signal associated with the plurality of detectable probes or absence thereof at one or more locations in the sample. In some embodiments, the sample is contacted with a subsequent plurality of detectable probes, wherein each detectable probe in the subsequent plurality is configured to hybridize to (i) a subsequent barcode sequence in the barcode regions of the plurality of primary probes, or (ii) a complement of the subsequent barcode sequence. In some embodiments, the method further comprises detecting a subsequent signal associated with the subsequent plurality of detectable probes or absence thereof at the one or more locations in the sample. In some embodiments, the method further comprises generating a signal code sequence comprising signal codes corresponding to the signal or absence thereof and the subsequent signal or absence thereof, respectively, at the one or more locations, wherein the signal code sequence corresponds to one of the one or more target nucleic acids, thereby identifying the target nucleic acid at the one or more locations in the sample.

In some embodiments, in situ detection of one or more target nucleic acids in a sample is performed using sequential hybridization of detectable probes to the plurality of primary probes, and using signals associated with the sequentially hybridized detectable probes to decode signal code sequences each assigned to one of the one or more target nucleic acids in the sample. Each primary probe can be selected from the group consisting of: a probe comprising a 3' or 5' overhang (e.g., L-shaped probes), optionally wherein the 3' or 5' overhang comprises one or more barcode sequences; a probe comprising a 3' overhang and a 5' overhang (e.g., U-shaped probes), optionally wherein the 3' overhang and the 5' overhang each independently comprises one or more barcode sequences; a circular probe; a circularizable probe or probe set; a probe or probe set comprising a split hybridization region configured to hybridize to a splint, optionally wherein the split hybridization region comprises one or more barcode sequences; and a combination thereof.

In some embodiments, the method comprises generating a signal code sequence at one or more locations in a sample, the signal code sequence comprising signal codes corresponding to the signals (or absence thereof) associated with detectable probes for in situ hybridization that are sequentially applied to the sample, wherein the signal code sequence corresponds to an analyte in the sample, thereby detecting the analyte at the one or more of the multiple locations in the sample.

In some embodiments, the present disclosure relates to the detection of nucleic acids sequences in situ using probe hybridization cycles and generation of amplified signals associated with the probes, wherein background signal is reduced and sensitivity is increased.

Exemplary in situ detection methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

In some embodiments, a method disclosed herein comprises generating rolling circle amplification (RCA) products associated with one or more target nucleic acids in a sample. In some embodiments, the RCA products are detected in situ in a sample, thereby detecting the one or more target nucleic acids. In some embodiments, each of the RCA products comprises multiple complementary copies of a barcode sequence, wherein the barcode sequence is associated with a target nucleic acid in the sample and is assigned a signal code sequence. In some embodiments, the method comprises contacting the sample with a first detectable probe comprising (i) a recognition sequence complementary to a sequence in the complementary copies of the barcode sequence and (ii) a reporter. In some embodiments, the method comprises detecting a first signal or absence thereof from the reporter of the first detectable probe hybridized to its corresponding sequence of the complementary copies of the barcode sequence in the RCA product, wherein the first signal or absence thereof corresponds to a first signal code in the signal code sequence. In some embodiments, the method comprises contacting the sample with a subsequent detectable probe comprising (i) a recognition sequence complementary to a sequence of the complementary copies of the barcode sequence and (ii) a reporter. In some embodiments, the method comprises detecting a subsequent signal or absence thereof from the reporter of the subsequent detectable probe hybridized to its corresponding sequence of the complementary copies of the barcode sequence in the RCA product, wherein the subsequent signal or absence thereof corresponds to a subsequent signal code in the signal code sequence. In some embodiments, the signal code sequence comprising the first signal code and the subsequent signal code is determined at a location in the sample, thereby decoding the barcode sequence and identifying the target nucleic acid at the location in the sample.

In some embodiments, the barcode sequence comprises one or more barcode positions each comprising one or more barcode subunits. In some embodiments, a barcode position in the barcode sequence partially overlaps an adjacent barcode position in the barcode sequence. In some embodiments, the first detectable probe and the subsequent detectable probe are in a set of detectable probes each comprising the same recognition sequence and a reporter. In some embodiments, the reporter of each detectable probe in the set comprises a binding site for a reporter probe comprising a detectable moiety. In some embodiments, the reporter probe binding site of the first detectable probe and the reporter probe binding site of the subsequent detectable probe are the same. In some embodiments, the reporter probe binding site of the first detectable probe and the reporter probe binding site of the subsequent detectable probe are different. In some embodiments, the detectable moiety is a fluorophore and the signal code sequence is a fluorophore sequence uniquely assigned to the target nucleic acid. In some embodiments, the detectable probes in the set are contacted with the sample sequentially in a pre-determined sequence which corresponds to the signal code sequence assigned to the barcode sequence. In some embodiments, the detectable probes in the set are contacted with the sample to determine signal codes in the signal code sequence until sufficient signal codes have been determined to decode the barcode sequence, thereby identifying the target nucleic acid.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, WO 2019/236841, WO 2020/102094, WO 2020/163397, and WO 2021/067475, all of which are incorporated herein by reference in their entireties.

In some embodiments, hybridization chain reaction (HCR) can be used for signal detection in situ. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described (see, e.g., WO 2020/123742 incorporated herein by reference), and may be used in the methods herein.

In some embodiments, similar to HCR reactions that use hairpin monomers, linear oligo hybridization chain reaction (LO-HCR) can be used for signal detection in situ. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. In any of the embodiments herein, the target nucleic acid molecule and/or the analyte can be an RCA product.

In some embodiments, detection of nucleic acids sequences in situ comprises generating an assembly for branched signal amplification. In some embodiments, the assembly complex comprises an amplifier hybridized directly or indirectly (via one or more oligonucleotides) to a sequence of the RCA product. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some embodiments, detection of nucleic acids sequences in situ comprises a primer exchange reaction (PER). In various embodiments, a primer with a domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising RCA products generated using methods described herein. In various embodiments, the RCA product may be contacted with a plurality of concatemer primers and a plurality of labeled probes. see e.g., U.S. Pat. Pub. No. US20190106733, the content of which is incorporated herein by reference, for exemplary molecules and PER reaction components.

In some embodiments, a sample is contacted with a detectable probe or probe set for in situ detection. In some embodiments, the detectable probe or probe set is circular or circularizable to generate a circularized template. In some embodiments, the circular probe or circularized template is used to generate an RCA product. In some embodiments, a detectable probe or probe set can comprise a region which is an initiator for hybridization chain reaction (HCR) or which hybridizes to an initiator for HCR. In some embodiments, a detectable probe or probe set can comprise a region which is an initiator for linear oligonucleotide hybridization chain reaction (LO-HCR) or which hybridizes to an initiator for LO-HCR. In some embodiments, a detectable probe or probe set can comprise a region which is a primer for primer exchange reaction (PER) or which hybridizes to a primer for PER. In some embodiments, a detectable probe or probe set can comprise a region which is a pre-amplifier for branched DNA (bDNA) or which hybridizes to a pre-amplifier for bDNA.

In some cases, detectable probes disclosed herein can comprise one or more features of and/or be modified based on: a split FISH probe or probe set described in WO 2021/167526A1 or Goh et al., "Highly specific multiplexed RNA imaging in tissues with split-FISH," Nat Methods 17(7):689-693 (2020), all of which are incorporated herein by reference in their entireties; a Z-probe or probe set, such as one described in U.S. Pat. No. 7,709,198 B2, U.S. Pat. No. 8,604,182 B2, U.S. Pat. No. 8,951,726 B2, U.S. Pat. No. 8,658,361 B2, or Tripathi et al., "Z Probe, An Efficient Tool for Characterizing Long Non-Coding RNA in FFPE Tissues," Noncoding RNA 4(3):20 (2018), all of which are incorporated herein by reference in their entireties; an HCR initiator or amplifier, such as one described in U.S. Pat. No. 7,632,641 B2, US 2017/0009278 A1, U.S. Pat. No. 10,450,599 B2, Dirks and Pierce, "Triggered amplification by hybridization chain reaction," PNAS 101(43):15275-15278 (2004), Chemeris et al., "Real-time hybridization chain reaction," Dokl. Biochem 419:53-55 (2008), Niu et al., "Fluorescence detection for DNA using hybridization chain reaction with enzyme-amplification," Chem Commun (Camb) 46(18):3089-91 (2010), Choi et al., "Programmable in situ amplification for multiplexed imaging of mRNA expression," Nat Biotechnol 28(11):1208-12 (2010), Song et al., "Hybridization chain reaction-based aptameric system for the highly selective and sensitive detection of protein," Analyst 137(6):1396-401 (2012), Choi et al., "Third-generation in situ hybridization chain reaction: multiplexed, quantitative, sensitive, versatile, robust," Development 145 (12): dev165753 (2018), or Tsuneoka and Funato, "Modified in situ Hybridization Chain Reaction Using Short Hairpin DNAs," Front Mol Neurosci 13:75 (2020), all of which are incorporated herein by reference in their entireties; a PLAYR probe or probe set, such as one described in US 2016/0108458 A1 or Frei et al., "Highly multiplexed simultaneous detection of RNAs and proteins in single cells," Nat Methods 13(3):269-75 (2016), all of which are incorporated herein by reference in their entireties; a PLISH probe or probe set, such as one described in US 2020/0224243 A1 or Nagendran et al., "Automated cell-type classification in intact tissues by single-cell molecular profiling," eLife 7:e30510 (2018), all of which are incorporated herein by reference in their entireties; a RollFISH probe or probe set such as one described in Wu et al., "RollFISH achieves robust quantification of single-molecule RNA biomarkers in paraffin-embedded tumor tissue samples," Commun Biol 1, 209 (2018), the content of which is hereby incorporated by reference in its entirety; a MERFISH probe or probe set, such as one described in WO 2020/123742 A1 (PCT/US2019/065857) or Chen et al., "Spatially resolved, highly multiplexed RNA profiling in single cells," Science 348 (6233):aaa6090 (2015), all of which are incorporated herein by reference in their entireties; or a primer exchange reaction (PER) probe or probe set, such as one described in US 2019/0106733 A1, the content of which is hereby incorporated by reference in its entirety.

In some embodiments, a method disclosed herein comprises detecting all or a portion of an amplification product, such as one or more barcode sequences present in the amplification product. In some embodiments, the detection or determination comprises hybridizing to the amplification product a detectable probe, such as a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample. In some embodiments, a method disclosed herein comprises detecting a polymer generated by a hybridization chain reaction (HCR) reaction, see e.g., US 2017/0009278, which is incorporated herein by reference, for exemplary probes and HCR reaction components.

In some embodiments, the in situ detection herein can comprise sequencing performed in situ by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, WO 05/065814, US 2005/0100900, WO 06/064199, WO07/010,251, US 2012/0270305, US 2013/0260372, and US 2013/0079232, all of which are herein incorporated by reference in their entireties.

In some embodiments, the in situ detection herein can comprise sequential hybridization, e.g., sequencing by hybridization and/or sequential in situ fluorescence hybridization. Sequential fluorescence hybridization can involve sequential hybridization of detectable probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, WO 2021/138676, and US 2023/0039899, all of which are incorporated herein by reference.

In some embodiments, the in situ detection herein can comprise sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, all of which are herein incorporated by reference in their entireties.

In some embodiments, the barcodes of the detectable probes are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labeled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); U.S. Pat. No. 10,457,980 B2; US 2016/0369329 A1; WO 2018/026873 A1; US 2017/0220733 A1; US 2021/0017587, all of which are incorporated by reference in their entirety. In some embodiments, these assays enable signal amplification, combinatorial decoding, and error correction schemes at the same time.

In some embodiments, nucleic acid hybridization can be used for in situ detection. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), all of which are herein incorporated by reference in their entireties.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181, all of which are herein incorporated by reference in their entireties.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detectable probe or probe set. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detectable probe or probe set. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some aspects, the provided methods comprise imaging the amplification product (e.g., amplicon) and/or one or more portions of the polynucleotides, for example, via binding of one or more detectable probes and detecting the detectable label(s) directly or indirectly attached thereto. In some embodiments, the detectable probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. In any of the embodiments herein, "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In any of the embodiments herein, an antibody comprises an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

VI. Compositions and Kits

Also provided herein are kits, for example, comprising one or more quenchers, e.g., as described in Section I(B), comprising one or more detectable probes, e.g., as described in Section I(D) or Section V, comprising one or more polynucleotides, e.g., any described in Section III, and reagents for performing the methods provided herein, for example reagents required for one or more steps comprising hybridization, ligation, amplification, detection, sequencing, and/or sample preparation as described herein. In some embodiments, the kit further comprises a target nucleic acid, e.g., any described in Section II. In some embodiments, any or all of the polynucleotides are DNA molecules. In some embodiments, the target nucleic acid is a messenger RNA molecule. In some embodiments, the kit further comprises one or more ligases, for instance for forming a circular probe. In some embodiments, the kit further comprises a polymerase, for instance for performing amplification of a probe, e.g., using any of the methods described in Section IV. In some embodiments, the kit further comprises a primer for amplification. In some embodiments, the kit further comprises one or more detection reagents such as those disclosed in Section V.

In some embodiments, disclosed herein is a kit for reducing autofluorescence in a biological sample, comprising a quencher, wherein the quencher comprises a targeting moiety capable of reacting or binding with an endogenous biological moiety in the biological sample. In other embodiments, disclosed herein is a kit for reducing autofluorescence in a tissue sample, comprising a quencher, wherein the quencher comprises a targeting moiety capable of reacting or binding with an endogenous biological moiety in the tissue sample.

In yet other embodiments, disclosed herein is a kit for analyzing a biological sample, comprising a quencher, wherein the quencher comprises a targeting moiety capable of reacting or binding with an endogenous biological moiety in the biological sample. In still other embodiments, disclosed herein is a kit for analyzing a tissue sample, comprising a quencher, wherein the quencher comprises a targeting moiety capable of reacting or binding with an endogenous biological moiety in the tissue sample.

In some embodiments of any of the preceding embodiments, the kit may further comprise one or more detectable probes, optionally wherein the detectable probes are fluorescently labeled, optionally wherein the detectable probes are nucleic acid probes.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcoded detectable probes or detectable labels. In some embodiments, the kits optionally contain other components, for example nucleic acid primers, enzymes and reagents, buffers, nucleotides, modified nucleotides, reagents for additional assays.

VII. Applications

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. As detailed herein, the present disclosure provides methods for reducing autofluorescence of biological samples including tissue samples, thereby enabling the analysis of said biological samples by fluorescence detection. The methods of the present disclosure achieve this reduction in background autofluorescence by contacting the biological sample with quenchers having a targeting moiety capable of reacting or binding with one or more autofluorescent endogenous biological moieties present in the biological samples. The interaction between the targeting moiety and the autofluorescent sources may covalent in nature (e.g., the formation of a chemical bond) or can be driven by strong intermolecular forces (e.g., lipophilic attraction). By virtue of the targeted binding of the quenchers to the autofluorescent endogenous biological moieties, the background fluorescence is substantially reduced and remains reduced over multiple cycles of imaging. In some embodiments, the methods of the present disclosure may comprise contacting the tissue samples with one or more quenchers having a quencher dye and targeting moiety as described above in combination with one or more additional quenching agents. In some embodiments, the methods disclosed herein may further utilize one or more additional quenching agents to reduce tissue autofluorescence, for example, Autofluorescence Eliminator (Sigma/EMD Millipore), TrueBlack Lipofuscin Autofluorescence Quencher (Biotium), Max-Block Autofluorescence Reducing Reagent Kit (MaxVision Biosciences), and/or a very intense black dye (e.g., Sudan Black, or comparable dark chromophore).

In some aspects, the provided embodiments can be applied in an in situ method of analyzing nucleic acid sequences, such as an in situ transcriptomic analysis or in situ detection. In some aspects, the embodiments can be applied in an imaging or detection method for multiplexed, multi-cycle nucleic acid analysis. In some aspects, the provided embodiments can be used to identify or detect regions of interest in target nucleic acids.

In some aspects, the embodiments can be applied in investigative and/or diagnostic applications, for example, for characterization or assessment of particular cell or a tissue from a subject. Applications of the provided method can comprise biomedical research and clinical diagnostics. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

VII. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample or a bead). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have any suitable alternate backbone linkage. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any suitable variety of analogs of these sugar moieties. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Any suitable useful non-native bases that can be included in a nucleic acid or nucleotide may be used.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of their respective terminal complementary nucleic acid sequences (e.g., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using any suitable techniques such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(x) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also refer to an "epitope binding fragment" or "antibody fragment," which as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an $F(ab')_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. For example, detectably labelled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, $C_1$-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTrackerS Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorophyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, $R^{670}$ (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinium esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLES

The following examples are included for illustrative purposes only and are not intended to limit the scope of the present disclosure.

Example 1: Synthesis of Quenchers with Varied Targeting Chemistry and Solubility The quenchers as provided herein were synthesized according to the general synthetic protocols detailed in Chevalier et al. (2014) *Tetrahedron Letters* "Straightforward synthesis of bioconjugatable azo dyes. Part 2: Black Hole Quencher-2 (BHQ-2) and BlackBerry Quencher 650 (BBQ-650) scaffolds", 55 (50), 6764-6768; and in Chevalier et al. (2013) *Chem. Eur. J.* "Bioconjugatable Azo-Based Dark-Quencher Dyes: Synthesis and Application to Protease-Activatable Far-Red Fluorescent Probes", 19, 1686-1699, the contents of which are herein incorporated by reference in its entirety.

In brief, Compound 1A was synthesized as follows: Fast Black K diazonium salt ((E)-2,5-dimethoxy-4-((4-nitrophenyl)diazenyl)benzenediazonium chloride) (3.5 eq.) was reacted in an electrophilic aromatic substitution ($S_EAr$)-type reaction with aniline derivative 1-(3-(methyl(phenyl)amino) propyl)-1H-pyrrole-2,5-dione (1.0 eq.) at 0° C. in a (1:1, v/v) mixture of acetonitrile and sodium acetate buffer (0.1 M, pH 4.0) to give compound 1A.

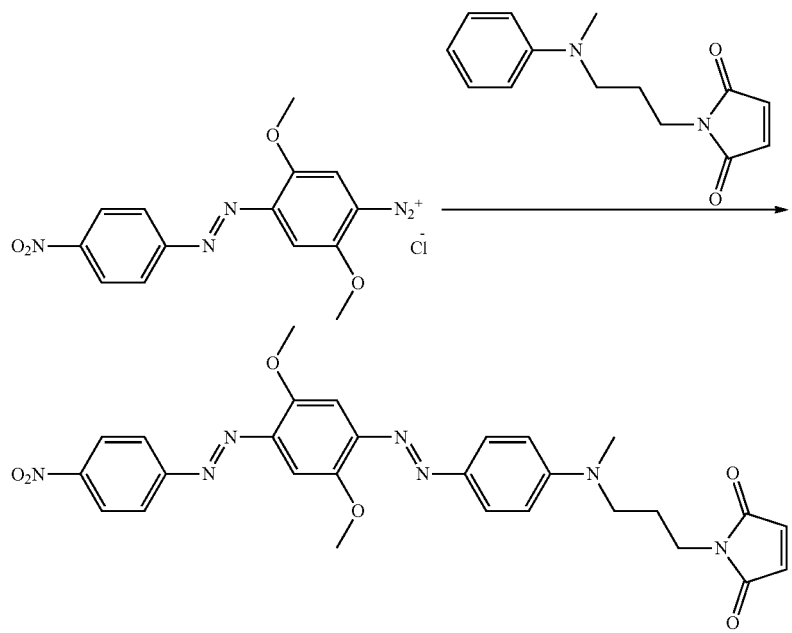

Compound 3A was synthesized as follows: Methylene Violet 3RAX was stirred in acetonitrile at 0° C. for 15 min in the presence of $NOBF_4$ at stoichiometric amounts, to give the diazotized tetrafluoroborate salt intermediate. This diazo salt was then reacted with aniline derivative 1-(3-(methyl (phenyl)amino)propyl)-1H-pyrrole-2,5-dione in acetonitrile at 0° C. for 1 hour to give compound 3A.

Table 1 shows eight exemplary quenchers prepared according to the synthetic method described in the references above. As detailed herein, the compounds in Table 1 below each contain a quencher dye (for instance, azobenzene) that masks tissue autofluorescence, a targeting moiety (for instance, maleimide) that covalently binds to the autofluorescence moiety. The exemplary quenchers were char-

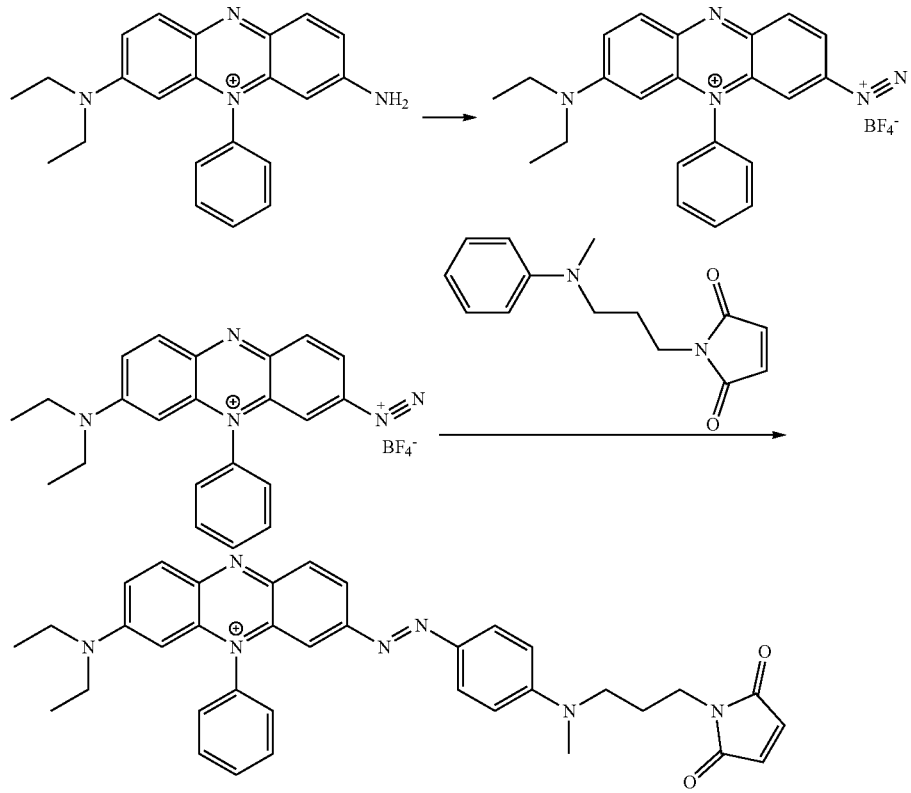

acterized by UV-visible absorption spectrometry. FIG. 1 show the UV-visible absorption spectra for four exemplary quenchers prepared (Compounds 1A, 2A, 3A and 4A, as compared to a commercially available quencher True Black.

TABLE 1

| Compound No. | Structure | UV-vis |
|---|---|---|
| 1A | 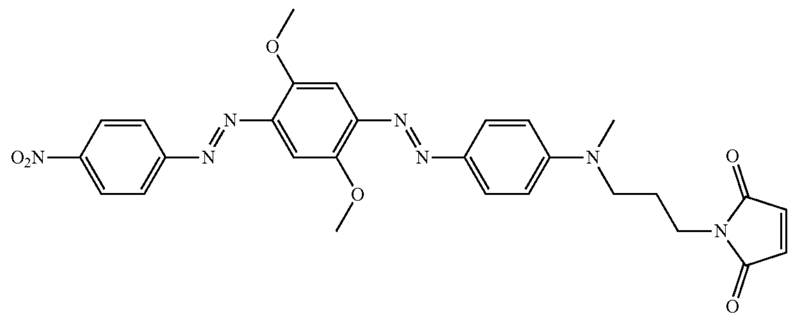 [SMILES: COc1cc(/N=N/c2ccc([N+](=O)[O-])cc2)c(OC)cc1/N=N/c1ccc(N(C)CCCN2C(=O)C=CC2=O)cc1] | FIG. 1 |
| 1B | 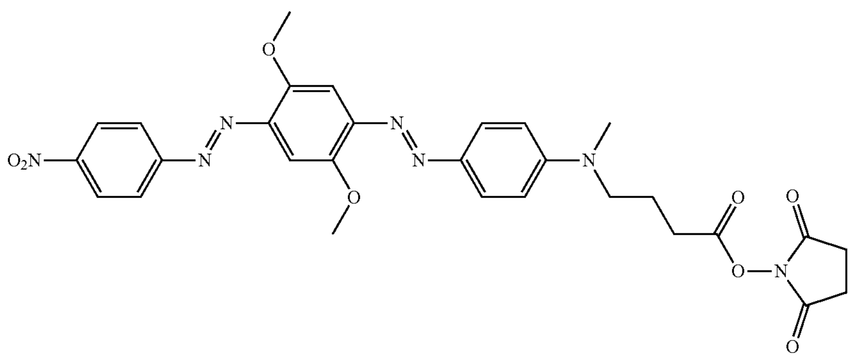 [SMILES: COc1cc(/N=N/c2ccc([N+](=O)[O-])cc2)c(OC)cc1/N=N/c1ccc(N(C)CCCC(=O)ON2C(=O)CCC2=O)cc1] | |
| 2A | 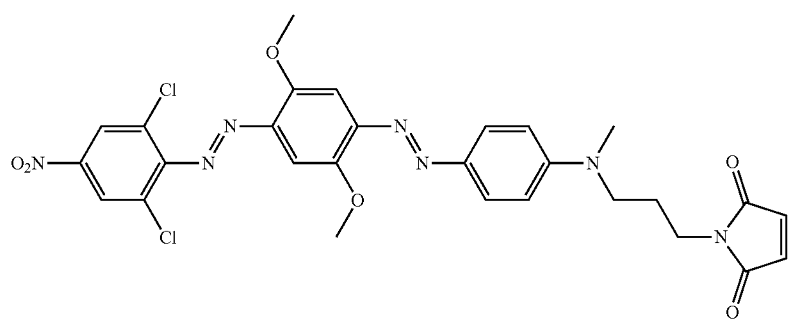 [SMILES: COc1cc(/N=N/c2c(Cl)cc([N+](=O)[O-])cc2Cl)c(OC)cc1/N=N/c1ccc(N(C)CCCN2C(=O)C=CC2=O)cc1] | FIG. 1 |
| 2B | 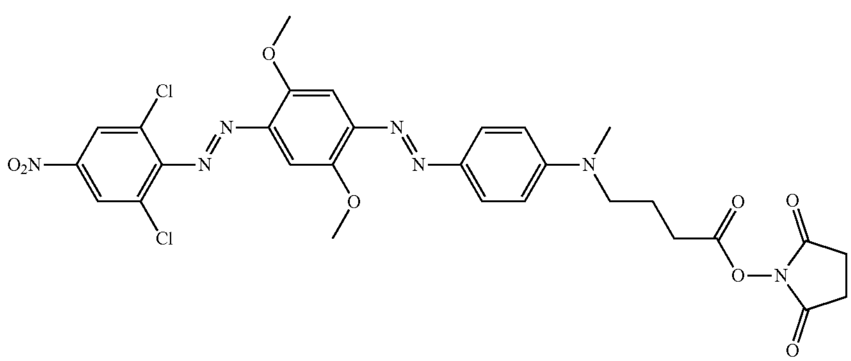 [SMILES: COc1cc(/N=N/c2c(Cl)cc([N+](=O)[O-])cc2Cl)c(OC)cc1/N=N/c1ccc(N(C)CCCC(=O)ON2C(=O)CCC2=O)cc1] | |

TABLE 1-continued

Exemplary Quenchers

| Compound No. | Structure | UV-vis |
|---|---|---|
| 3A | 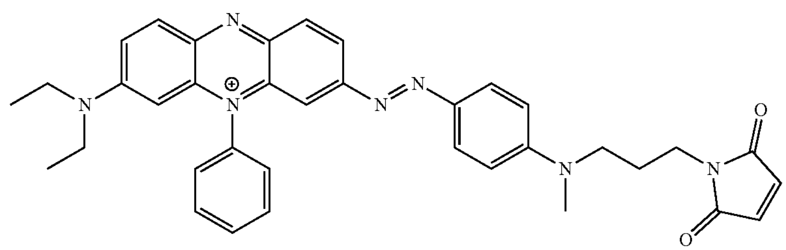 [SMILES: CCN(CC)c1ccc2nc3ccc(/N=N/c4ccc(N(C)CCCN5C(=O)C=CC5=O)cc4)cc3[n+](-c3ccccc3)c2c1] | FIG. 1 |
| 3B | 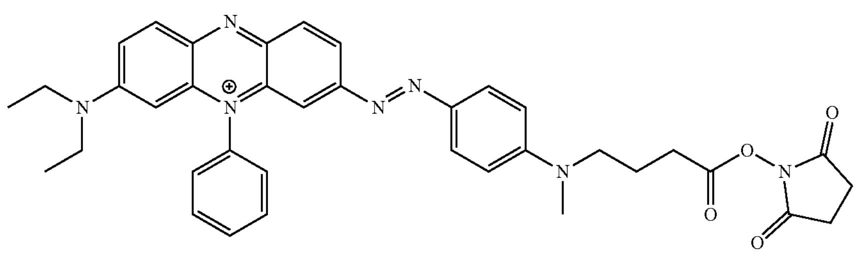 [SMILES: CCN(CC)c1ccc2nc3ccc(/N=N/c4ccc(N(C)CCCC(=O)ON5C(=O)CCC5=O)cc4)cc3[n+](-c3ccccc3)c2c1] | |
| 4A | 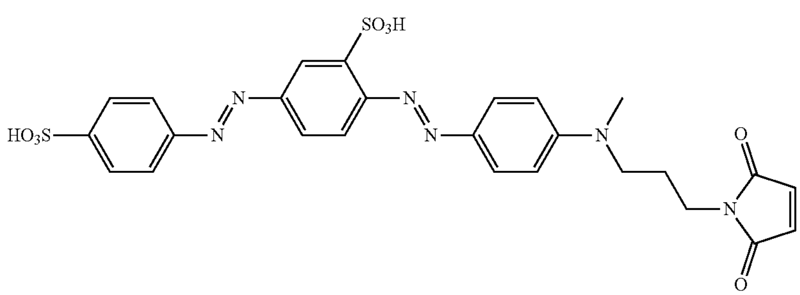 [SMILES: CN(CCCN1C(=O)C=CC1=O)c1ccc(/N=N/c2ccc(/N=N/c3ccc(S(=O)(=O)O)cc3)cc2S(=O)(=O)O)cc1] | FIG. 1 |
| 4B | 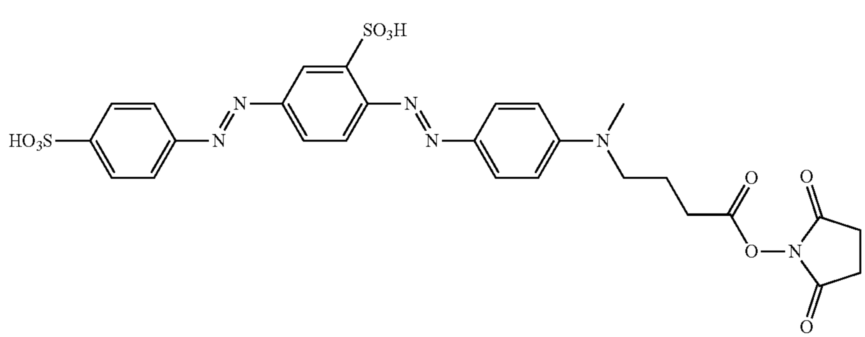 [SMILES: CN(CCCC(=O)ON1C(=O)CCC1=O)c1ccc(/N=N/c2ccc(/N=N/c3ccc(S(=O)(=O)O)cc3)cc2S(=O)(=O)O)cc1] | |

TABLE 1-continued

Exemplary Quenchers

| Compound No. | Structure | UV-vis |
|---|---|---|
| Comparative Quencher (commercial) | 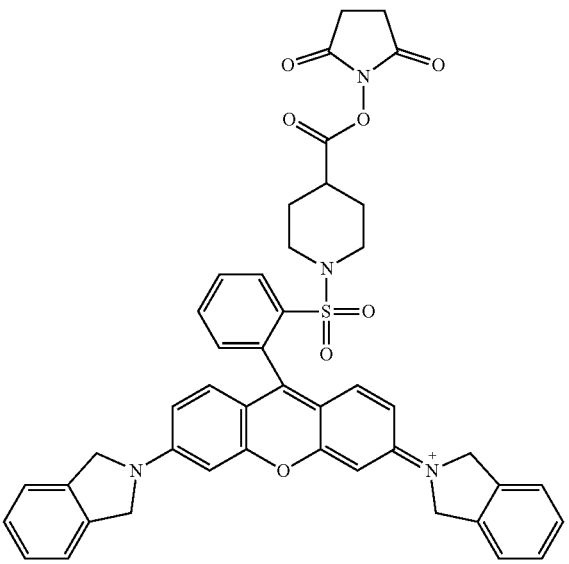 | |

Example 2: Method for Targeted Masking of Autofluorescence In Situ in Biological Samples The present example describes an exemplary method for masking autofluorescence of human and mouse tissues by using the quencher compound 1A during in situ analysis.

Staining and Quenching with Compound 1A

Formalin-fixed paraffin embedded (FFPE) human brain tissues and fresh frozen (FrF) mouse brain tissues were obtained for this example. The samples were sectioned to 10 µm thickness and transferred to Superfrost® Plus slides. The FFPE human brain tissues were treated multiple times with Histo-Clear® and citrate buffer to remove the embedded paraffin. The FrF mouse brain samples were fixed using 3.7% formaldehyde for 5 minutes. The slides were then incubated with nucleic acid probes targeting genes of interest. The nucleic acid probes were allowed to hybridize overnight in hybridization buffer at 37° C. The next day, the samples were washed using wash buffers to remove excess or unbound probes. The probes were then ligated in the presence of ligase, RNAase inhibitor and ligation buffer for 2 hours. Subsequently, the ligation products were amplified overnight using polymerases and amplification buffers. The samples were then stained using fluorescently labelled probes. Finally, the quenching agent compound 1A was dissolved in DMF (at 18 mM), diluted with 70% ethanol to provide solutions of compound 1A at concentrations of 3.6 mM, 1.8 mM, and 0.9 mM. These solutions were applied to the samples prior to imaging. Once imaged, the fluorescently labelled probes were stripped using a denaturing agent and contacted with additional detectable probes before the next imaging round. In this manner, multiple rounds of stripping, re-probing, and imaging of signals associated with the fluorescently labelled probes, were performed without any additional quenching steps.

Enrichment of Binding Moieties

Figure 2:
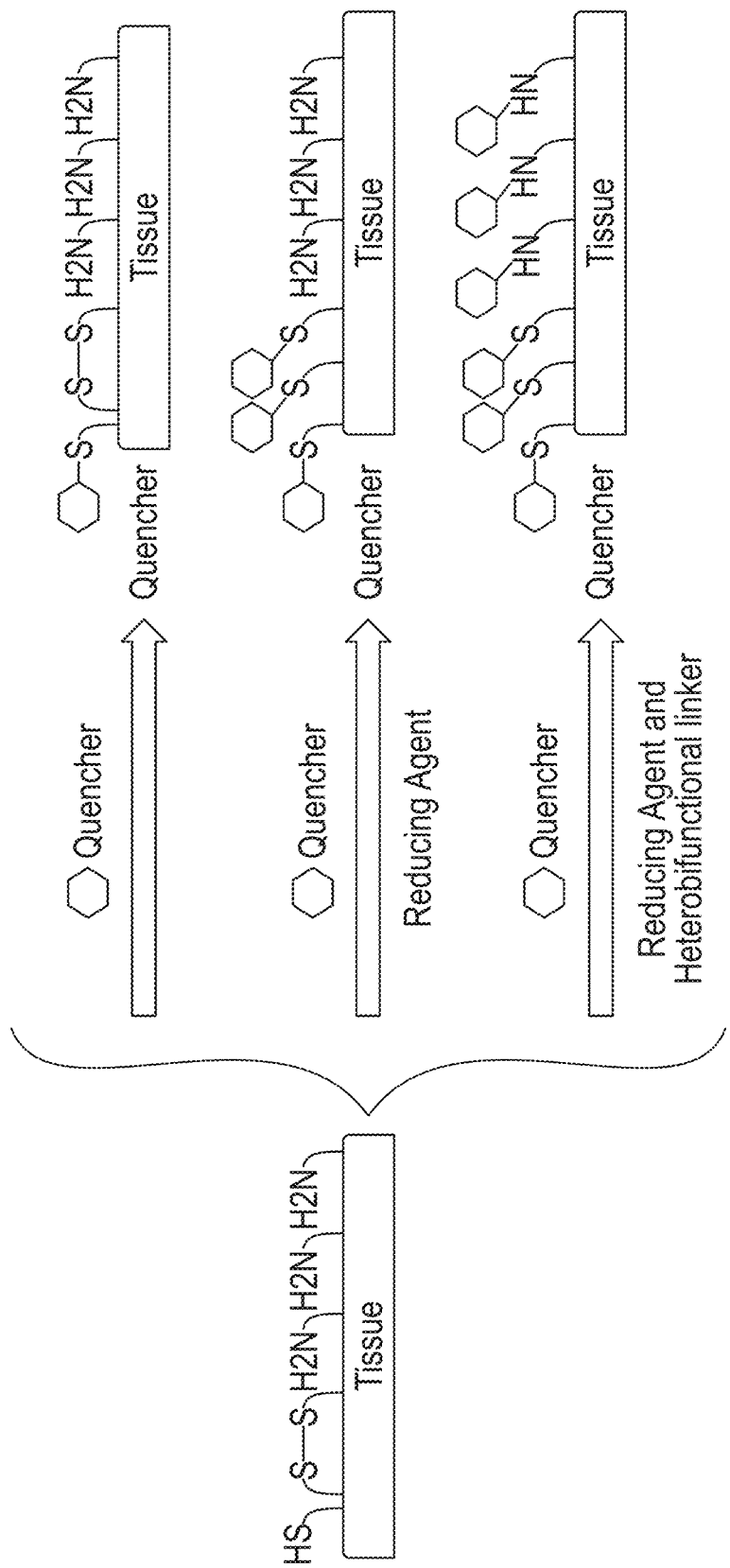
FIG. 2 shows examples of improving binding of a quencher to reactive sites in a biological sample (e.g., a tissue sample) by treating the biological sample with a reducing agent (e.g., DTT) and/or a multifunctional linker (e.g., PEG4-SPDP).

To improve the binding of compound 1A to tissue moieties responsible for autofluorescence, the FrF mouse brain tissues were treated with dithiothreitol (DTT, 50 mM) and 2% TEA for 10 minutes before quenching with compound 1A. DTT reduces disulfide bridges in the tissues thereby increasing the thiol content for improved binding of compound 1A. Alternatively, the tissues were treated with a combination of 2,5-dioxopyrrolidin-1-yl 3-oxo-1-(pyridin-2-yldisulfaneyl)-7,10,13,16-tetraoxa-4-azanonadecan-19-oate (PEG4-SPDP), a derivative of succinimidyl 3-(2-pyridyldithio) propionate (SPDP) comprising an internal tetraoligoethylene linker, and DTT, to convert amines to thiols and reduce any disulfide bridges to increase thiol content. For the reduction only treatment, the tissues were treated with DTT (50 mM for 10 minutes). For the conversion of amines to thiols and subsequent reduction, the tissues were treated first with PEG4-SPDP (10 mM) for 10 minutes, followed by treatment with DTT (50 mM) and compound 1A (0.9 mM). PEG4-SPDP is a multifunctional crosslinker for protein conjugation via amine-to-amine or amine-to-sulfhydryl crosslinks that contain a 4-unit polyethylene glycol (PEG) group and a reducible (cleavable) disulfide bond. The tissues were then washed prior to or after staining. FIG. 2 shows an exemplary scheme for enrichment of thiol moieties in a tissue sample by treating a tissue sample with a reducing agent (e.g., DTT) or with a reducing agent (e.g., DTT) and a multifunctional linker, e.g., PEG4-SPDP. Results were compared to the tissues incubated with a native thiol targeting group (control group). The compound 1A was found to efficiently stain the tissues with the targeting chemistry. Compound 1A efficiently reduced the background in dentate gyrus (DG) (FIGS. 3A-3B) and cortex samples of mouse brains (FIGS. 3C-3D) as well as in human brain tissues. FIGS. 3A and 3C depict the fluorescence for the dentate gyrus and cortex portions prior to quenching, in which punctuate fluorescence signals were associated with rolling circle amplification products, and amorphous background fluorescence was detected. As shown in FIGS. 3B and 3D, the background signal was significantly reduced after the tissue samples were subjected to stripping with DMSO, treatment with compound 1A and rehybridization with additional probes.

Figure 5:
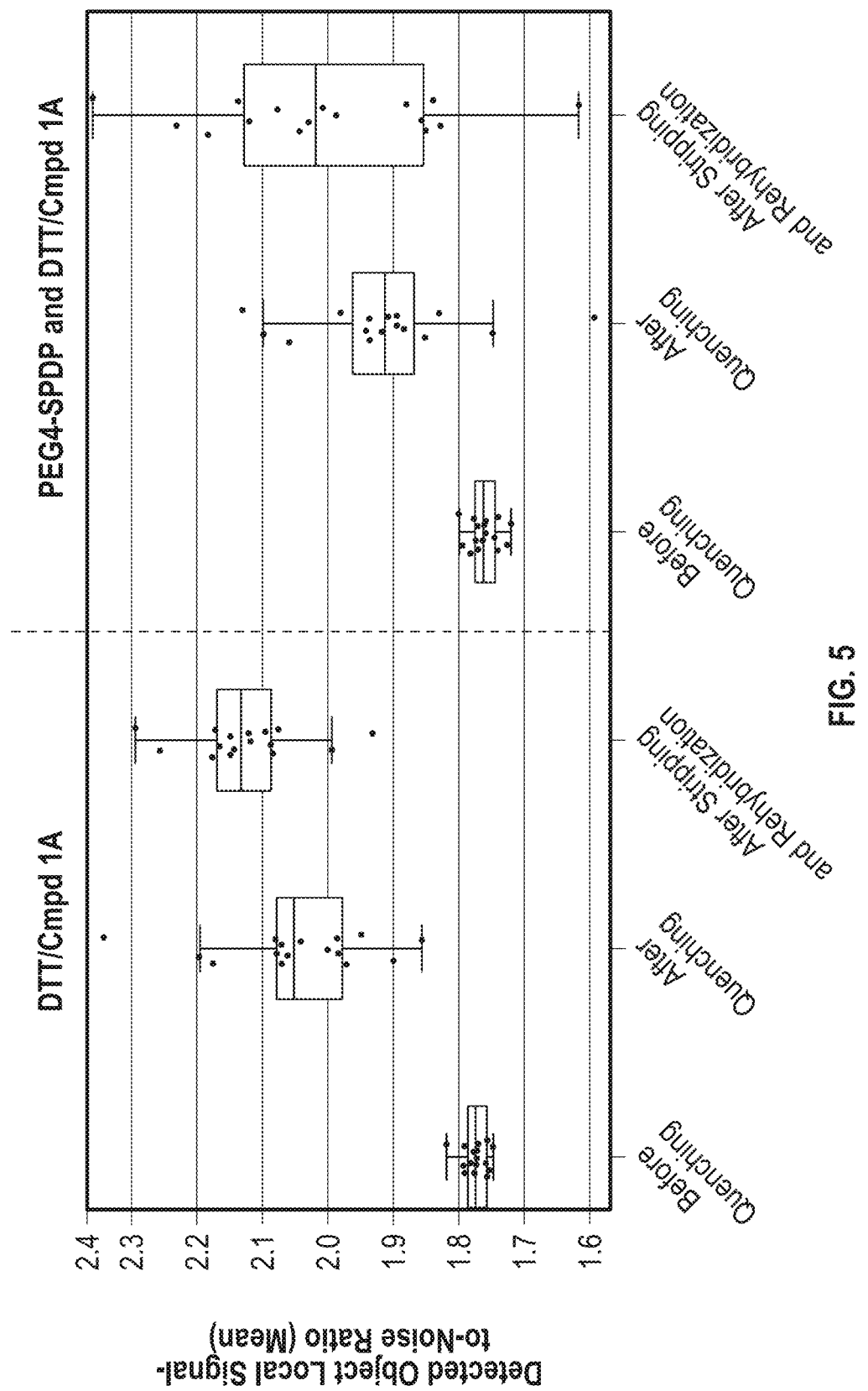
FIG. 5 depicts the quantitation of detected object local signal-to-noise ratio (mean) measured from images of the FFPE human brain tissue before quenching, after quenching, and after stripping and rehybridization of additional detectable probes, using dithiothreitol (DTT)/Compound 1A or the combination of PEG4-SPDP and DTT/Compound 1A.
Figure 6A:
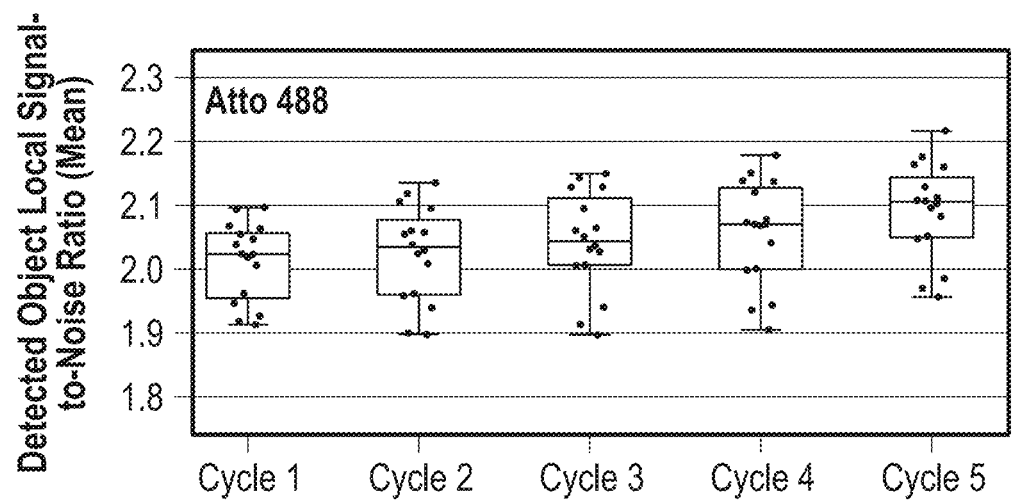
FIGS. 6A-6D display the quantitation of detected object local signal-to-noise ratio (mean) in images after 5 cycles of stripping and rehybridization with the fluorescent detectable probes.
Figure 6B:
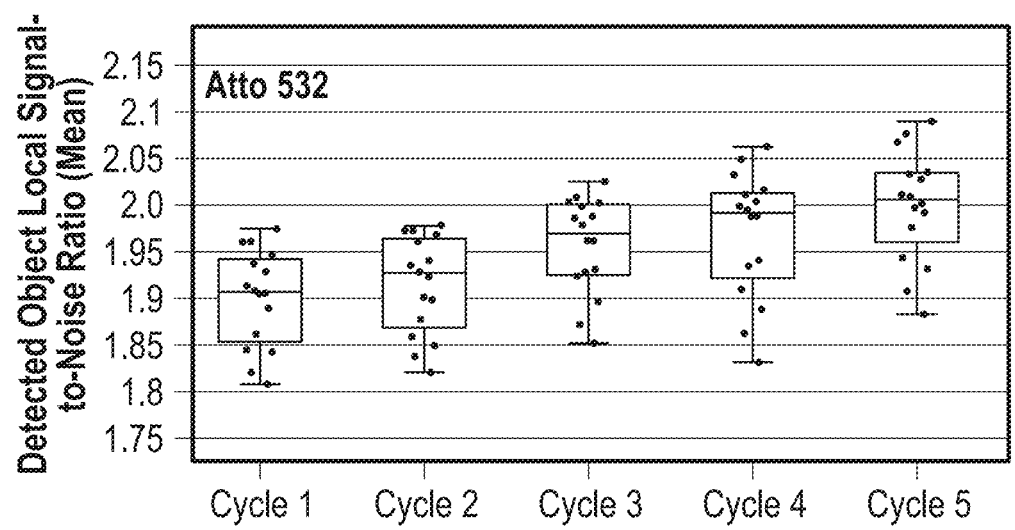
Figure 6C:
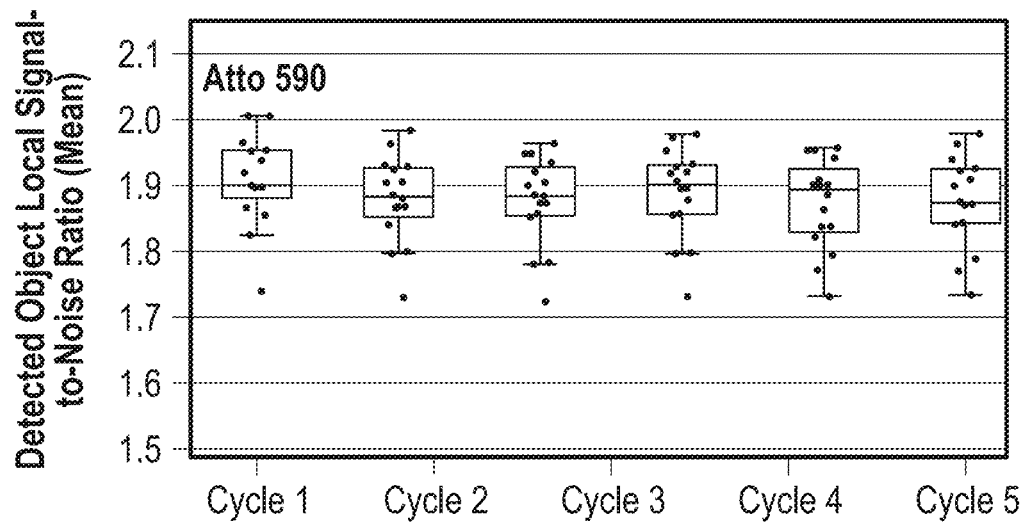
Figure 6D:
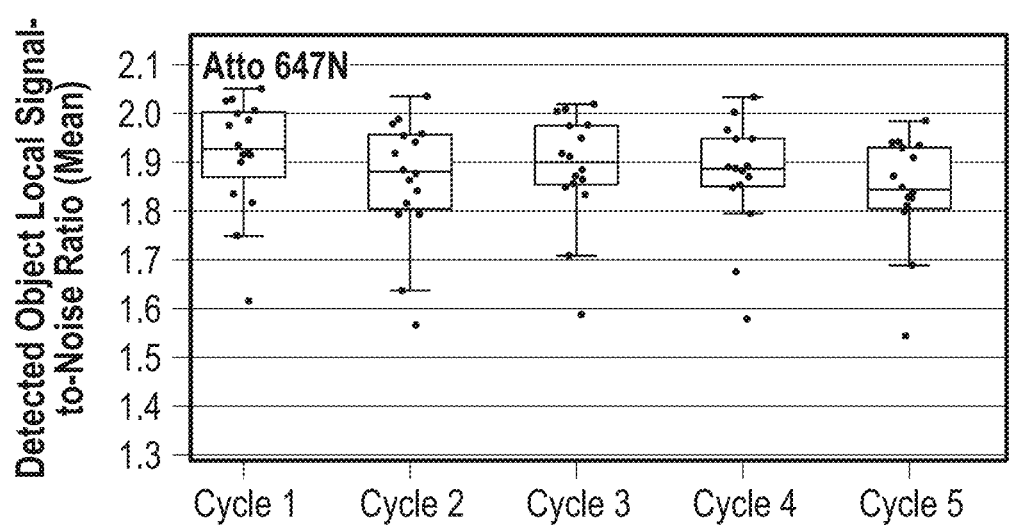
Figure 7A:
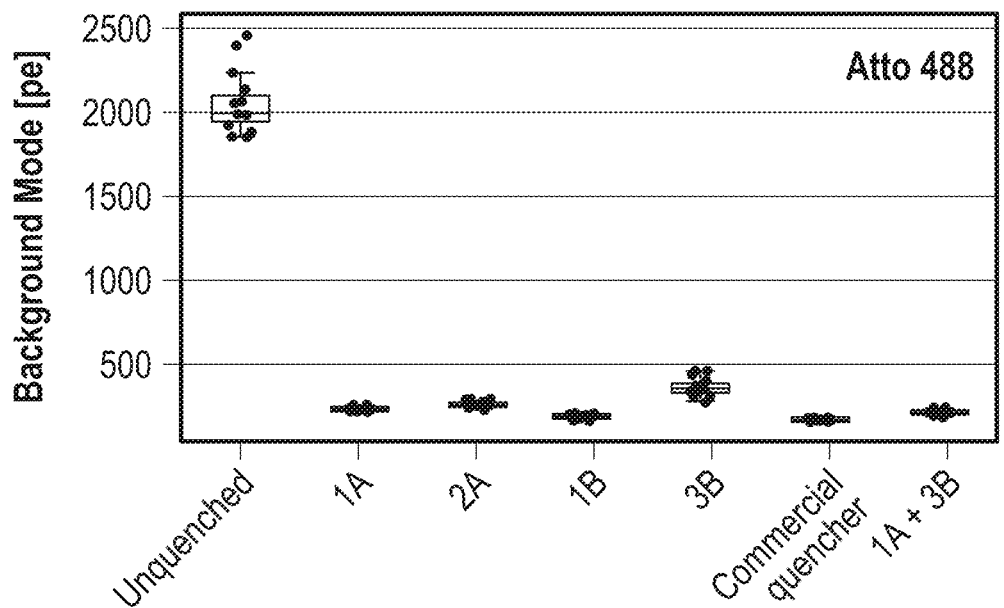
FIGS. 7A-7D depict the background signals recorded for the tissues quenched with compounds 1A, 2A, 1B, 3B, or a combination of 1A and 3B at four separate wavelengths (using ATTO 488, ATTO 532, ATTO 590, and ATTO 647 fluorescent dye labeled detectable probes, respectively) as compared to the unquenched and a commercial quencher.
Figure 7B:
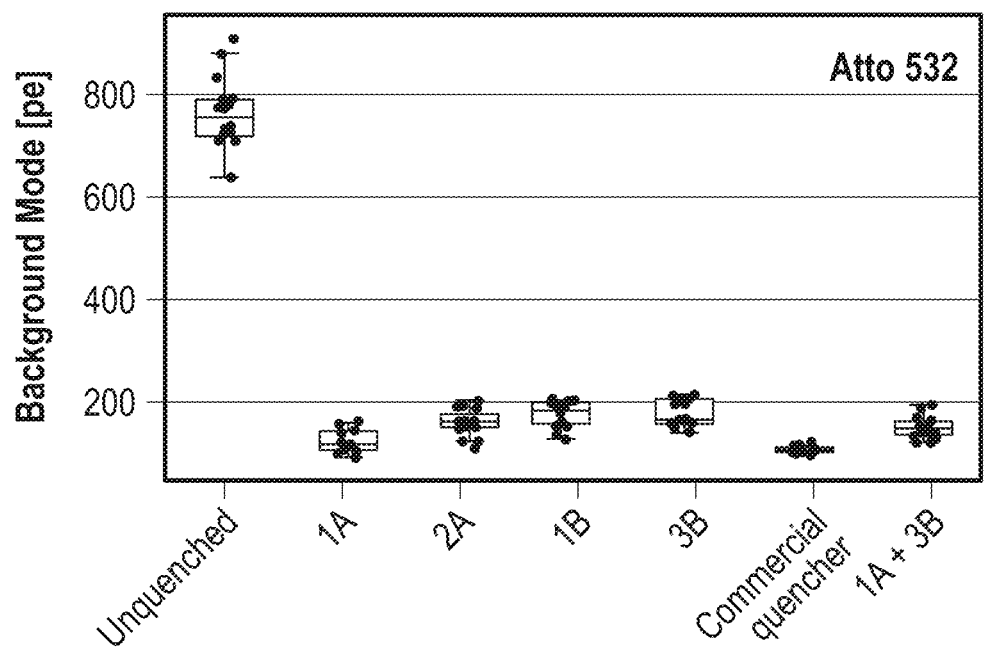
Figure 7C:
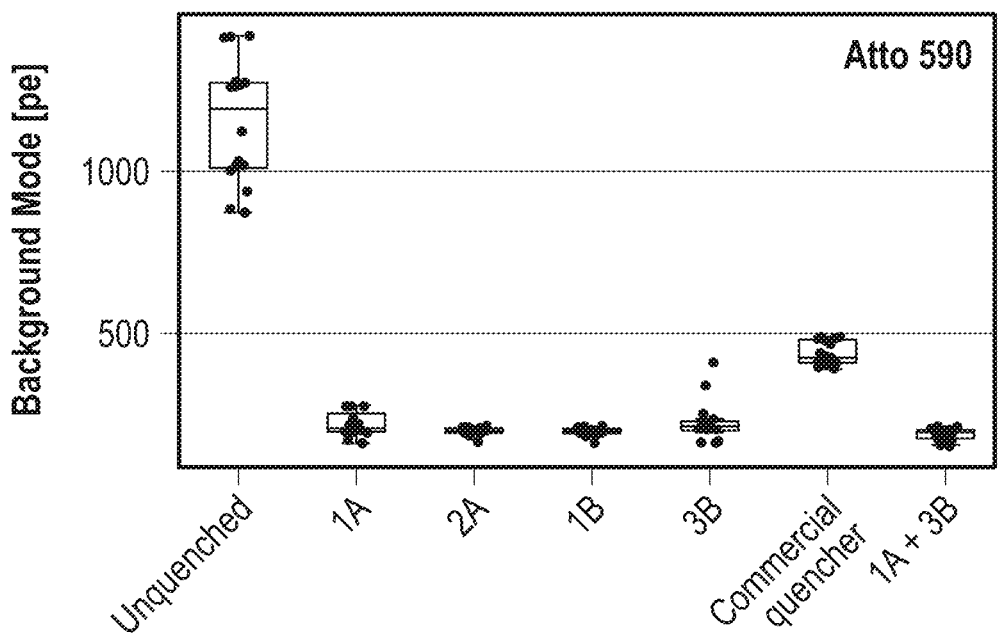
Figure 7D:
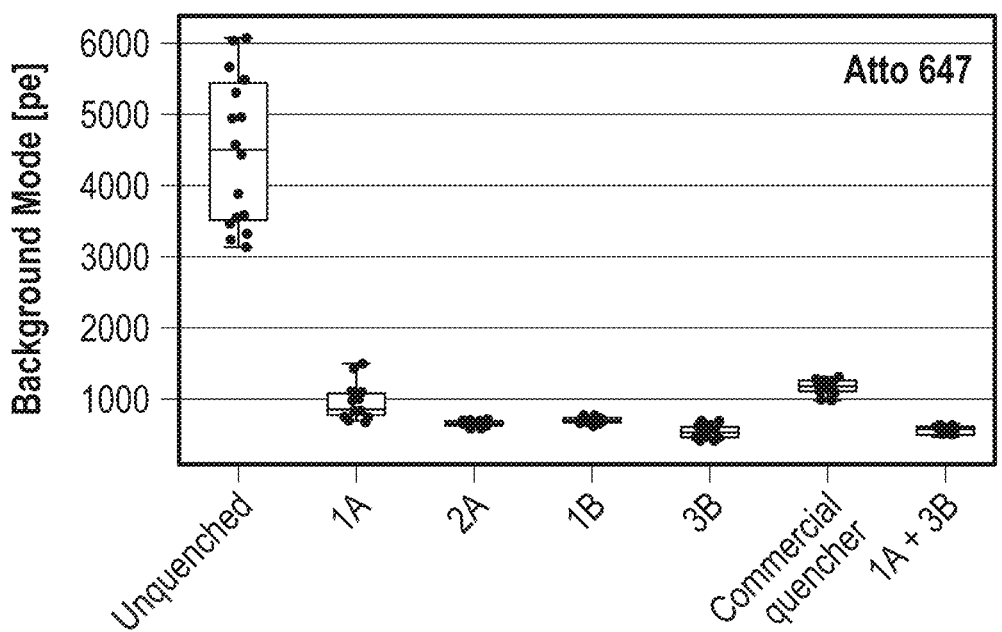

As shown in FIG. 4A-4C, FFPE human brain tissue showed similar reduction in background autofluorescence (FIG. 4B) relative to unquenched FFPE human brain tissue (FIG. 4A) even after stripping with DMSO and rehybridization (FIG. 4C). Further studies were conducted on FFPE human brain tissue that were enriched for binding moieties in the tissue via treatment with DTT or with DTT and PEG4-SPDP. FIG. 5 depicts the signal-to-noise ratio increased post-quenching with DTT/Compound 1A and PEG4-SPDP-DTT/Compound 1A, and was maintained after stripping with DMSO treatment and rehybridization of fluorescent probes.

As shown in FIG. 6A-6D, the signal to background ratio was maintained even after 5 cycles of stripping and rehybridizing with fluorescent probes in all four wavelengths imaged (488 nm, 590 nm, 532 nm, and 647 nm).

These data highlight the advantages of using compound 1A for in situ applications. As seen in the figures, the covalently bound compound 1A is retained on tissues through multiple detection cycles and does not require repeated quenching steps. The targeting moieties present in quencher contribute to the high durability of the quenchers to remain intact on the tissue. The quenching steps are performed on the bench and not on the instrument, thus eliminating any extra design efforts to accommodate commercial quenchers. Targeted quenching due to the anchoring chemistry facilitates higher selectivity. Furthermore, the chemical structure of the compound 1A can be modified to support feasibility for both aqueous and organic applications. The linker can be modified with hydrophilic groups or stimuli-driven cleavable functional groups (such as smart autofluorescence masking) to facilitate higher solubility. Finally, tissue pretreatment with DTT or PEG4-SPDP/DTT can further enrich targeting chemistry reactive sites on tissue samples, further reducing the overall autofluorescence.

Example 3: Method for Targeted Masking of Autofluorescence Using Analogues of Custom Quenchers with Varied Chemistries The present example describes the use of different types of quenchers, including compounds 1A, 2A, 1B, and 3B, for masking autofluorescence of human brain tissues.

Formalin-fixed paraffin embedded (FFPE) human brain tissues were treated using the protocol described in Example 1 and further treated using 50 mM DTT for 30 minutes. Next, the tissues were incubated with the quenchers (1 mM) for 30 minutes prior to staining. Staining was performed using nucleic acid probes targeting an anchor sequence which is present within all of the RCPs and targeting epithelial genes-rp1p0, malat1, and actb. The tissues were stained with the quencher compounds 1A, 2A, 1B, 3B, a combination of quenchers 1A and 3B, or a commercial quencher (Table 1, for comparison). Tissues stained with the four quencher compounds and the combination of quenchers 1A and 3B displayed significant reduction in the background signal in all four wavelength channels (488 nm, 532 nm, 590 nm, 647 nm) as compared to the unquenched tissues (FIGS. 7A-7D).

Figure 8A:
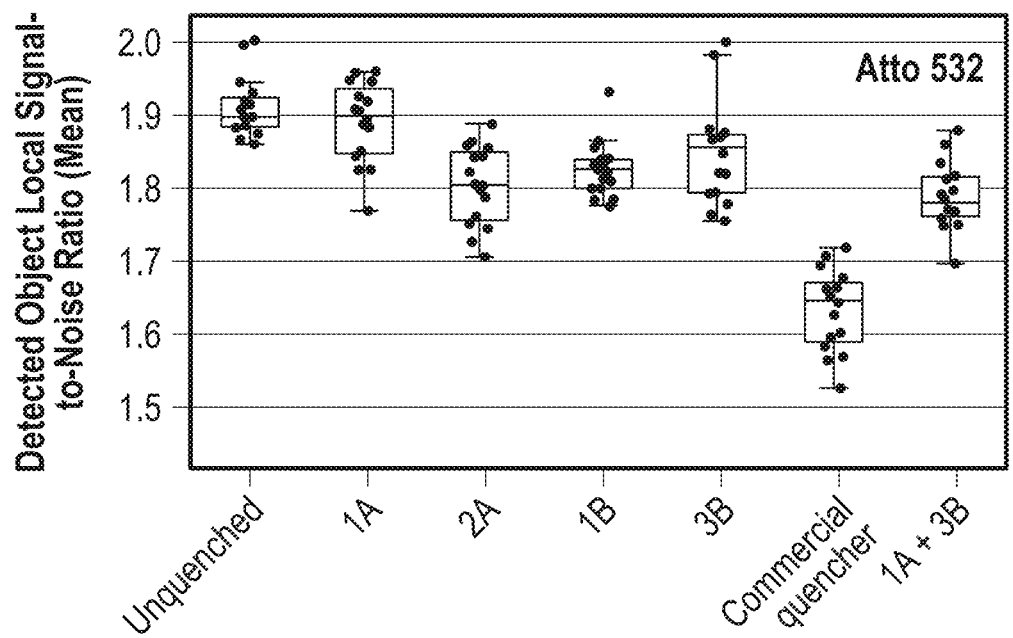
FIGS. 8A-8C depict the detected object local mean signal-to-noise ratio of tissues quenched with compounds 1A, 2A, 1B, 3B, or a combination of 1A and 3B, in comparison to a commercial quencher and an unquenched control.
Figure 8B:
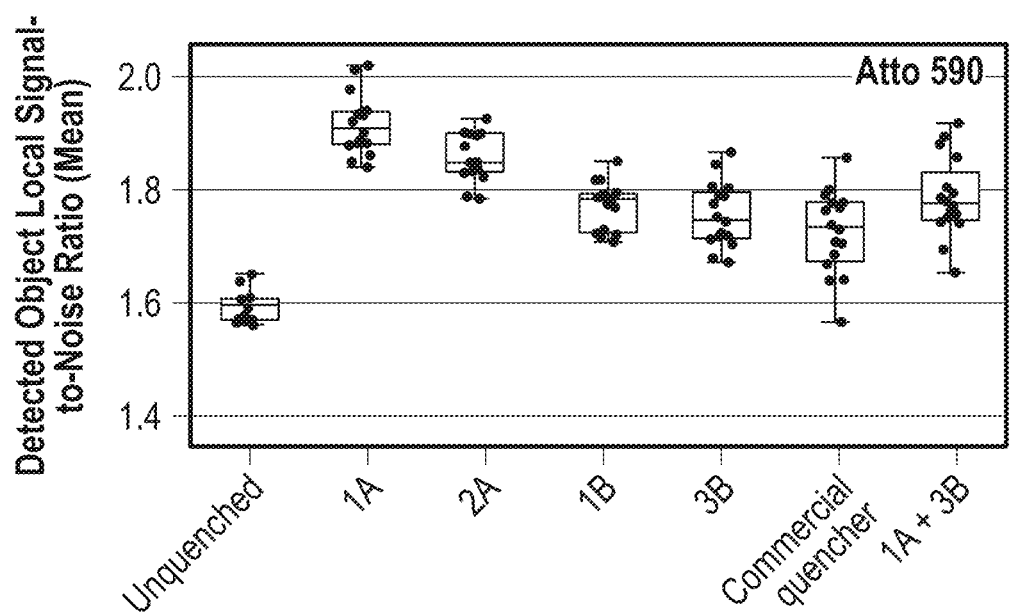
Figure 8C:
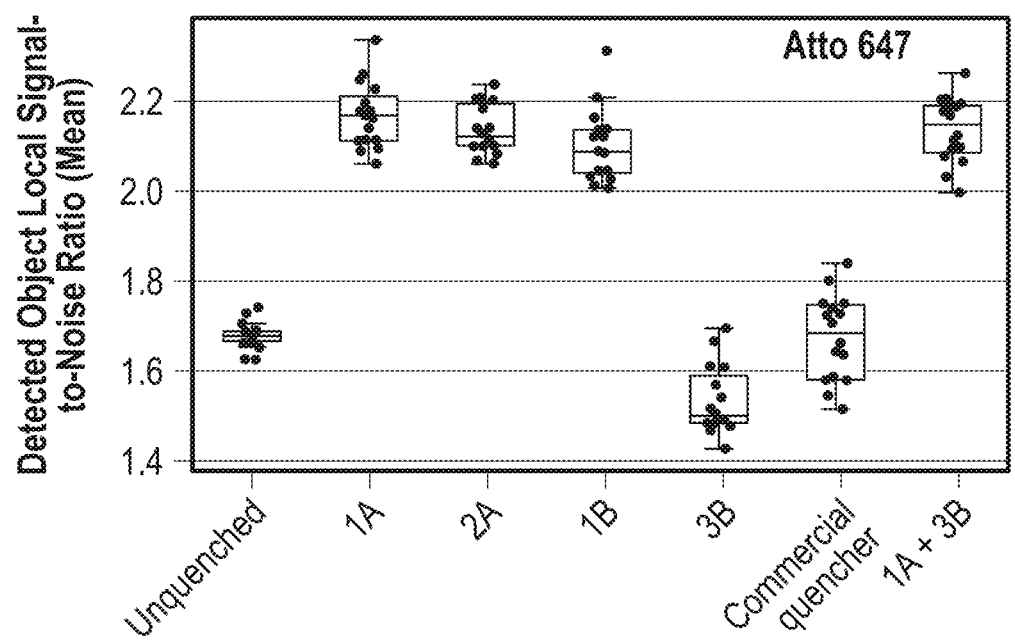

FIGS. 8A, 8B, and 8C depict the detected object local mean signal-to-noise ratio in wavelengths, 532 nm, 590 nm, and 647 nm, respectively. As shown in the figures, the tissues stained with the 1A, 2A, and 1B quenchers showed improved signal-to-noise ratios at 590 nm and 647 nm wavelengths. Additionally, tissues stained with 1A, 2A, and 1B showed improved signal-to-noise ratios at 590 nm and 647 nm wavelengths (FIGS. 8B and 8C). This Example illustrates that the different quencher analogues with varied targeting moieties and quencher dyes can significantly reduce background autofluorescence and improve signal-to-noise ratios across different wavelengths.

Example 4: Comparison of Quenchers Over Multiple Cycles in Human Tonsil and Liver Tissues The present example describes quenchers and their autofluorescence masking effects at different concentrations, across multiple cycles and wavelengths in human tonsil and liver tissues.

Formalin-fixed paraffin embedded (FFPE) human tonsil and liver tissues were obtained for this example. The samples were sectioned to 5 μm thickness and transferred to Superfrost® Plus slides. The samples were treated multiple times with Histo-Clear® and citrate buffer to remove the embedded paraffin and incubated overnight with nucleic acid probes targeting epithelial genes. The next day, the samples were washed with wash buffers to remove excess or unbound probes. The probes were then ligated in the presence of ligase, RNAase inhibitor and ligation buffer for 2 hours. Subsequently, the ligation products were amplified overnight using polymerases and amplification buffers. The samples were then stained using fluorescently labelled probes. Prior to staining, the samples with treated with DTT (1 mM) for 10 minutes and quenchers with different concentrations of the compound 1A (0.1 mM, 0.5 mM, and 0.8 mM). Images of control samples without compound 1A treatment were obtained for comparison. Samples were imaged in two field of views (FOVs) to control for photo bleaching. Once imaged, the fluorescently labelled probes were stripped using a denaturing agent and contacted with additional detectable probes before the next imaging round. In this manner, multiple rounds of stripping, re-probing, and imaging of signals associated with the fluorescently labelled probes, were performed without any additional quenching steps.

Figure 9A:
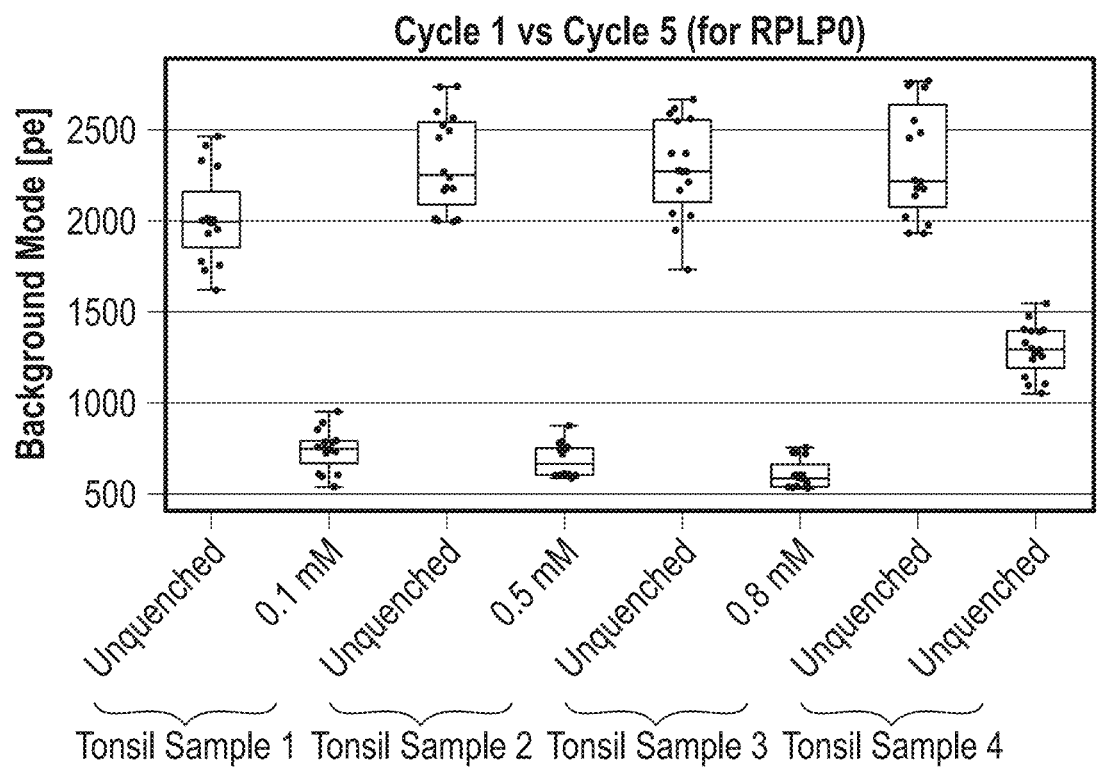
FIGS. 9A-9C display the background signals of in situ detection of different genes (RPLP0, GAPDH, and ACTB) in tonsil tissues before and after quenching with compound 1A (0.1 mM, 0.5 mM, and 0.8 mM concentrations) and imaged using detectable probes targeting rolling circle amplification (RCA) products for the genes. The detectable probes were detected using ATTO 488 labeled detection oligonucleotides. Four tonsil tissue samples were used for staining. Cycles 1, 2, and 3 represent imaging cycles before quenching and cycles 5, 6, and 7 represent imaging cycles after quenching.
Figure 9B:
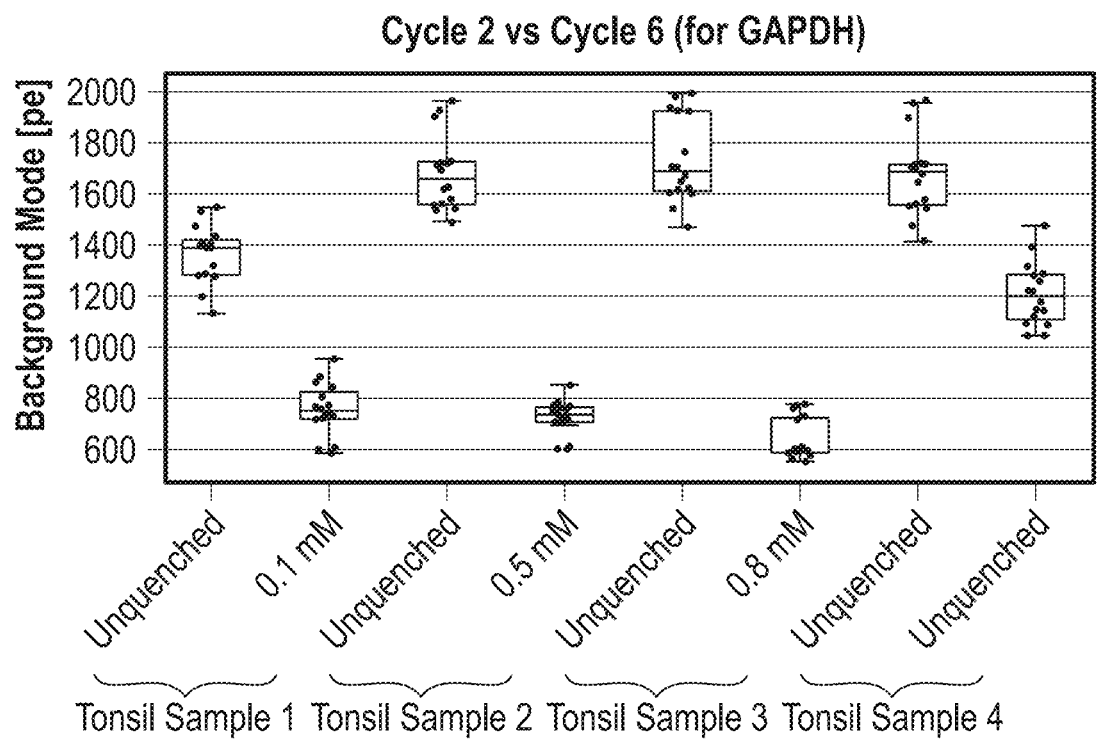
Figure 9C:
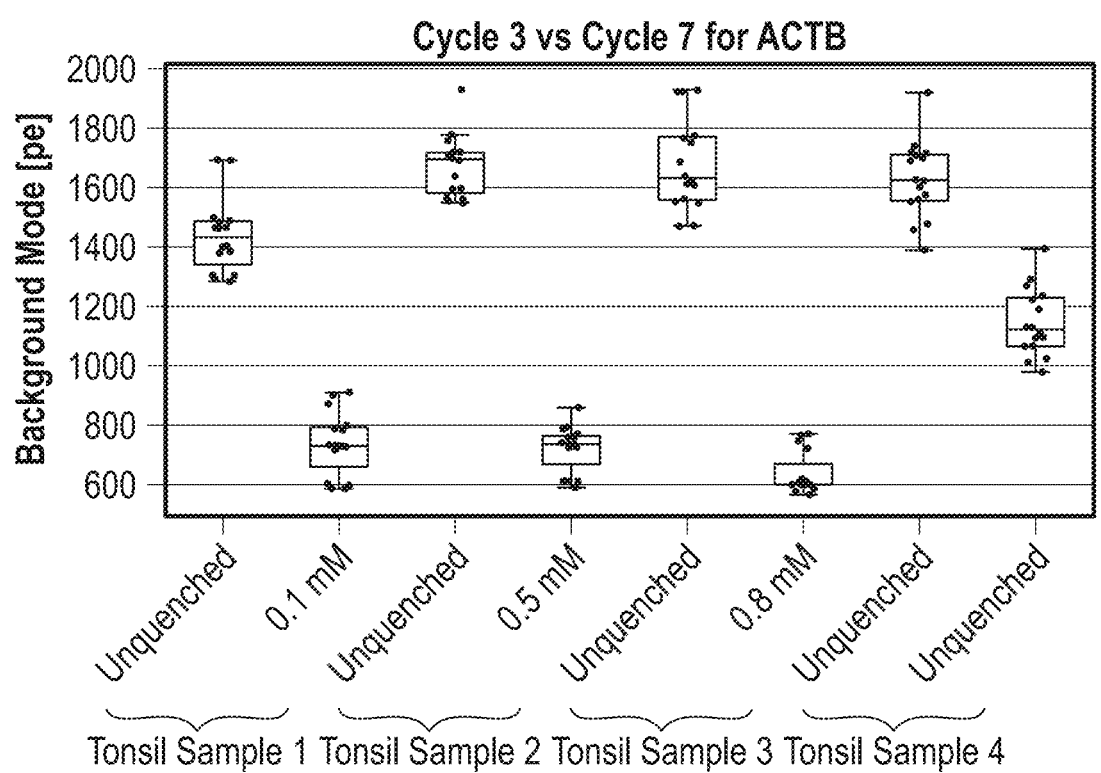
Figure 10A:
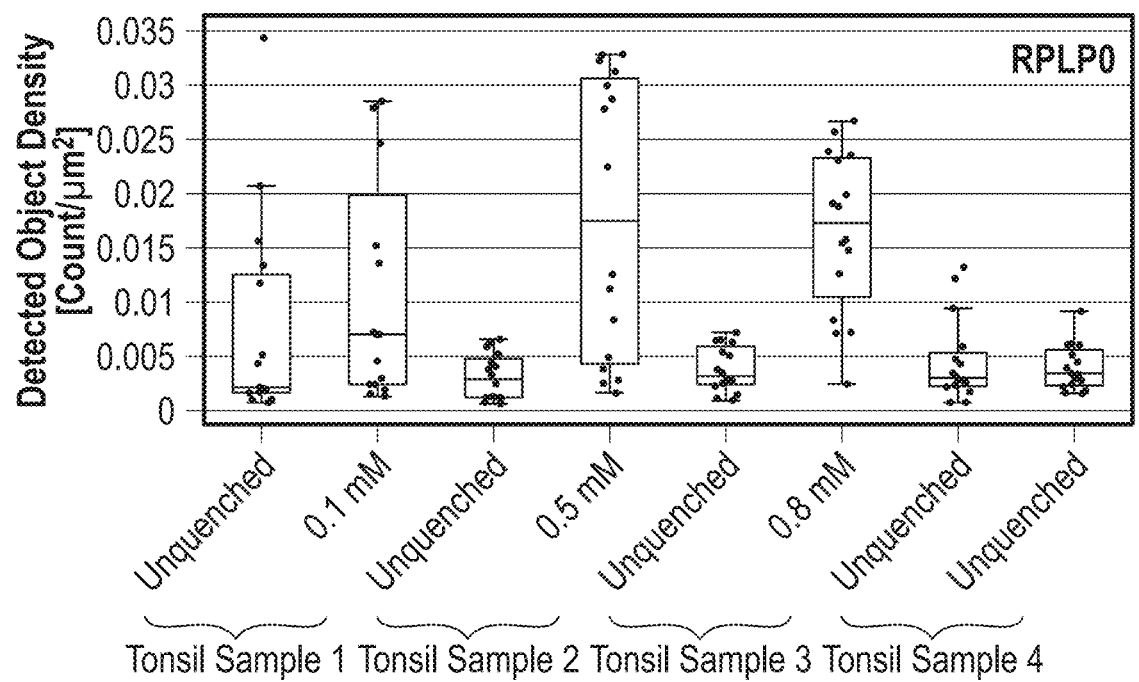
FIGS. 10A-10C depict detected object density (count of RCA products per $\mu m^2$ of nucleus area) of tonsil tissues quenched with compound 1A (0.1 mM, 0.5 mM, and 0.8 mM concentrations) imaged using ATTO 488-labeled detectable probes. An increase in detected object density was observed upon treatment with all the concentrations of compound 1A.
Figure 10B:
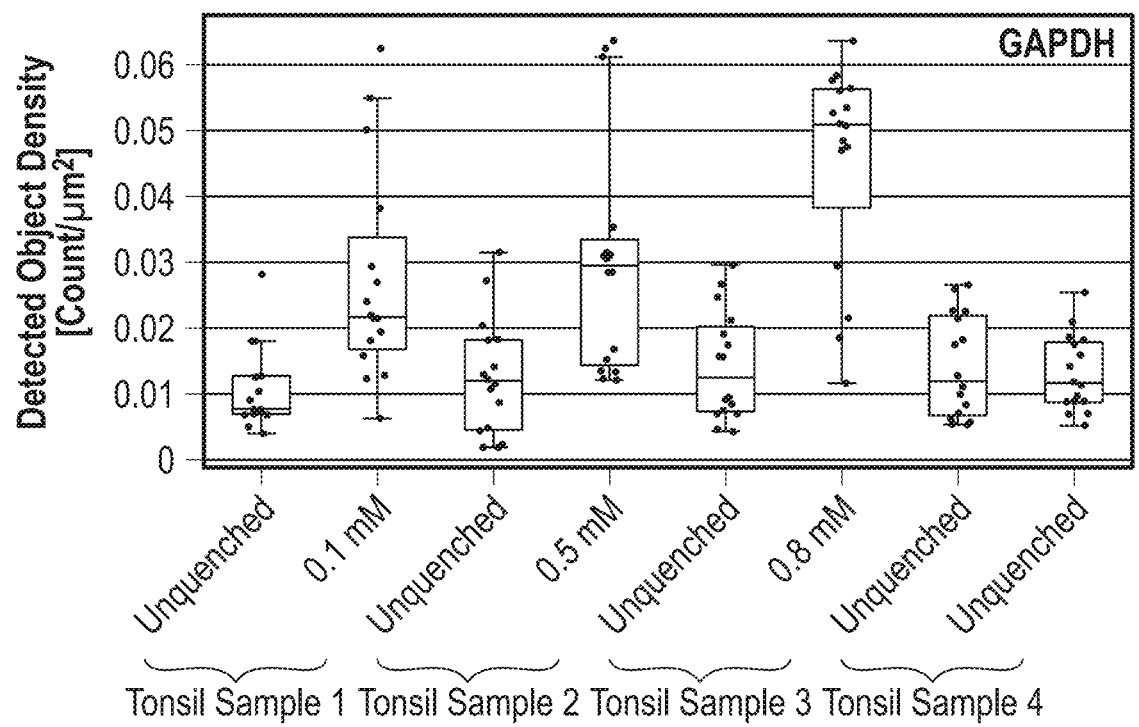
Figure 10C:
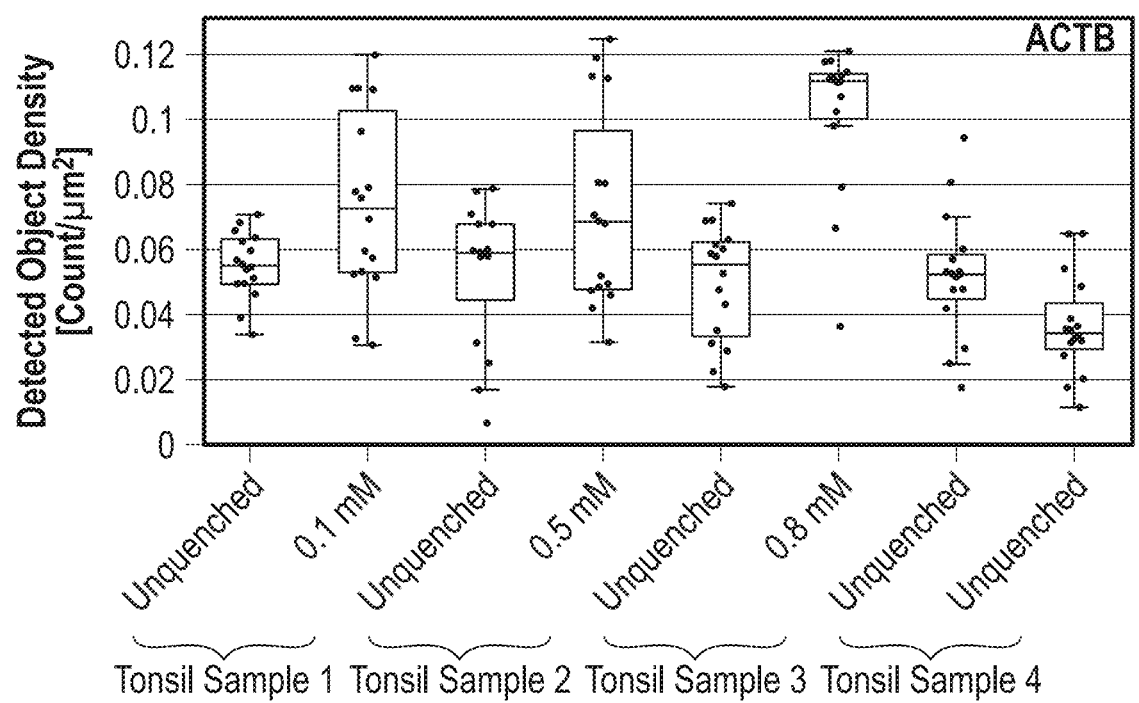
Figure 11A:
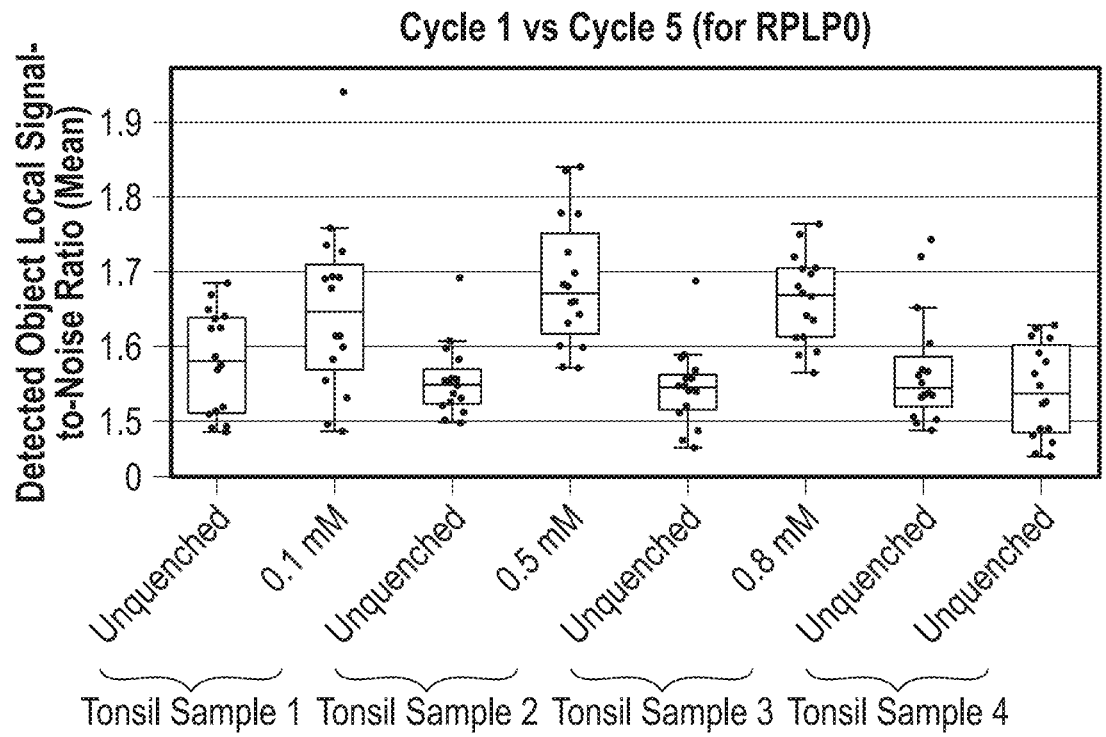
FIGS. 11A-11C display detected object local signal-to-noise ratios (mean) of tonsil tissues quenched with the quencher compound 1A (0.1 mM, 0.5 mM, and 0.8 mM concentrations). Increased signal-to-noise ratios were observed at 488 nm across all the concentrations of compound 1A tested.
Figure 11B:
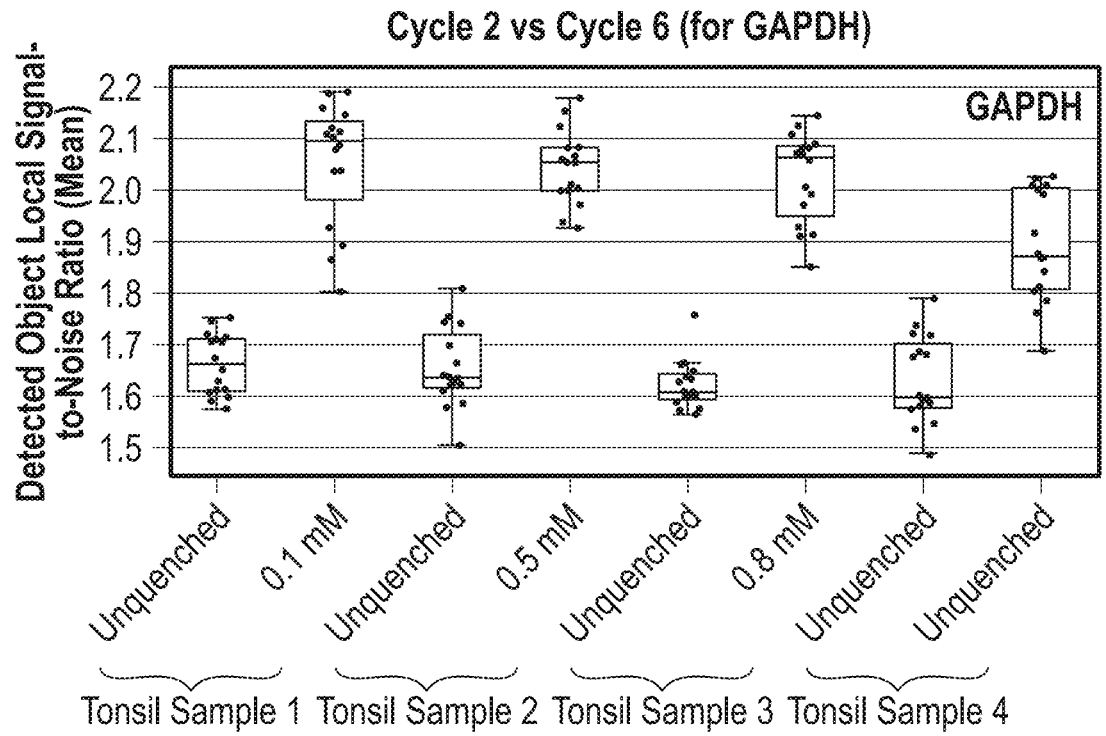
Figure 11C:
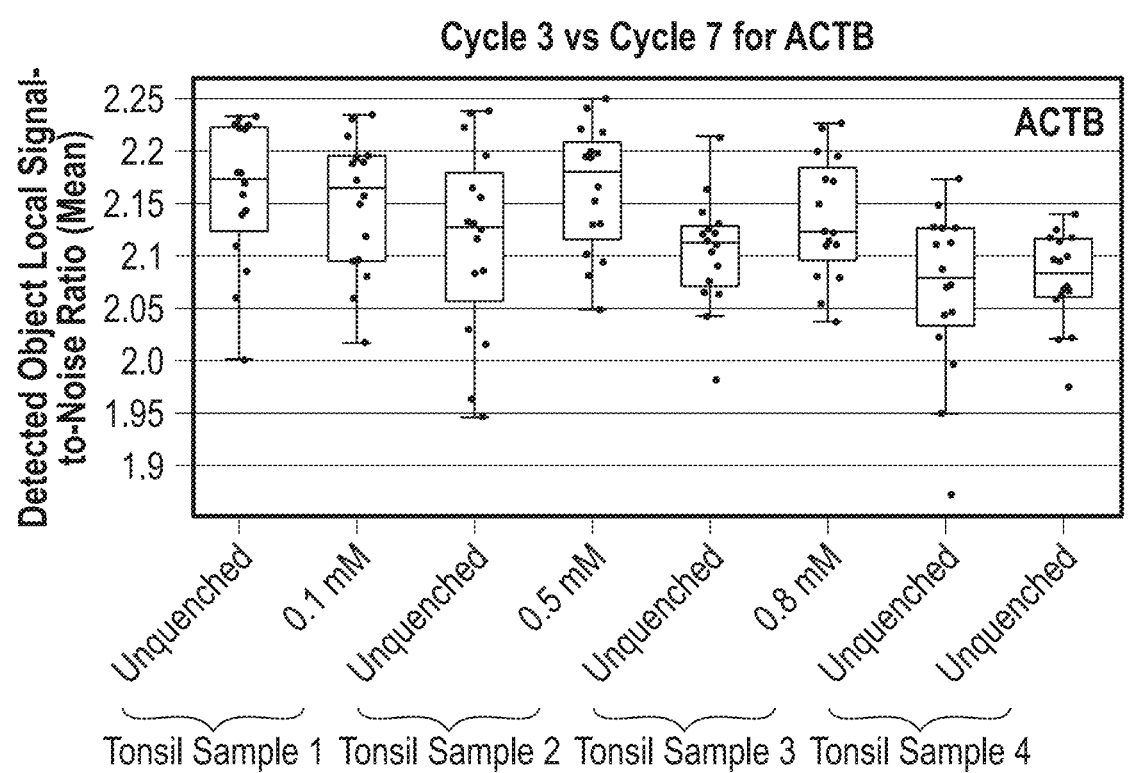
Figure 12:
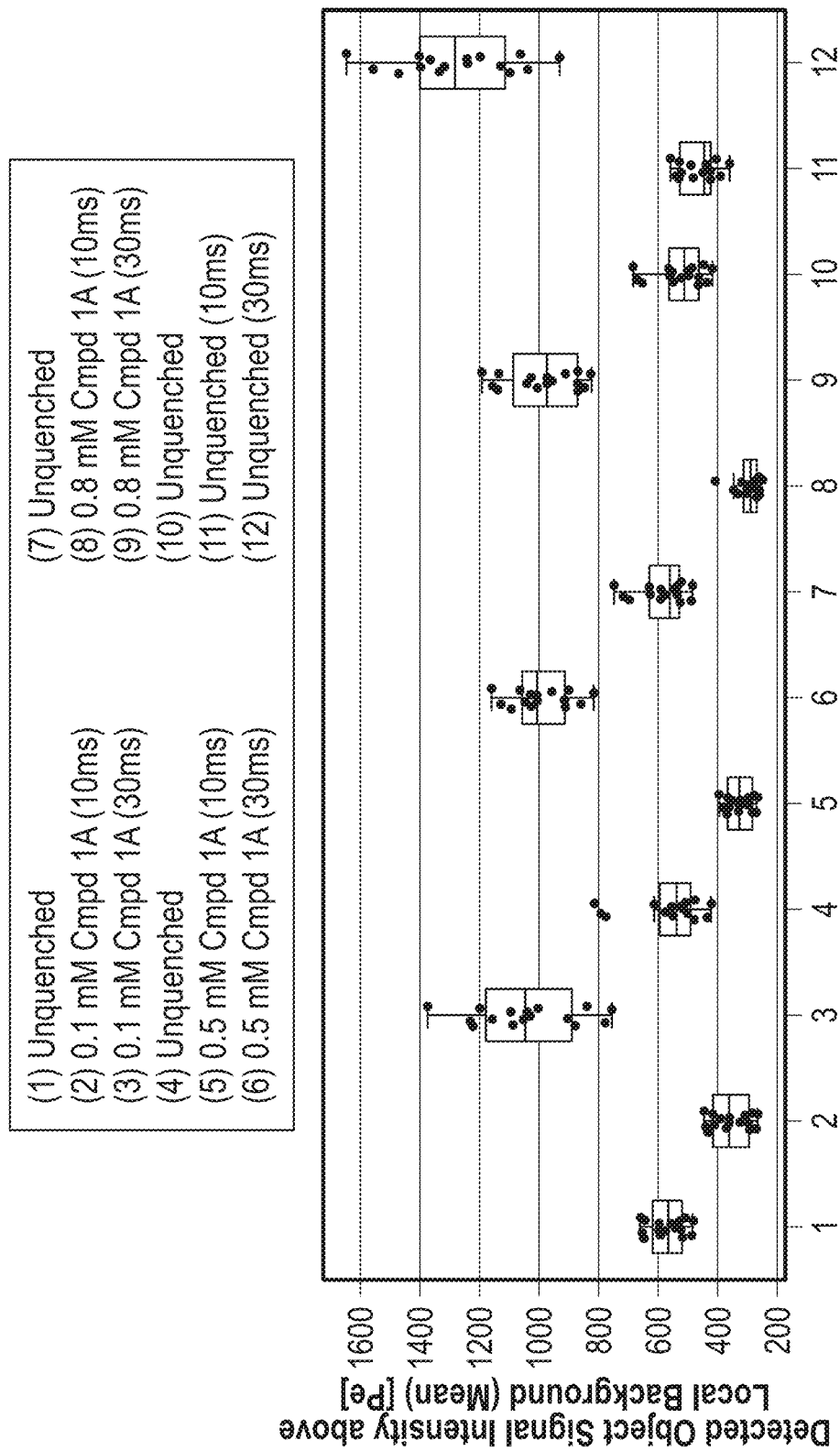
FIG. 12 shows detected objected signal intensity above local background in tonsil tissues quenched with the quencher compound 1A (0.1 mM, 0.5 mM and 0.8 mM concentrations) and imaged at 488 nm. The background intensity of quenched tissues imaged at 10 millisecond (10 ms) exposures were compared to those imaged at 30 millisecond (30 ms) exposures. Increasing exposure time from 10 milliseconds to 30 milliseconds significantly improved detected objected signal intensity above local background.

As shown in FIGS. 9A-9C significant reduction of background signal was observed across all the concentrations tested and over multiple cycles of stripping and reprobing, as compared to the unquenched tonsil tissues. FIGS. 9A-9C, show background signals of tissues imaged at 488 nm in cycles 1, 2, and 3 as compared to cycles 5, 6, and 7, respectively. The reduced background noise was maintained across all four wavelengths measured (data for additional wavelengths 532 nm, 590 nm and 647 nm not shown). Further, an increase in detected object density was observed upon treatment with all the concentrations of compound 1A (FIGS. 10A-10C) at 488 nm. Finally, increased signal-to-noise ratios were observed at 488 nm across all the concentrations of compound 1A tested (FIGS. 11A-11C). While quenching reduced signal intensity at 488 nm, increasing exposure time from 10 milliseconds to 30 milliseconds significantly improved detected objected signal intensity above local background (FIG. 12).

The images and quantitation revealed in this Example indicate that the analogs of compound 1A significantly reduce background fluorescence, increase detected object density and improve signal-to-noise ratios across various concentrations of quenchers, multiple tissue types, various wavelengths and over numerous cycles of stripping, re-probing and imaging.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

What is claimed is:

1. A method, comprising:
   (a) contacting a biological sample with a quencher comprising a quencher dye and a targeting moiety, wherein the targeting moiety covalently binds with a biological moiety endogenous to the biological sample, thereby targeting the quencher to the biological moiety;
   (b) contacting the biological sample with a detectable probe that binds to a molecule of interest in the biological sample; and
   (c) detecting a signal associated with the detectable probe bound to the molecule of interest in the biological sample,
   thereby detecting the molecule of interest in the biological sample.

2. The method of claim 1, wherein autofluorescence in the biological sample is reduced by at least 50% as compared to an unquenched biological sample.

3. The method of claim 1, wherein the signal associated with the detectable probe is detected at a location in the biological sample, and the detected signal has a signal-to-noise ratio that is increased as compared to an unquenched biological sample.

4. The method of claim 1, wherein the biological sample is contacted with the detectable probe in the contacting step (b) prior to being contacted with the quencher in the contacting step (a).

5. The method of claim 1, wherein the biological sample is contacted with the detectable probe in the contacting step (b) after being contacted with the quencher in the contacting step (a).

6. The method of claim 1, further comprising bleaching the biological sample with a chemical reagent, an enzyme, light, heat, or any combination thereof, prior to, simultaneously, or after the contacting in step (a).

7. The method of claim 1, further comprising removing the detectable probe or a portion thereof from the biological sample, wherein the quencher remains in the biological sample.

8. The method of claim 7, wherein the removing step comprises treating the biological sample with a denaturing agent comprising dimethyl sulfoxide (DMSO), formamide, and/or an alkaline solution.

9. The method of claim 1, wherein the quencher dye comprises:
   (a) at least three aromatic residues, wherein each aromatic residue is independently an unsubstituted aryl, a substituted aryl, an unsubstituted heteroaryl, or a substituted heteroaryl, wherein at least one of said aromatic residues is covalently linked to two other aromatic residues via two exocyclic azo bonds; or
   (b) at least two aromatic residues, wherein each aromatic residue is independently an unsubstituted aryl, a substituted aryl, an unsubstituted heteroaryl, or a substituted heteroaryl, wherein at least two of said aromatic residues are covalently linked via an exocyclic azo bond, and wherein at least one said aromatic residue is an unsubstituted polycyclic aryl, a substituted polycyclic aryl, an unsubstituted polycyclic heteroaryl group, or a substituted polycyclic heteroaryl group.

10. The method of claim 1, wherein the quencher dye comprises an optionally substituted 1,4-bis ((E)-phenyldiazenyl) benzene moiety

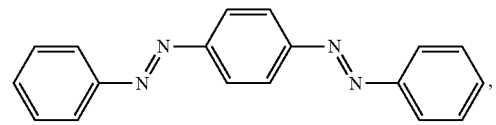

an optionally substituted (E)-5-phenyl-3-(phenyldiazenyl) phenazin-5-ium moiety

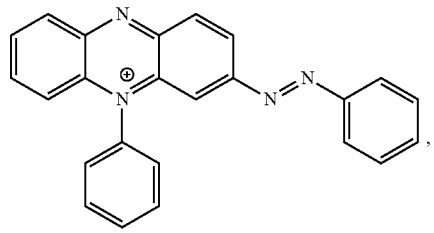 [SMILES: c1ccc(/N=N/c2ccc3nc4ccccc4[n+](-c4ccccc4)c3c2)cc1]

or a salt thereof.

11. The method of claim 10, wherein the quencher has a UV-visible absorption profile with at least one absorption peak with an absorption maximum between 400 nm and 700 nm and a full-width half-maximum of at least 100 nm.

12. The method of claim 1, wherein the quencher is a compound of formula (I)

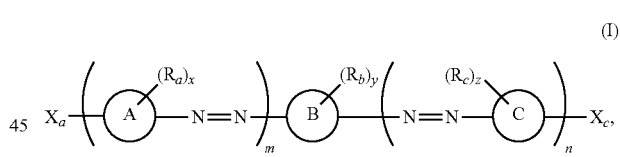

or a salt thereof, wherein
each

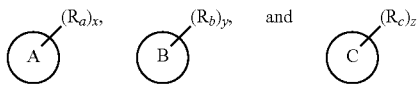

is independently selected from the group consisting of a substituted or unsubstituted aryl, and a substituted or unsubstituted heteroaryl;

$X_a$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —NR$^1$R$^2$, —NO$_2$, —SO$_3$H, —SO$_3^-$, —OSO$_2$—$C_1$-$C_6$ alkyl, —OSO$_2$—$C_1$-$C_6$ haloalkyl, —CN, —SCN, —NCO, or -L-($R^{target}$)$_w$, wherein w is 1 or 2;

$X_c$ is H, halo, —OH, $C_1$-$C_6$ alkyl, $C_1$-$C_6$ haloalkyl, $C_1$-$C_6$ alkoxy, $C_1$-$C_6$ haloalkoxy, hydroxyl-$C_1$-$C_6$ alkylene, —NR¹R², —NO₂, —SO₃H, —SO₃⁻, —OSO₂—C₁-C₆ alkyl, —OSO₂—C₁-C₆ haloalkyl, —CN, —SCN, —NCO, or -L-(R$_{target}$)$_w$, wherein w is 1 or 2;

wherein R¹ and R² are independently H, C₁-C₆ alkyl or substituted C₁-C₆ alkyl; and each R$_a$ and R$_c$ is independently H, halo, —OH, C₁-C₆ alkyl, C₁-C₆ haloalkyl, C₁-C₆ alkoxy, C₁-C₆ haloalkoxy, hydroxyl-C₁-C₆ alkylene, —NR¹R², —NO₂, —SO₃H, —SO₃⁻, —OSO₂—C₁-C₆ alkyl, —OSO₂—C₁-C₆ haloalkyl, —CN, —SCN, or —NCO;

each R$_b$ is independently H, halo, —OH, C₁-C₆ alkyl, C₁-C₆ haloalkyl, C₁-C₆ alkoxy, C₁-C₆ haloalkoxy, hydroxyl-C₁-C₆ alkylene, —NR¹R², —NO₂, —SO₃H, —SO₃⁻, —OSO₂—C₁-C₆ alkyl, —OSO₂—C₁-C₆ haloalkyl, —CN, —SCN, —NCO, R$_{b1}$, or -L-(R$_{target}$)$_w$, wherein w is 1 or 2;

R$_{b1}$ is a substituted or unsubstituted alkyl, a substituted or unsubstituted aryl, or a substituted or unsubstituted heteroaryl;

L is a bond or a linker moiety;

R$_{target}$ is a targeting moiety;

m is an integer from 0 to 6;

n is an integer from 0 to 6; and each of x, y, and z is independently an integer from 0 to 5;

provided that at least one of m and n is nonzero; and provided that at least one of X$_a$, X$_c$, or R$_b$ is -L-(R$_{target}$)$_w$, wherein w is 1 or 2.

13. The method of claim 12, wherein each of at least one, at least two, or at least three instances of

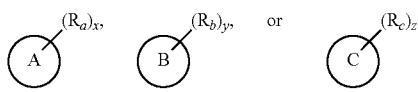

is a substituted phenyl or an unsubstituted phenyl.

14. The method of claim 12, wherein the quencher has the following structure:

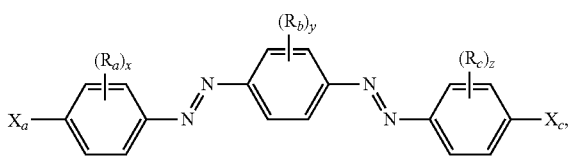

or a salt thereof, provided that at least one of X$_a$ and X$_c$ is -L-(R$_{target}$)$_w$, wherein w is 1 or 2, and wherein L is a bond or a linker moiety; and R$_{target}$ is a targeting moiety.

15. The method of claim 12, wherein

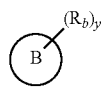

is:

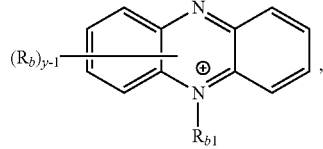

wherein R$_{b1}$ is a substituted or unsubstituted alkyl, a substituted or unsubstituted aryl, or a substituted or unsubstituted heteroaryl.

16. The method of claim 15, wherein

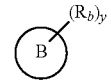

is

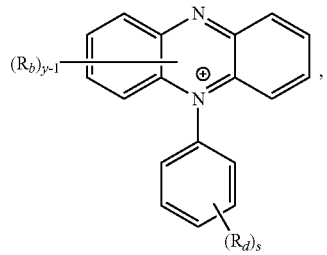

wherein R$_d$ is H, C₁-C₆ alkyl, or halo; and s is an integer from 0 to 5.

17. The method of claim 12, wherein the quencher has the following structure:

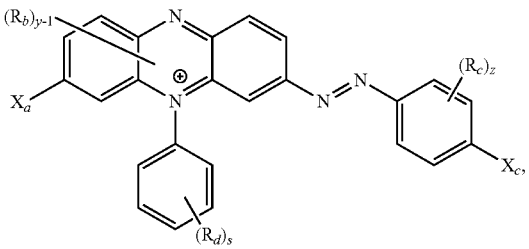

or a salt thereof, wherein R$_d$ is H, C₁-C₆ alkyl, or halo; and s is an integer from 0 to 5.

18. The method of claim 1, wherein the molecule of interest is a nucleic acid of interest or a protein of interest.

19. The method of claim 1, wherein the targeting moiety comprises a first functional group, and the endogenous biological moiety comprises a second functional group capable of reacting with the first functional group to form a covalent bond.

20. The method of claim 19, wherein the first functional group is a carboxylic acid moiety or derivative thereof, an aldehyde or ketone moiety, a sulfonyl halide moiety, a hydroxyl moiety, a thiol moiety, an amino moiety, an alkenyl or dienyl moiety, an epoxide moiety, or a haloalkyl moiety.

21. The method of claim 20, wherein the first functional group is a maleimido moiety, an azido moiety, an alkynyl moiety, an N-hydroxysuccinimidyl ester moiety, or a carbonylimidazolyl moiety.

22. The method of claim 21, wherein the first functional group is a maleimido moiety.
23. The method of claim 1, wherein the quencher is selected from the group consisting of:
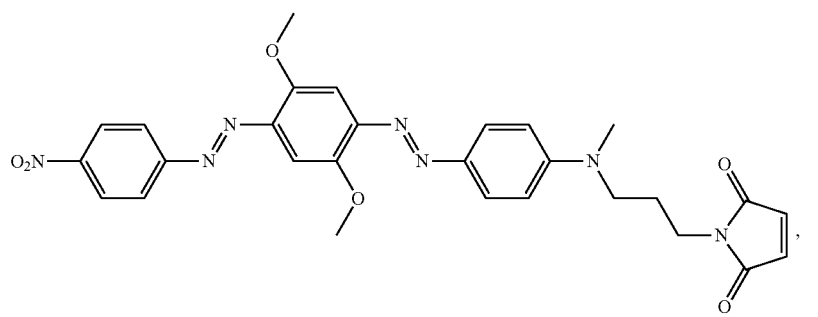
,
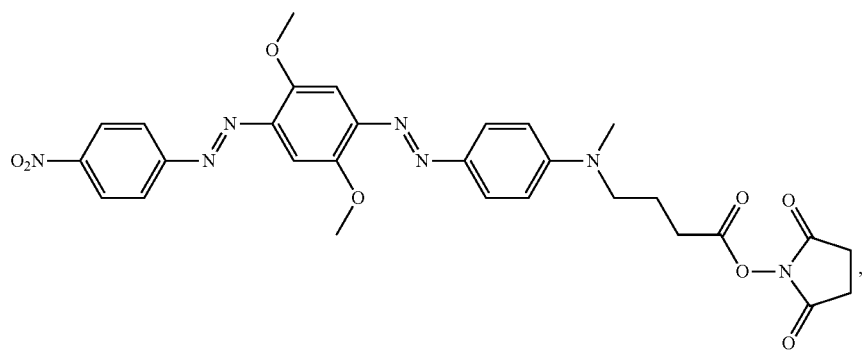
,
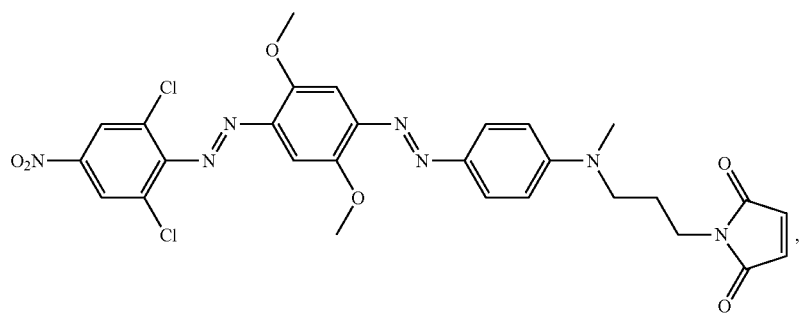
,
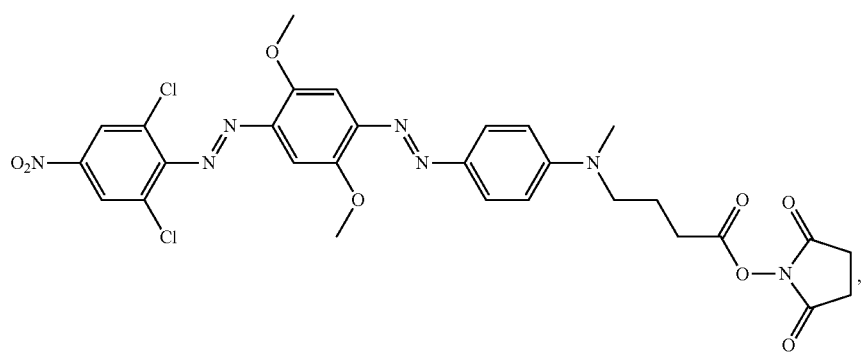
,
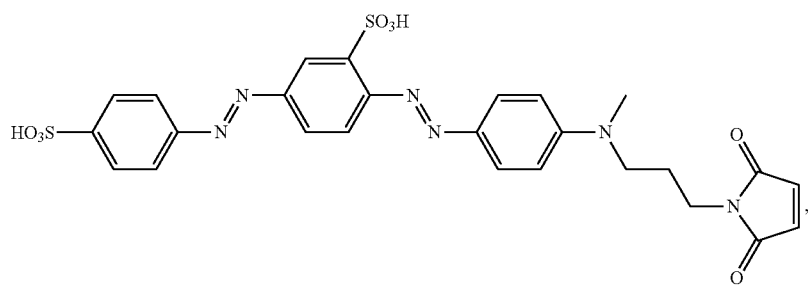
, -continued
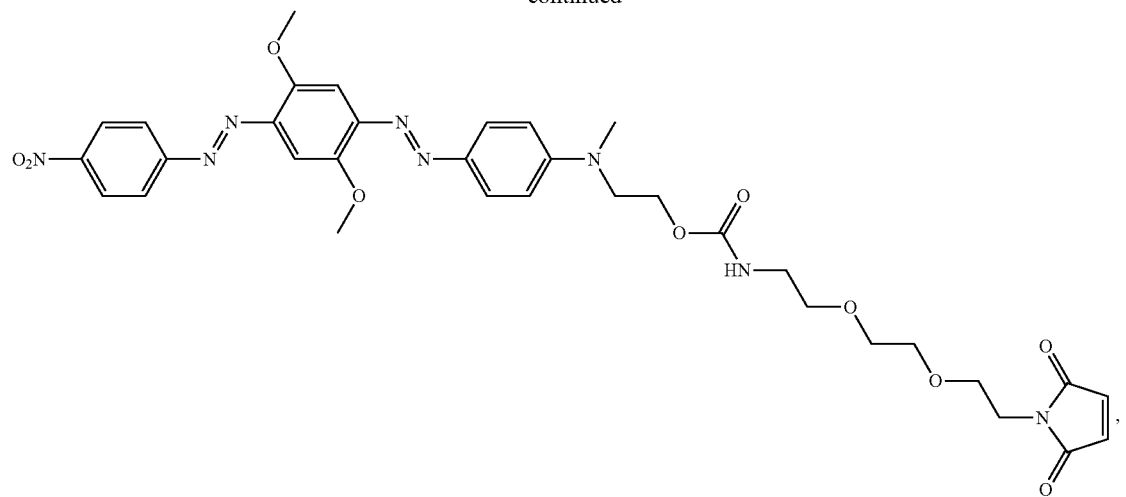
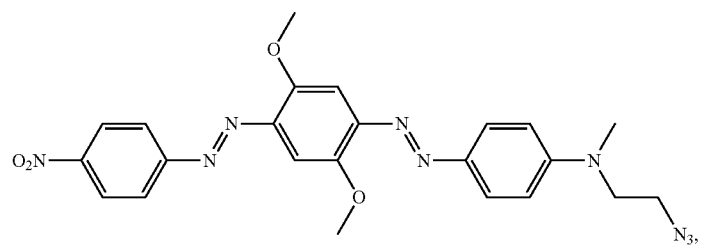
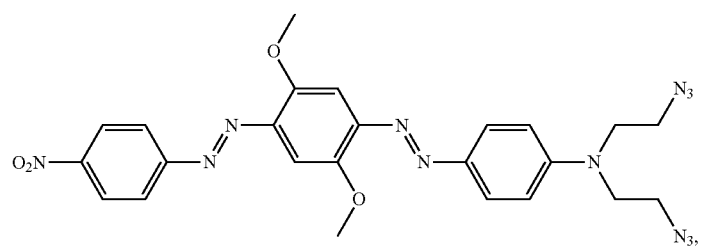
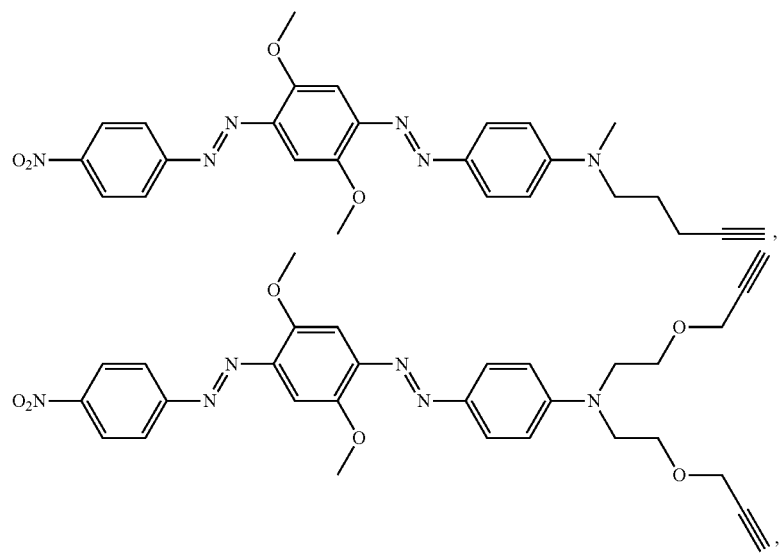

-continued
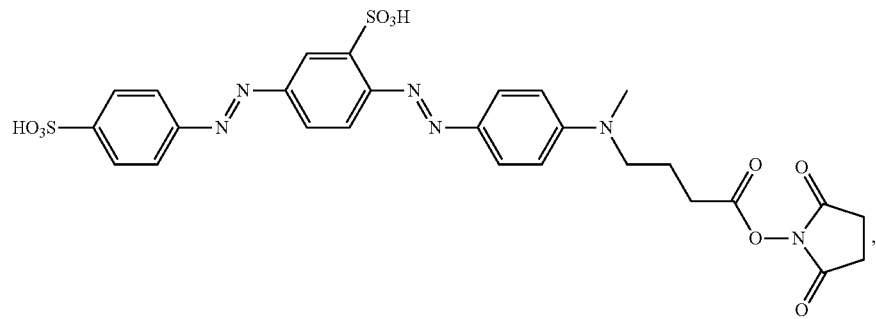
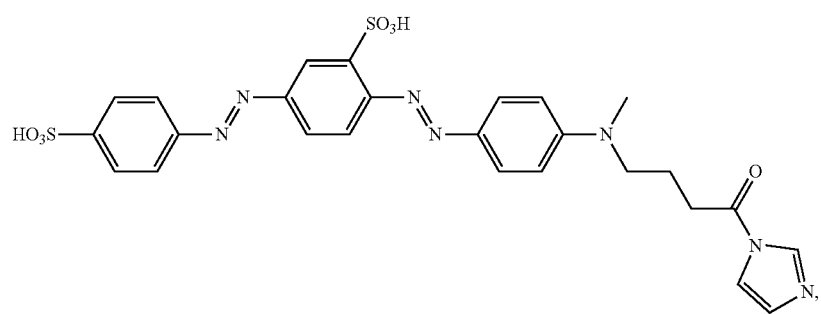
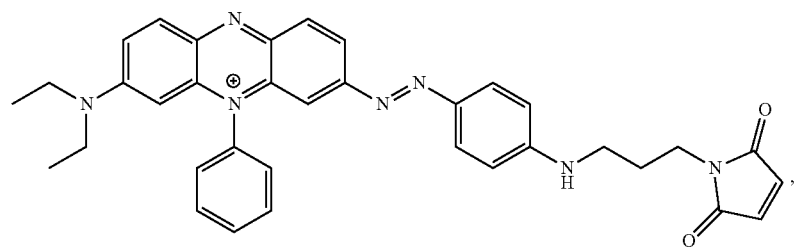
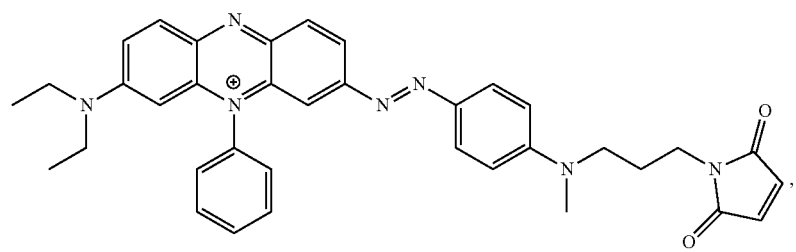
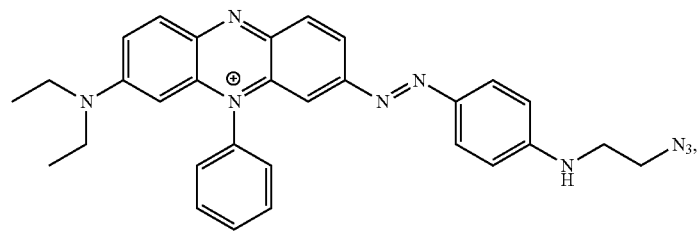
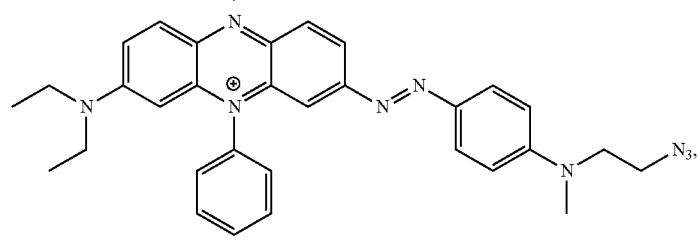

-continued
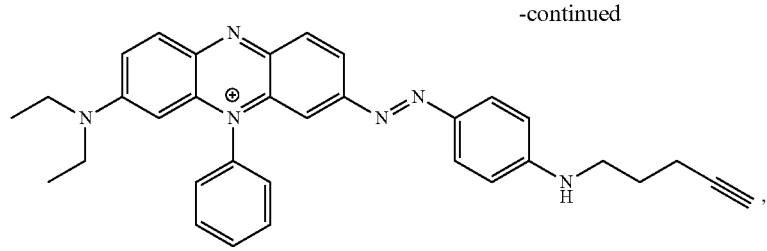
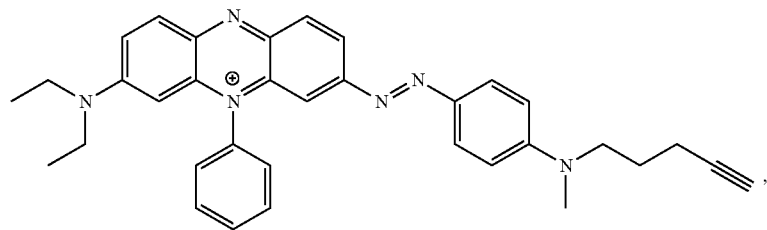
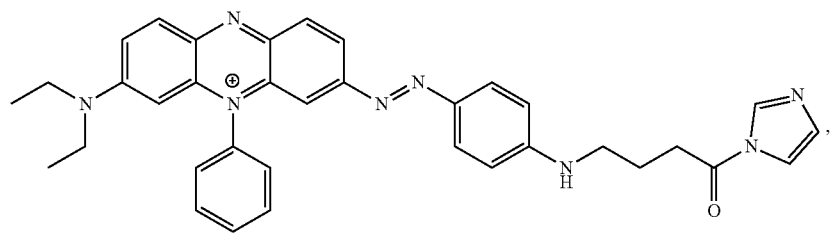
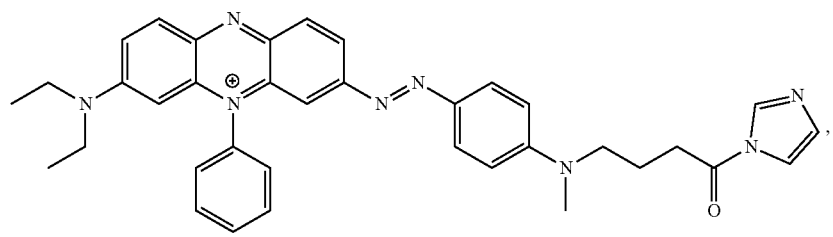
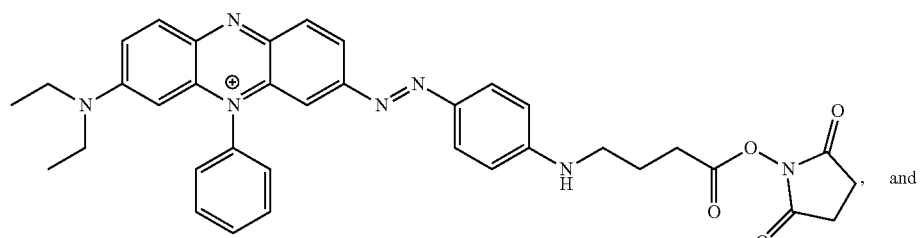, and
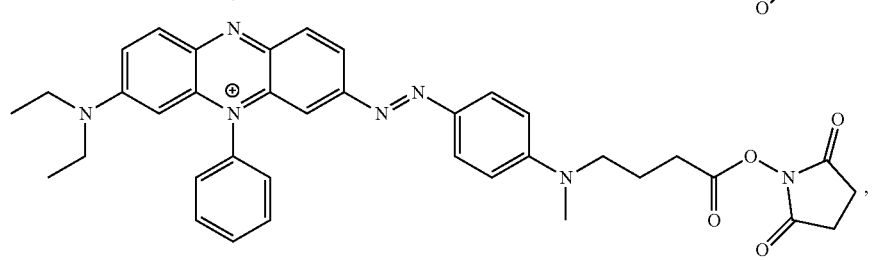
and any salt thereof.

24. The method of claim 1, wherein the quencher is a compound selected from the group consisting of:
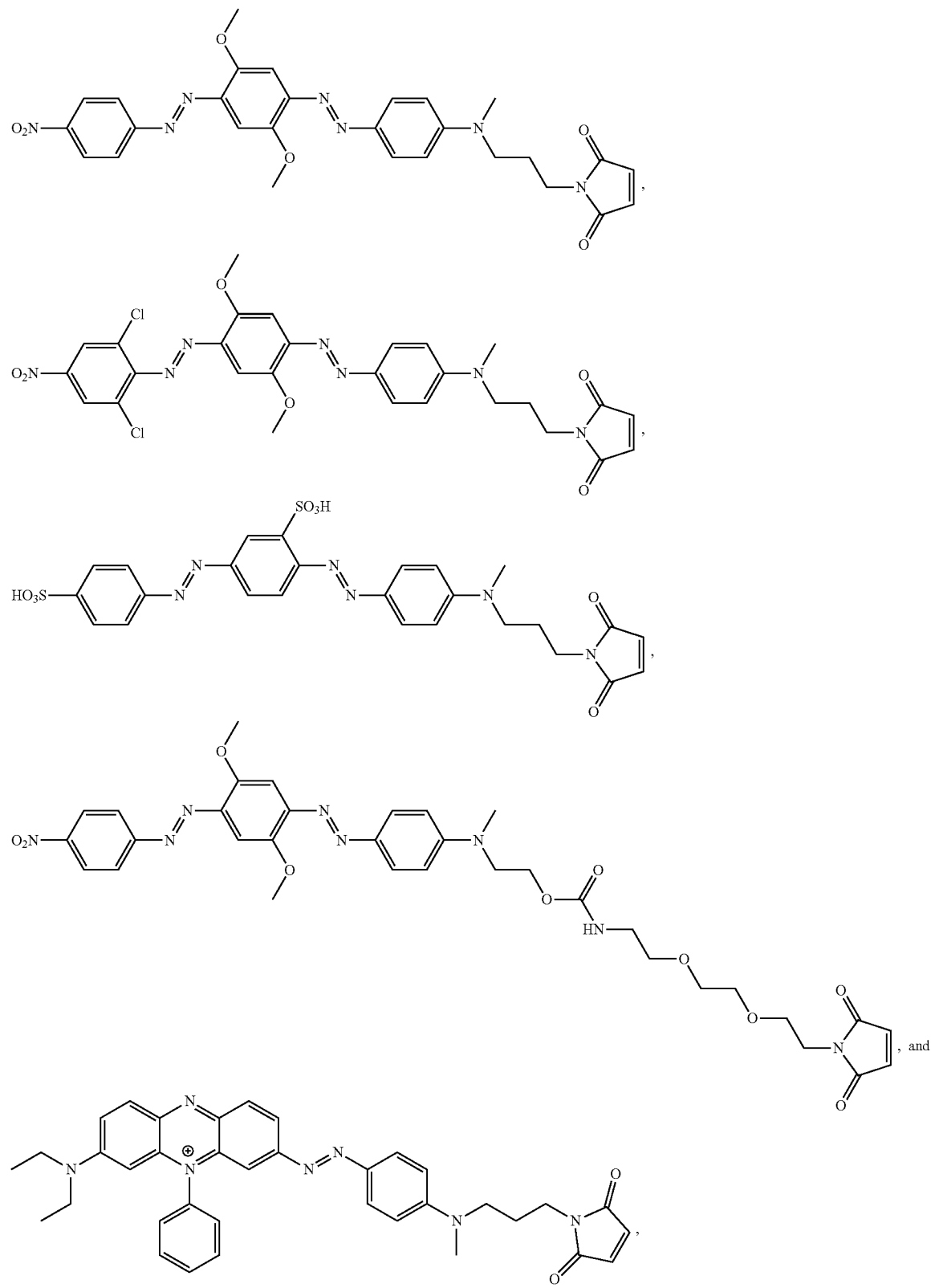
and any salt thereof.

25. The method of claim 19, further comprising a step of treating the biological sample to enrich, create, and/or introduce the second functional group in the endogenous biological moiety.

26. The method of claim 25, wherein the second functional group is thiol, and the biological sample is treated with a reducing agent to convert disulfide groups to thiol groups.

27. The method of claim 25, wherein the endogenous biological moiety comprises a third functional group, which is different from the second functional group, and wherein the biological sample is treated with a heterobifunctional crosslinker comprising the second functional group and a fourth functional group capable of reacting with the third functional group to form a covalent bond, thereby introducing the second functional group in the endogenous biological moiety.

28. The method of claim 1, further comprising removing the detectable probe by treating the biological sample with a denaturing agent and/or heating, wherein the quencher remains in the biological sample, and contacting the biological sample with one or more additional detectable probes after treating the biological sample with the denaturing agent and/or heating.

29. The method of claim 1, wherein the biological moiety endogenous to the biological sample is a polypeptide or a lipid.

30. The method of claim 12, wherein the biological sample is a tissue sample and the method further comprises, prior to (a):

(a') contacting the tissue sample with a nucleic acid probe that binds to an analyte in the tissue sample, wherein the detectable probe in (b) is a fluorescently labeled detectable probe and the molecule of interest is the nucleic acid probe or an amplification product of the nucleic acid probe, and wherein the quencher dye reduces autofluorescence in the tissue sample.

* * * * *